(12) United States Patent
Swanson et al.

(10) Patent No.: US 7,964,570 B2
(45) Date of Patent: Jun. 21, 2011

(54) METHODS AND COMPOSITIONS FOR TREATMENT OF MYOTONIA

(75) Inventors: Maurice S. Swanson, Gainesville, FL (US); Rahul N. Kanadia, Gainesville, FL (US); Charles A. Thornton, Rochester, NY (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 229 days.

(21) Appl. No.: 10/591,883

(22) PCT Filed: Mar. 10, 2005

(86) PCT No.: PCT/US2005/007631
§ 371 (c)(1),
(2), (4) Date: Dec. 10, 2007

(87) PCT Pub. No.: WO2005/086825
PCT Pub. Date: Sep. 22, 2005

(65) Prior Publication Data
US 2008/0213182 A1 Sep. 4, 2008

Related U.S. Application Data

(60) Provisional application No. 60/551,748, filed on Mar. 10, 2004.

(51) Int. Cl.
*A61K 48/00* (2006.01)
*C12N 5/00* (2006.01)
*C12N 5/02* (2006.01)
*C07H 21/02* (2006.01)
(52) U.S. Cl. .................. 514/44 R; 435/325; 536/23.1
(58) Field of Classification Search .............. 514/44 R; 435/325; 536/23.1
See application file for complete search history.

(56) References Cited

OTHER PUBLICATIONS

Patil et al. The AAPS Journal, 7(1): Article 9, E61-E77, 2005.*
Juengst et al. BMJ, 326: 1410-1411, Jun. 28, 2003.*
Kay et al. Nature Med., 7(1): 33-40, Jan. 2001.*
Trent. Chapter 6, Genetics and Cellular Therapies from Molecular Med: An Introductory Text, 2005, pp. 143-173.*
Gregorevic. Expert. Opin. Biol. Ther., 3(5): 803-814, 2003.*
Wikipedia. Trinucleotide repeat disorder, accesed online, May 5, 2009 at en.wikipedia.com.*
Synder et al. Human Gene Therapy, 8: 1891-1900, Nov. 1997.*
Uniprot website "MBNL1" accessed online on May 10, 2009.*
Mankodi, et al., "Muscleblind Localizes to Nuclear Foci of Aberrant RNA in Myotonic Dystrophy Types 1 and 2", Human Molecular Genetics, 2001, vol. 10, No. 19, 2165-2170.
Kanadia, et al., "A Muscleblind Knockout Model for Myotonic Dystrophy", Science, 2003, vol. 302, 1978-1980.
Miller, et al., Recruitment of Human Muscleblind Proteins to $(CUG)_n$ Expansions Associated with Myotonic Dystrophy, The Embo Journal, 2000, vol. 19, No. 17 pp. 4439-4448.
Hartigan-O'Connor, et al., "Developments in Gene Therapy for Muscular Dystrophy", Microscopy Research and Technique, 2000, 48:223-238.
International Search Report (Form PCT/ISA/220 (Jan. 2004).

* cited by examiner

*Primary Examiner* — Thaian N Ton
(74) *Attorney, Agent, or Firm* — Edwards Angell Palmer & Dodge LLP; Peter F. Corless; Melissa Hunter-Ensor, Esq.

(57) ABSTRACT

The present invention provides methods and compositions for the treatment of diseases associated with aberrant microsatellite expansions. Methods of the present invention comprise the use of recombinant adeno-associated virus vectors containing a transgene encoding at least one muscleblind protein. The present invention also provides an animal model for a disease associated with aberrant microsatellite expansion.

8 Claims, 18 Drawing Sheets ed States Government has certain rights to the invention
METHODS AND COMPOSITIONS FOR TREATMENT OF MYOTONIA

RELATED APPLICATIONS/PATENTS & INCORPORATION BY REFERENCE

The present application is a U.S. national stage application based on PCT/US05/007631 entitled Methods and Compositions for Treatment of Diseases Associated with Aberrant Microsatellite Expansion, filed Mar. 10, 2005, which claims priority to U.S. Provisional Application Ser. No. 60/551,748, filed on Mar. 10, 2004,the entire contents of each of which is incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

STATEMENT OF RIGHTS TO INVENTIONS MADE UNDER FEDERALLY SPONSORED RESEARCH

This work was supported in part by a grant from the National Institutes of Health (U54-NS48843). The United States Government has certain rights to the invention

BACKGROUND OF THE INVENTION

Microsatellite Expansion Diseases

Aberrant expansion of microsatellites in DNA is associated with a number of neurological and neuromuscular diseases (O'Donnell, W T, Warren, S T (2002), *Annu. Rev. Neurosci.* 25: 315). These diseases are caused by microsatellite repeat expansions in coding and non-coding regions. The characterized coding region expansion diseases include Dentatorubral pallidoluysian atrophy (DRPLA), Huntington chorea (HD), Oculopharyngeal muscular dystrophy (OPMD), Spinobulbar muscular atrophy (SBMA), and Spinocerebellar ataxia types 1, 2, 3, 6, 7, and 17 (SCA1, SCA2, SCA3, SCA6, SCA7, SCA17). The characterized non-coding region expansion diseases include Fragile XA, Fragile XE, Friedrich's ataxia, Myotonic Dystrophy type 1 (DM1), Myotonic Dystrophy type 2 (DM2), and Spinocerebellar ataxia types 8, 10, and 12 (SCA8, SCA10, SCA12). Huntington's disease-like type 2 (HDL2) is likewise caused by a microsatellite expansion.

Microsatellite expansion diseases have been most commonly associated with trinucleotide expansion mutations. In fact, at least 16 of the microsatellite expansion diseases reported to date have been characterized as trinucleotide expansion diseases. More recently, however, microsatellite expansion diseases have also been associated with tetranucleotide and even pentanucleotide expansion mutations. Disease severity and age of onset have both been related to the size of the expansion mutation, eventually leading to muscle weakness and premature cataract formation, and, in severe cases, to hypotonia, muscle heart block, and nervous system dysfunction (Korade-Mirnics, Z, Babitzke, P, Hoffman, E (1998) *Nuc. Acids Res.* 26(6): 1363-1368).

Myotonic dystrophy (dystrophia myotonica, DM) is a multisystemic, dominantly inherited disorder often characterized by myotonia, or, delayed muscle relaxation due to repetitive action potentials in myofibers, and muscle degeneration. Manifestations of DM may also include heart block, ocular cataracts, hypogonadism, and nervous system dysfunction.

Myotonic dystrophy type 1 (DM1) is caused by a trinucleotide $(CTG)_n$ expansion (n=50 to >3000) in the 3'-untranslated region (3'UTR) of the Dystrophia myotonica-protein kinase (DMPK) gene. Myotonic dystrophy type 2 (DM2) is caused by a tetranucleotide $(CCTG)_n$ expansion (n=75 to ~11,000) in the first intron of zinc finger protein 9 (ZNF9) gene (Ranum, L P W, Day, J W (2002) *Curr. Opin. in Genet. and Dev.* 12:266-271).

Although the expansions are located on different chromosomes, there appears to be a common pathogenic mechanism involving the accumulation of transcripts into discrete nuclear RNA foci containing long tracts of CUG or CCUG repeats expressed from the expanded allele (Liquori C L, Ricker K, Moseley M L, Jacobsen J F, Kress W, Naylor S L, Day J W, Ranum L P (2001), *Science* 293: 864-867).

In effect, both DM1 and DM2 mutant transcripts accumulate as foci within muscle nuclei (Liquori, et al., 2001). An indication that these transcripts are pathogenic comes from studies on $HSA^{LR}$ mice, which express a large CTG repeat in the 3'-UTR of a human skeletal actin transgene (Mankodi, A, Logigian, E, Callahan, L, McClain, C, White, R, Henderson, D, Krym, M, Thornton, C A (2000) *Science* 289: 1769-1773). These transgenic mice develop myonuclear RNA foci, myotonia, and degenerative muscle changes similar to those seen in human DM. The myotonia in $HSA^{LR}$ mice is caused by loss of skeletal muscle chloride (ClC-1) channels due to aberrant pre-mRNA splicing (Mankodi, A, Takahashi, M P, Jiang, H, Beck, C L, Bowers, W J, Moxley, R T, Cannon, S C, Thornton, C A (2002) *Mol. Cell* 10: 35-44). Similar ClC-1 splicing defects exist in DM1 and DM2. However, the connection between accumulation of mutant DM transcripts in the nucleus and altered splice site selection has not been established (Faustino, N A, Cooper, T A (2003) *Genes Dev.* 17: 419-437).

The RNA gain-of-function hypothesis proposes that mutant DM transcripts alter the function and localization of alternative splicing regulators, which are critical for normal RNA processing. Consistent with this proposal, misregulated alternative splicing in DM1 has been demonstrated for six pre-mRNAs: cardiac troponin T (cTNT), insulin receptor (IR), muscle-specific chloride channel (ClC-1), tau, myotubularin-related protein 1 (MTMR1) and fast skeletal troponin T (TNNT3) (Kanadia R N, Johnstone K A, Mankodi A, Lungu C, Thornton C A, Esson D, Timmers A M, Hauswirth W W, Swanson M S (2003), *Science* 302: 1978-1980).

In all cases, normal mRNA splice variants are produced, but the normal developmental splicing pattern is disrupted, resulting in expression of fetal protein isoforms that are inappropriate for adult tissues. The insulin resistance and myotonia observed in DM1 correlate with the disruption of splicing of two pre-mRNA targets, IR and ClC-1, respectively (Savkur R S, Philips A V, Cooper T A, Dalton J C, Moseley M L, Ranum L P, Day J W (2004), *Am J Hum Genet* 74:1309-1313).

The mechanism by which expanded repeats alter the regulation of pre-mRNA alternative splicing is unclear. Two families of RNA-binding proteins have been implicated in DM1 pathogenesis: CUG-BP1 and ETR-3-like factors (CELF) and muscleblind-like (MBNL) proteins (Ladd A N, Charlet-B N, Cooper T A (2001), *Mol Cell Biol* 21: 1285-1296). Six CELF (also called BRUNOL) genes have been identified in humans (Ladd A N, Nguyen N H, Malhotra K, Cooper T A (2004), *J Biol Chem* 279: 17756-17764). All six CELF proteins have been shown to regulate pre-mRNA alternative splicing and two (CUG-BP1 and ETR-3/CUG-BP2) have been shown to have cytoplasmic RNA-associated functions (Mukhopadhyay D, Houchen C W, Kennedy S, Dieckgraefe B K, Anant S (2003), *Mol Cell* 11: 113-126).

A functional link has been established between splicing regulation by CELF proteins and DM1 pathogenesis. CUG-BP1 regulates alternative splicing of at least three of the pre-mRNAs (cTNT, IR and ClC-1) that are misregulated in DM striated muscle (Charlet-B N, Savkur R S, Singh G, Philips A V, Grice E A, Cooper T A (2002b), *Mol Cell* 10: 45-53). The splicing patterns observed for all three pre-mRNAs are consistent with increased CUG-BP1 activity and an increase in CUG-BP1 steady-state levels in DM1 striated muscle (Charlet-B N, Savkur R S, Singh G, Philips A V, Grice E A, Cooper T A (2002b), *Mol Cell* 10: 45-53).

Furthermore, cTNT minigenes expressed in DM1 muscle cultures or cTNT and IR pre-mRNAs co-expressed with CUG repeat RNA in normal cells reproduce the aberrant splicing patterns observed for endogenous genes in DM cells (Philips A V, Timchenko L T, Cooper T A (1998), *Science* 280: 737-741; Savkur R S, Philips A V, Cooper T A (2001), *Nat Genet* 29: 40-47). The trans-dominant effects of endogenous or co-expressed CUG repeat RNA on cTNT and IR splicing regulation require the intronic CUG-BP1-binding sites, indicating that binding by CUG-BP1 and/or other CELF family members to their cognate intronic regulatory elements is required for induction of aberrant splicing regulation by CUG repeat RNA (Philips A V, Timchenko L T, Cooper T A (1998), *Science* 280: 737-741; Savkur R S, Philips A V, Cooper T A (2001), *Nat Genet* 29: 40-47).

The CNS symptoms of DM1 may include cognitive impairment, hypersomnolence, heightened sensitivity to anesthetic agents, central hypoventilation, neuroendocrine dysfunction, and effects on personality and behavior [reviewed by Harper (Harper, P. S. (2001), *Myotonic dystrophy*. Saunders London) and Ashizawa (Ashizawa, T. (1998), *Arch. Neurol.*, 55, 291-293)]. Some of these effects, such as, mental retardation in individuals with congenital DM1, occur during development (Dyken, P. R., Harper, P. S. (1973), *Neurology*, 23, 465-473). Other symptoms, such as, hypersomnolence, appear during adult life. The mechanism and neuropathologic correlates for CNS involvement in DM1 are unknown.

It is presently unclear whether any steps in the pathogenic sequence of poly(CUG) expression, formation of RNA inclusions, sequestration of RNA binding proteins, and disruption of alternative splicing can take place in the CNS. There is controversy about which cells in the mature brain, if any, express DMPK (Lam, L. T., Pham, Y. C., Nguyen, T. M., and Morris, G. E. (2000), *Hum. Mol. Genet.*, 9, 2167-2173).

Microtubule-associated protein tau (MAPT) pre-mRNA is alternatively spliced at exons 2, 3, and 10 (Goedert, M., Spillantini, M. G., Jakes, R., Rutherford, D., and Crowther, R. A. (1989), *Neuron*, 3, 519-526). Tau transcripts in fetal brain do not include exon 10, whereas ~50% of transcripts in adult brain include this exon which encodes an additional microtubule binding domain (Hong, M., Zhukareva, V., Vogelsberg-Ragaglia, V., Wszokek, Z., Reed, L., Miller, B. I., Geschwind, D. H., Bird, T. D., McKeel, D., Goate, A. et al. (1998), *Science*, 282, 1914-1917). Alternative splicing of exons 2 and 3 also is developmentally regulated (neither exon is included in the fetus, adults mainly include exon 2).

The relative proportion of tau splice products is tightly regulated, as shown by kindreds with frontotemporal dementia and parkinsonism (FTDP-17) due to mutations in MAPT. Silent mutations in MAPT exon 10, or, in the flanking intron, lead to FTDP-17 by disrupting cis elements that regulate splicing of tau pre-mRNA (D'Souza, I., Poorkaj, P., Hong, M., Nochlin, D., Lee, V. M., Bird, T. D., and Schellenberg, G. D. (1999), *Proc. Natl. Acad. Sci. U.S.A*, 96, 5598-5603). Usually these mutations lead to increased inclusion of exon 10 (Lee, V. M., Goedert, M., and Trojanowski, J. Q. (2001), *Annu. Rev. Neurosci.*, 24, 1121-1159). However, some MAPT mutations that segregate with FTDP-17 have the opposite effect of reducing exon 10 inclusion (Stanford, P. M., Shepherd, C. E., Halliday, G. M., Brooks, W. S., Schofield, P. W., Brodaty, H., Martins, R. N., Kwok, J. B., and Schofield, P. R. (2003), *Brain*, 126, 814-826).

RNA-binding proteins that regulate alternative splicing bind to sequence-specific elements in the pre-mRNA to enhance or repress inclusion of alternative exons. Aberrant regulation of alternative splicing can cause the expression of inappropriate splicing patterns leading to human disease (Faustino and Cooper, 2003). Myotonic dystrophy constitutes an example of a disease that alters the function of RNA-binding proteins to cause misregulated alternative splicing.

BRIEF SUMMARY OF THE INVENTION

The present disclosure provides methods and compositions for treating diseases associated with aberrant microsatellite expansion employing recombinant adeno-associated virus (rAAV) expressing human muscleblind (MBNL) proteins.

One embodiment of the invention is directed to a method of treating a disease associated with aberrant microsatellite expansion, comprising administering to a mammal in need thereof, a therapeutically effective amount of recombinant adeno-associated virus (rAAV) containing a transgene that encodes a protein selected from the group consisting of MBNL1, MBNL2, MBNL3, and combinations thereof. In one embodiment of the invention, treating comprises ameliorating or eliminating the symptoms of a neuromuscular or neurological condition caused by the aberrant microsatellite expansion. In an additional embodiment of the invention, the neuromuscular condition is myotonic dystrophy.

In other embodiments of the invention, treating comprises reversing the mis-splicing of the Clcn1 skeletal muscle chloride channel, reversing the mis-splicing of the Amyloid beta (A4) precursor protein (APP), reversing the mis-splicing of the NMDA receptor NR1 (GRIN1), reversing the mis-splicing of the Microtubule-associated protein tau (MAPT), or reversing the mis-splicing of TNNT2 (cTNT), respectively.

One embodiment of the invention is directed to a method of treating a disease associated with aberrant microsatellite expansion, comprising administering to a mammal in need thereof, a therapeutically effective amount of recombinant adeno-associated virus (rAAV) containing a transgene that encodes MBNL1.

One embodiment of the invention is directed to a method of treating a disease associated with aberrant microsatellite expansion, comprising administering to a mammal in need thereof, a therapeutically effective amount of recombinant adeno-associated virus (rAAV) containing a transgene that encodes a protein selected from the group consisting of MBNL1, MBNL2, MBNL3, and combinations thereof, wherein the mammal is human. In another embodiment of the invention, the mammal in need of treatment has RNA inclusions in neuronal cells.

One embodiment of the invention is directed to pharmaceutical compositions comprising a recombinant adeno-associated virus (rAAV) containing a transgene that encodes at least one protein selected from the group consisting of MBNL1, MBNL2, MBNL3, and combinations thereof. In another embodiment of the invention, the protein is MBNL1.

The present disclosure also provides a mouse model for myotonic dystrophy, wherein the mouse has a substantial deletion of a muscleblind exon in its genome. Such an animal model for human disease allows the identification and testing of potential therapeutic and preventive agents.

Accordingly, one embodiment of the invention is directed to a mouse model for disease associated with aberrant microsatellite expansion, comprising a mouse having a substantial deletion of Mbnl1 exon 3 (E3) in the mouse genome, wherein said mouse exhibits symptoms typical of a disease associated with aberrant microsatellite expansion in humans. In another embodiment, the invention is directed to a cell isolated from said mouse. In one embodiment of the invention, the mouse exhibits symptoms such as muscle weakness and ocular cataracts.

In one embodiment, the invention is directed to a mouse model for disease associated with aberrant microsatellite expansion, comprising a mouse having a substantial deletion of Mbnl1 exon 3 (E3) in the mouse genome, wherein said mouse exhibits symptoms typical of a disease associated with aberrant microsatellite expansion in humans, wherein the microsatellite repeat expansion disease is caused by a microsatellite expansion in a coding region of DNA. In another embodiment of the invention, the microsatellite repeat expansion disease is caused by a microsatellite expansion in a non-coding region of DNA.

In one embodiment, the invention is directed to a mouse model for disease associated with aberrant microsatellite expansion, comprising a mouse having a substantial deletion of Mbnl1 exon 3 (E3) in the mouse genome, wherein said mouse exhibits symptoms typical of a disease associated with aberrant microsatellite expansion in humans, wherein the mouse exhibits abnormal muscleblind proteins. In other embodiments of the invention, the mouse may have a loss of functional ClC-1 protein, a loss of functional Amyloid beta (A4) precursor protein, a loss of functional NMDA receptor NR1, a loss of functional Microtubule-associated protein tau, a loss of functional TNNT2 protein, or a loss of functional TNNT3 protein, respectively.

One embodiment of the invention is directed to a method of identifying a compound useful in the treatment of disease associated with aberrant microsatellite expansion, comprising administering a test compound to a mouse having a substantial deletion of Mbnl1 exon 3 (E3) in the mouse genome, wherein said mouse exhibits symptoms typical of a disease associated with aberrant microsatellite expansion in humans, wherein the mouse exhibits abnormal muscleblind proteins, and monitoring said mouse for reduction or inhibition of the symptoms associated with said disease. In an additional embodiment, the mouse may be monitored for effects other than those associated with the disease. In one embodiment of the invention, the disease is myotonic dystrophy.

BRIEF DESCRIPTION OF THE FIGURES

FIG. 9A shows the results of the UV-cross-linking assays, wherein GST-MBNL1 bound weakly to MSE1 and strongly to MSE4.

DETAILED DESCRIPTION OF THE INVENTION

Muscleblind Proteins

Figure 1:
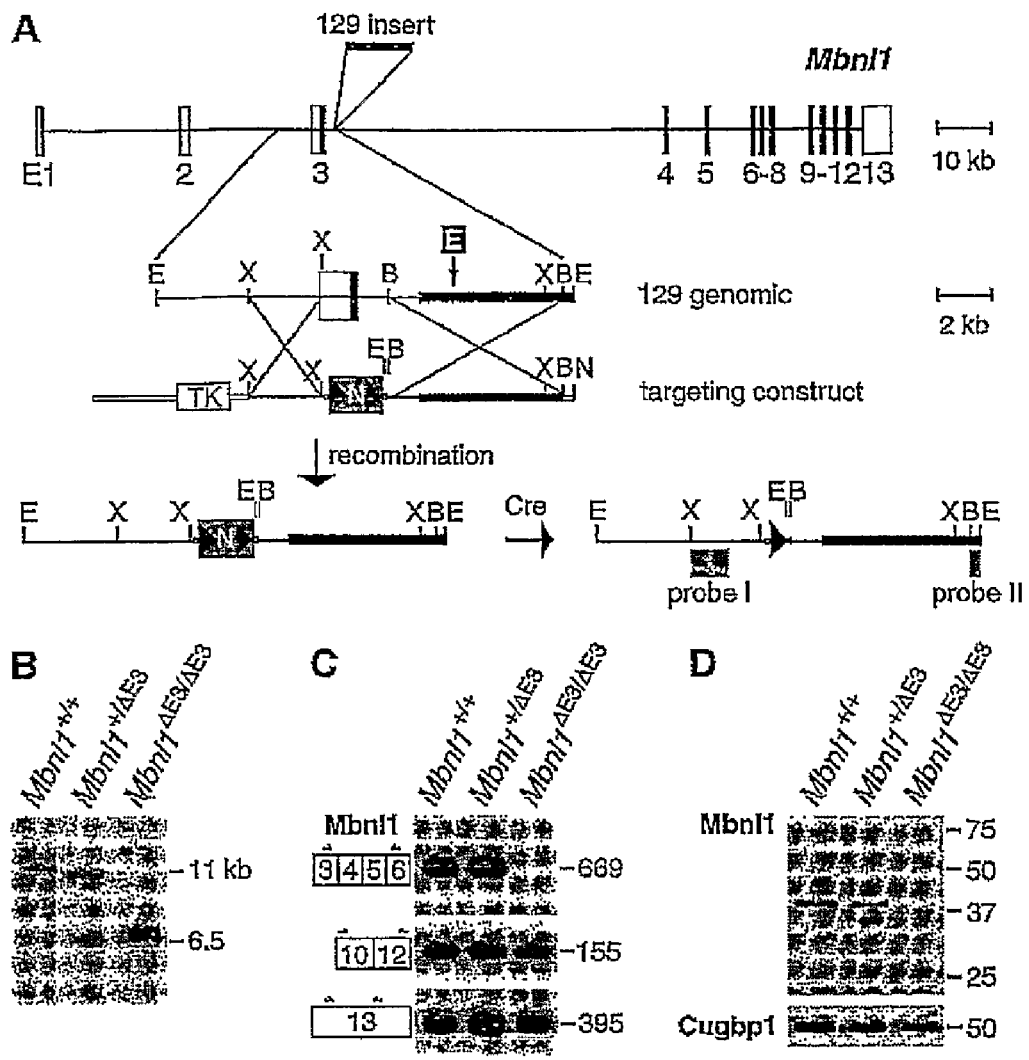
FIG. 1A shows targeted disruption of Mbnl1. The illustration includes C57BL/6J Mbnl1 exon organization (open boxes, UTRs black boxes, open reading frame) together with the 129S1/Svlm] insert (black rectangle), the 129 genomic region with EcoRV (E) (E site in C57BL/6] shown by black box with white E), Xba1 (X), and Bam HI (B) sites, the targeting construct with a thymidine kinase marker (TK), floxed (black triangles, loxP sites), neomycin cassette (stippled box with white N), the 129 region (thick black line) and locations of hybridization probes I and II.
FIG. 1B is a genomic analysis of Mbnl1 mice with the use of probe 1. The 11-kb EcoRV fragment is derived from C57BL/6; the mutant is 6.5 kb.
FIG. 1C shows loss of Mbnl1 E3 expression in Mbnl1$^{\Delta E3/\Delta E3}$
FIG. 1D is an immunoblot analysis (total spleen protein) showing absence of Mbnl1 41-42 kD proteins in Mbnl1$^{\Delta E3/\Delta E3}$.

Proteins in the muscleblind-like (MBNL) family bind to expanded CUG repeats in vitro and colocalize with mutant DM and HSA$^{LR}$ transcripts in vivo. Human muscleblind genes MBNL1 (SEQ ID NO: 1), MBNL2 (SEQ ID NO: 2), and MBNL3 (SEQ ID NO: 3) are homologous to the *Drosophila* gene muscleblind, which is essential for muscle and eye differentiation. MBNL1, the major MBNL gene expressed in human skeletal muscle, encodes multiple protein isoforms, including some that bind to expanded CUG repeats (41 to 42 kD) and others that fail to bind (31 kD isoform), generated by exon 3 skipping.

In fact, MBNL1 was identified in HeLa cells based on its ability to bind double-stranded CUG repeats (Miller J W, Urbinati C R, Teng-Umnuay P, Stenberg M G, Byrne B J, Thornton C A, Swanson M S (2000), *EMBO J* 19: 4439-4448). All three MBNL gene products colocalize with the expanded repeat RNA foci in vivo (Fardaei M, Rogers M T, Thorpe H M, Larkin K, Hamshere M G, Harper P S, Brook J D (2002), *Hum Mol Genet* 11: 805-814). Loss of MBNL function due to sequestration on CUG repeat RNA is proposed to play a role in DM pathogenesis (Miller J W, Urbinati C R, Teng-Umnuay P, Stenberg M G, Byrne B J, Thornton C A, Swanson M S (2000), *EMBO J* 19: 4439-4448). Thus, while expression of CUG and CCUG expansion RNAs induces MBNL recruitment into nuclear RNA foci, there is no evidence that this relocalization results in muscleblind depletion and functional impairment.

Recombinant Adeno-Associated Vectors

Recombinant AAV (rAAV) vectors have been used for expressing gene products in animals, see, for example, U.S. Pat. No. 5,193,941 and WO 94/13788. Other patents and publications describe AAV vectors and uses, the uses generally being related to expression of gene products either in vitro (usually tissue cultures) or in vivo (usually in the lungs or oral mucosa, the normal sites of AAV infection, but expression in other tissues, such as the central nervous system and in cardiac tissue has been observed).

AAV vectors have certain advantages over other well-characterized vector systems. First, like adenovirus, AAV infects non-dividing cells. Second, all the AAV viral genes are eliminated in the vector. Since the viral gene expression-induced immune reaction is no longer a concern, AAV vectors are safer than adenovirus vectors. As AAV is an integration virus, integration into the host chromosome will maintain the transgene in the cells. AAV is an extremely stable virus, resistant to many detergents, pH changes and heat (stable at 56° C. for about an hour). AAV can be lyophilized and redissolved without losing significant activity. Finally, AAV causes no known diseases or pathogenic symptoms in humans. Therefore, AAV is a very promising delivery vehicle for gene therapy.

Transduction of rAAV vectors harboring the bacterial β-galactosidase gene by single injection into the quadriceps of mice demonstrated that expression was maintained long-term and the expression did not decrease substantially during that time (Xiao et al., J. Virol., 70:8098-8108 (1996)). Other targets successfully transduced with rAAV vectors include: T-lymphocytes and B-lymphocytes, human erythroleukemia cells, different regions of the rat brain, the striatum of the rat brain in a Parkinson's Disease model with the tyrosine hydroxylase gene, heart of the pig and rat with the LacZ gene, the peripheral auditory system of the guinea pig and bronchial epithelia of the rabbit and monkey.

EMBODIMENTS OF THE INVENTION

In one embodiment, the invention provides a vector for effective expression of a protein with MBNL1, MBNL2, or MBNL3 (or combinations thereof) function to treat conditions associated with aberrant microsatellite expansions. In an additional embodiment, the vector of the invention is recombinant adeno-associated virus (rAAV) vectors. In one embodiment of the invention, the rAAV contains a transgene that expresses an MBNL1, MBNL2, or MBNL3 (or combinations thereof) protein. In an additional embodiment, the invention provides a rAAV containing a transgene that expresses MBNL1 (for example, the 41 kD isoform).

Isolation of the DNA encoding MBNL polypeptides allows one to use methods well-known to the person of ordinary skill in the art to make changes in the codons for specific amino acids such that the codons are "preferred usage" codons for a given species.

In one embodiment, the rAAV of the invention includes a promoter, which directs the initiation of RNA transcription in the cell of interest. The promoter may be constitutive or regulated. Regulated promoters include inducible promoters and repressible promoters. In an additional embodiment of the invention, the regulation of the promoter is associated with an "operator", to which an inducer or repressor binds. The promoter may be a "ubiquitous" promoter active in essentially all cells of the host organism or may be a promoter with expression more or less specific to the target cells. Known strong promoters that find common use to obtain high levels of recombinant protein expression include the herpes simplex thymidine kinase promoter, SV40 promoter and LTRs such as that obtained from Moloney leukemia retrovirus. For the gene to be expressed, the coding sequence must be operably linked to a promoter sequence functional in the target cell.

It is not necessary that the AAV-derived sequences correspond exactly with wild-type AAV prototypes. For example, in one embodiment, the rAAV vectors of the invention may feature modified inverted terminal repeats and other sequences, provided that the rAAV vectors can replicate and be packaged with the assistance of helper virus, and establish a nonpathogenic latent infection in target cells. Typically, because of the packaging limitations of AAV, the polynucleotides encoding MBNL1 domain sequences and the regulatory elements can have a length of up to about 5,500 bases.

Numerous applications of the present invention, e.g., making transgenic constructs, involve the cloning, synthesis, maintenance, mutagenesis, and other manipulations of nucleic acid sequences that can be performed using routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

For propagation of the rAAV vectors in vitro, susceptible cells are co-transfected with an AAV-derived vector DNA and a suitable AAV-derived helper virus or plasmid harboring the AAV rep gene, AAV cap gene or both and infected by a helper virus, including herpesvirus, adenovirus or a suitable non-AAV helper plasmid using any number of transfection methods, including, inter alia, calcium-phosphate transfection, lipofection or other techniques known to those skilled in the art. The ratio of helper plasmids to the quantity of vector plasmid containing the gene of interest range from 1:1-1:10. This procedure produces recombinant AAV vectors; the vector plasmid contains the recombinant AAV genome flanked by the AAV ITRs. The AAV-derived helper virus or helper plasmid may be any virus or plasmid which is capable, on expression of the AAV genes it carries, of providing proteins necessary for the replication and packaging of the rAAV vector in a suitable host cell, for the purpose of producing rAAV vector stock.

In one embodiment, the target cells of the rAAV vectors of the invention are cells capable of expressing polypeptides with MBNL1 activity. In another embodiment of the invention, the cells are normal cells cultured in vitro. In further embodiments, the target cells of the rAAV vectors of the invention are human cells, or cells of other mammals, such as nonhuman primates and mammals of the orders Rodenta (mice, rats, rabbit and hamsters), Carnivora (cats and dogs) and Arteriodactyla (cows, pigs, sheep, goats and horses). In one embodiment of the invention, the cells are part of a living mammal at the time the rAAV vectors are delivered to the cell. The mammal may be at any stage of development at the time of delivery, e.g., embryonic, fetal, infantile, juvenile or adult. Additionally, the cells may be healthy or diseased.

In one embodiment, the rAAV vectors of the invention may be administered as viral particles alone, whether as an in vivo direct delivery to the vasculature or as an ex vivo treatment comprising administering the rAAV vector viral particles in vitro to cells from the animal receiving treatment followed by introduction of the transduced cells back into the donor. Alternatively, the rAAV vector virus particles can be used to transduce cells in conjunction with secondary agents known to enhance the efficiency of transduction, see, e.g., WO Ser. No. 95/33824 for a variety of secondary agents. The effective amount of rAAV vectors to be administered will vary from patient to patient. Accordingly, effective amounts are best determined by the physician administering the rAAV vectors, and appropriate dosages can be determined readily by one of ordinary skill in the art.

In one embodiment, the rAAV construct of the invention expresses human MBNL1 (rAAV-MBNL1 (rAAV-MBNL1/41)). In an additional embodiment of the invention, injection of the rAAV-MBNL1/41 into the tibialis anterior (TA) muscles of a transgenic model for DM that expresses a human skeletal α-actin transgene carrying 250 CTG repeats ($HSA^{LR}$—a mouse model which develops myotonia and muscle degeneration similar to muscle abnormalities seen in DM patients) results in a functional reversal of a DM-related phenotype, namely, reversal of mis-splicing of the Clcn1 skeletal muscle chloride channel, which results in myotonia.

In one embodiment, the invention is directed to methods for treating or preventing various disorders and conditions associated with aberrant microsatellite expansions in a mammal, said method comprising administering to the mammal a therapeutically effective amount of rAAV containing a transgene that encodes a protein selected from the group consisting of MBNL1, MBNL2, MBNL3, and combinations thereof. In a further embodiment of the invention, the protein is MBNL1. In another embodiment of the invention, the mammal is a human. In another embodiment, the transgene is human. In one embodiment of the invention, the disease associated with aberrant microsatellite expansion is a neurological or neuromuscular disease. In an additional embodiment of the invention, the disease is myotonic dystrophy. In yet another embodiment of the invention, the disease is SCA8.

In additional embodiments, the present invention provides methods for treating or preventing a disease or condition related to any physiological process affected by MBNL1, said method comprising administering to the mammal a therapeutically effective amount of rAAV containing a transgene that expresses the MBNL1 protein.

In one embodiment, the invention is directed to methods for treating or preventing various disorders and conditions associated with aberrant microsatellite expansions in a mammal, said method comprising administering to the mammal a therapeutically effective amount of rAAV containing a transgene that encodes a protein selected from the group consisting of MBNL1, MBNL2, MBNL3, and combinations thereof, wherein treating comprises reversing the mis-splicing of the Clcn1 skeletal muscle chloride channel.

In another embodiment of the invention, treating comprises reversing the mis-splicing of the Amyloid beta (A4) precursor protein (APP). The mis-splicing may correspond to alternative splicing of exon 7. In another embodiment of the invention, treating comprises reversing the mis-splicing of the NMDA receptor NR1 (GRIN1). The mis-splicing may correspond to alternative splicing of exon 5. In yet another embodiment of the invention, treating comprises reversing the mis-splicing of the Microtubule-associated protein tau (MAPT). The mis-splicing may correspond to alternative splicing of exon 2. In yet another embodiment of the invention, treating comprises reversing the mis-splicing of the TNNT2 (cTNT). The mis-splicing may correspond to alternative splicing of exon 5.

In one embodiment, the invention is directed to methods for treating or preventing various disorders and conditions associated with aberrant microsatellite expansions in a mammal, said method comprising administering to the mammal a therapeutically effective amount of rAAV containing a transgene that encodes a protein selected from the group consisting of MBNL1, MBNL2, MBNL3, and combinations thereof, wherein the mammal has RNA inclusions in neuronal cells.

One embodiment of the invention is directed to a pharmaceutical composition comprising rAAV containing a transgene that encodes at least one protein selected from the group consisting of MBNL1, MBNL2, MBNL3, and combinations thereof. In one embodiment of the invention, the protein is MBNL1. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., Remington's Pharmaceutical Sciences, 17.sup.th ed. 1985).

Formulations for both ex vivo and in vivo administrations include suspensions in liquid or emulsified liquids. The active ingredient (rAAV vector) is often mixed with excipients that are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, intravesically or intrathecally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention is often varied to assess the effect of various concentrations of a compound on a transgenic animal. The dose will also be determined by, e.g., the body weight or surface area of the area to be exposed to the compound. In general, the dose equivalent of a modulator is from about 1 ng/kg to 10 mg/kg for a typical subject. Administration can be accomplished via single or divided doses.

Pharmaceutical preparations of the disclosed gene vectors may be administered intravenously, parenterally or intraperitoneally. Solutions of pharmaceutically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations will contain a preservative to prevent growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier may be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, such as, parabens, chlorobutanol, phenol, sorbic acid, thimerosal, and the like. In many cases, it will be preferable to include isotonic agents, for example, sugars or sodium chloride.

Solutions of the AAV vector as a free acid (DNA contains acidic phosphate groups) or a pharmacologically acceptable salt can be prepared in water suitably mixed with a surfactant such as hydroxypropylcellulose. A dispersion of AAV particles also can be prepared in glycerol, liquid polyethylene glycols and mixtures thereof and in oils. Under ordinary conditions of storage and use, the preparations contain a preservative to prevent the growth of microorganisms. The sterile aqueous media employed are obtainable by standard techniques well known to those skilled in the art.

Prolonged absorption of the injectable compositions can be brought about by the use in the compositions of agents delaying absorption, for example, aluminum monostearate and gelatin. Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The composition can be formulated in a neutral or salt form. Pharmaceutically-acceptable salts, include the acid addition salts (formed with the free amino groups of the protein) and which are formed with inorganic acids such as, for example, hydrochloric or phosphoric acids, or such organics acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The pharmaceutical forms suitable for parenteral administration include sterile aqueous solutions or dispersions and sterile powders for the extemporaneous preparation of sterile injectable solutions or dispersions. In all cases the form must be sterile and must be fluid to the extent that parenteral administration is possible. The formulation must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile parenteral formulations are prepared by incorporating the AAV vector in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and freeze drying which yield a powder of the active ingredient plus any additional desired ingredient from the previously sterile-filtered solution thereof.

The rAAV containing a transgene that expresses the MBNL1 protein may, for example, be prepared by: culturing a composition comprising cells transiently transfected with an AAV helper plasmid comprising AAV rep and cap nucleic acid sequences encoding AAV rep and cap proteins, an adenoviral helper plasmid comprising essential adenovirus helper genes selected from the group consisting of E1A, E1B, E2A, E4, E4O RF6, E4O RF6/7, VA, and combinations thereof, and an AAV vector comprising first and second AAV ITRs flanking a DNA sequence encoding MBNL1 polypeptide, said sequence being operably linked to a promoter DNA sequence, in the absence of adenovirus particles and under conditions suitable for production of recombinant AAV, and purifying rAAV therefrom.

In one embodiment, the invention is directed to a transgenic animal having a substantial deletion of one or more MBNL1 exon(s). The transgenic animals of the invention can be any mammal other than humans. In one embodiment, the mammal is a rodent. In another embodiment of the invention, the rodent is a mouse. An additional embodiment is directed to a cell isolated from the transgenic animal of the invention.

In a further embodiment, the transgenic animal of the invention has a substantial deletion of Mbnl1 exon 3. In one embodiment, Mbnl1 exon 3 in the transgenic animal of the invention is deleted in its entirety.

In one embodiment of the invention, the transgenic mouse having a substantial deletion of Mbnl1 exon 3 constitutes an animal model for microsatellite expansion disease in mammals. In another embodiment of the invention, the mammal is a primate. In yet another embodiment of the invention, the primate is a human.

In one embodiment of the invention, the microsatellite expansion disease is caused by a microsatellite expansion in a coding region of DNA. In another embodiment of the invention, the microsatellite expansion disease is caused by a microsatellite expansion in a non-coding region of DNA. In one embodiment of the invention, the disease associated with aberrant expansion of microsatellites is myotonic dystrophy. Accordingly, in one embodiment of the invention, the mouse Mbnl1 gene knockout model exhibits myotonia and ocular cataracts.

In one embodiment, the invention is directed to a mouse model for disease associated with aberrant microsatellite expansion, comprising a mouse having a substantial deletion of Mbnl1 exon 3 (E3) in the mouse genome, wherein said mouse exhibits symptoms typical of a disease associated with aberrant microsatellite expansion in humans, wherein said mouse has loss of functional ClC-1 protein. In another embodiment of the invention, mouse has loss of functional Amyloid beta (A4) precursor protein. In another embodiment of the invention, the mouse has loss of functional NMDA receptor NR1. In yet another embodiment of the invention, the mouse has loss of functional Microtubule-associated protein tau. In another embodiment of the invention, the mouse has loss of functional TNNT2 protein. In another embodiment of the invention, the mouse has loss of functional TNNT3 protein.

One embodiment is directed to methods for preparing the transgenic animals of the invention. The transgenic animal of the invention may, for example, be prepared by transfecting a plurality of mouse embryonic stem cells with a nucleic acid comprising an MBNL1 gene with a substantial deletion of exon 3, selecting for transgenic embryonic stem cells having incorporated said nucleic acid into their genome, introducing at least one of said transgenic embryonic stem cells into an embryo to produce a chimeric mouse comprising at least one of said transgenic embryonic stem cells, breeding said chimeric mouse with a wild-type mouse to obtain F1 progeny heterozygous for the MBNL1 gene with a deletion of exon 3, and breeding a male mouse of said F1 progeny with a female mouse of said F1 progeny to obtain F2 progeny homozygous for MBNL1 gene with a deletion of exon 3, wherein the said mouse exhibits a phenotype indicative disease associated with aberrant microsatellite expansion, for example, myotonic dystrophy.

Additional embodiments are directed to methods for using the transgenic animals of the invention as animal models to study MBNL1 function in vivo, and for evaluating side effects of MBNL1-inhibiting compounds. For example, if a compound known to inhibit MBNL1 is administered to an MBNL1 knockout mouse, any detected effects of the compound on the mouse can be concluded to be MBNL1-independent.

In further embodiments, the transgenic mammals of the invention, and cells thereof, can be used as animal models to identify compounds useful in the treatment of diseases associated with aberrant microsatellite expansions (such as, in one embodiment, myotonic dystrophy) and to assess the functional effect of a test compound on cells or animals afflicted with such disease. Such compounds can be any small chemical compound, including polypeptides, polynucleotides, amino acids, nucleotides, carbohydrates, lipids, or any other organic or inorganic molecule. Alternatively, the compounds can be genetically altered versions of the MBNL1 gene.

In one embodiment of the invention, assessing the effects of a compound on cells or animals, e.g., the transgenic animals of the invention having a substantial deletion of MBNL1 exon 3, involves providing a combinatorial chemical or peptide library containing a large number of potential therapeutic compounds (potential modulator or binding compounds). Such "combinatorial chemical libraries" are then screened in one or more assays to identify those library members (particular chemical species or subclasses) that display as desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) Int. J. Pept. Prot. Res., 37:487-493 and Houghton, et al. (1991) Nature, 354:84-88).

To assess the effect of a compound on an animal, or to treat or prevent a condition associated with aberrant microsatellite expansion, for example, myotonic dystrophy, in an animal, administration of the compound can be achieved by any of the routes normally used for introducing a compound into ultimate contact with the tissue to be treated. The compounds are administered in any suitable manner, optionally with pharmaceutically acceptable carriers. Suitable methods of administering such compounds are available and well known to those of skill in the art, and, although more than one route can be used to administer a particular composition, a particular route can often provide a more immediate and more effective reaction than another route.

Although MBNL1 is referred to in the individual descriptions of the embodiments of the invention, MBNL2 and MBNL3 may likewise be contemplated for each embodiment.

Definitions

A "transgene" refers to genetic material that is introduced, or is capable of being introduced, into cells of a host animal. Typically, once a "transgene" is introduced into the cells of the host animal, it is maintained, either transiently or permanently, by, e.g., insertion into the host genome. In preferred embodiments of the present invention, a transgene is inserted into the host genome by homologous recombination, thereby replacing the endogenous gene with the transgene. Often, a transgene contains a coding sequence, operably linked to a promoter, that encodes a protein, e.g., a marker protein that allows the detection of the transgene in the cell. "Transgenic" refers to any cell or organism that comprises a transgene.

A "host" animal or mammal refers to any animal that is used to practice the herein-described methods, i.e. animals into which a transgene is introduced to disrupt an endogenous MBNL1 gene. For use in the present invention, such animals include any non-human mammals including, but not limited to, mice, rats, rabbits, and hamsters.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA and nucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical."

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein For example, polyclonal antibodies raised to an MBNL1 polypeptide from specific species such as rat, mouse, or human can be selected to obtain only those polyclonal antibodies that are specifically immunoreactive with the MBNL1 protein and not with other proteins, except for polymorphic variants and alleles of the MBNL1 protein.

The term "transduction" refers to the introduction of foreign DNA into cells of an organism (in vivo).

The term "transfection" refers to the introduction of foreign DNA into cells in culture (in vitro). Genetic modification of eukaryotic cells by introduction of foreign DNA using chemical means. In transient transfection, expression occurs from unintegrated foreign DNA and can be detected for a few days after transfection.

The term "titer" refers to the number of virus particles produced per ml. The assay system to determine the number of virus particles produced varies considerably depending on the virus in question. High titers are generally essential for successful gene therapy since they allow introduction of the therapeutic gene carried by the virus into the maximum number of cells.

The terms "treating" and "treatment" as used herein include any treatment of a condition or disease in a subject, and include inhibiting the disease or condition, (i.e. arresting its development), relieving the disease or condition (i.e. causing some degree of regression of the condition or delaying progression in the disease), or relieving (to some degree) the conditions caused by the disease (i.e. symptoms of the disease).

The term "vector" refers to a vehicle, usually a biological entity, such as a virus, used for the delivery of genes into an organism. A reagent that facilitates the introduction of foreign genes into cells.

The phrase "packaging cells" refers to cells that have been transfected with plasmids containing the cap and rep genes from AAV.

As used herein, "pharmaceutically acceptable carrier" includes any and all solvents, dispersion media, coatings, antibacterial and antifungal agents, isotonic and absorption delaying agents and the like. The use of such media and agents for pharmaceutically-active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A "substantial" deletion of exon 3 signifies a deletion extensive enough to lend to the phenotype indicative of a disease associated with aberrant microsatellite expansion.

Use of the terms "an", "a" and "the" and similar terms used in claiming or describing the invention are intended to be construed as including both the singular and plural, unless clearly otherwise indicated or contraindicated. The terms "including", "having" and "containing" are to be construed as open-ended in the same manner as the terms "comprising" or "comprises" are commonly accepted as including but not limiting to the explicitly set forth subject matter. The term "comprising" and the like are construed to encompass the phrases "consisting of" and "consisting essentially of".

The methods and processes described herein may be performed in any suitable order unless otherwise indicated or clearly rendered inoperable by a modification in order.

Limited and narrow interpretation of descriptive language intended to better illustrate the invention is not to be construed as limiting in any way nor to limit the scope of the invention contemplated by the inventors.

The invention, now described generally and in some detail, will be understood more readily by reference to the following examples, which are provided by way of reference and are in no manner intended to limit the scope of what the inventors regard as their invention.

EXAMPLES

Example 1

Characterization of Mbnl1$^{\Delta E3/\Delta E3}$ Mice

Targeted disruption of Mbnl1: to test whether or not sequestration of MBNL proteins contributes to DM pathogenesis, mice with a targeted deletion of MbnlI exon 3 (E3) (FIG. 1A) were generated. The pMbnl1$^{\Delta E3neo}$ targeting plasmid was constructed using pTKflNeo (gift of E. Scott, University of Florida), which contains the Herpes simplex virus-thymidine kinase (HSV-TK) negative selection marker and a loxP-flanked phosphoglycerate kinaseneomycin (PGK-Neo) positive selection cassette. A 2.5 kb XbaI fragment (5' arm of homology) corresponding to the upstream region bordering Mhnl1 exon 3, was inserted 5' of PGK-Neo. For the 3' arm of homology, a 6 kb Mbnl1 BamHI fragment was subcloned into pBluescript II KS+ (Stratagene, La Jolla, Calif.), excised with XhoI/NotI, and cloned into the XhoI/NotI sites of pTKflNeo 3' of PGK-Neo.

The pMbnl1$^{\Delta E3neo}$ plasmid was linearized with NotI and electroporated into CJ.7 ES cells (P. J. Swiatek, T. Gridley, *Genes & Dev.* 7, 2071 (1993)). ES cells were cultured and selected as described in T. Yang et al., *Nat. Genet.* 19, 25 (1998). Clones resistant to G418 and FIAU were isolated and screened for homologous recombination by utilizing a forward primer (5'-TGGGATGGAATTGTGGTGTGTTGT-TGCTCATG-3') (SEQ ID NO: 4) outside the 5' homologous region and a reverse primer (5'-TCCATTTGTCACGTCCT- GCACCGACGC-3') (SEQ ID NO: 5) in PGKNeo. Amplification (25 cycles) consisted of 98° C. for 20 s followed by 68° C. for 4 min. Targeted ES cell clones yielded a 2.9 kb PCR product. This targeting strategy was predicted to approximate the situation in DM by eliminating synthesis of CUG-binding isoforms (Miller, et al, 2000).

Genomic DNA analysis of Mbnl1 mice: genomic blot analysis demonstrated successful deletion of Mbnl1$^{\Delta E3/\Delta E3}$ mice (FIG. 1B). Five ES cell clones (35, 56, 92, 111, 120) that were positive for homologous recombination were confirmed by genomic DNA blot analysis. Based on restriction map analysis of genomic fragments flanking E3, ES genomic DNA digested with EcoRV produces a 16 kb band when a 300 nt Mbnl1 BamHI/EcoRV fragment outside the 3' arm of homology is used as a hybridization probe (probe II of FIG. 1A). In the targeted allele, a new EcoRV site (from pBluescript II KS$^+$) is introduced, generating a novel 6.7 kb EcoRV fragment. All five clones that were positive by PCR were also positive by genomic DNA blot analysis. When the 5' arm of homology (2.5 kb XbaI fragment) was used as probe, two bands at 16 kb (wild type) and 7.5 kb (mutant) were detected. To check for additional insertion events in these five clones, PGK-Neo fragment was used as probe on genomic DNA digested with EcoRV. A single band at 7.5 kb confirmed the absence of any additional insertion events.

One ES clone (ES.35) was expanded and transiently transfected with Crerecombinase to excise PGK-Neo. To detect PGK-Neo loss, forward (5'-CTACGATGGCTGGCTG-CAATATGCCTCACTGTAAG-3') (SEQ ID NO: 6) and reverse (5'-GGGTTGAATCTCGTTAGGGACACTGGGT-GTCTGTAA-3') (SEQ ID NO: 7) primers were used for a PCR screen. PCR was performed for 30 cycles, each cycle consisting of 96° C. for 30 see, 60° C. for 30 sec and 72° C. for 2 min. Clones positive for PGK-Neo deletion yielded a 1 kb band and cassette excision was confirmed by genomic DNA blot analysis. Utilization of a PCR-generated subfragment of the 5' arm of homology as a hybridization probe yielded EcoRV bands at 16 kb and 6.5 kb. The loss of PGK-Neo results in decrease in the size of the mutant allele digested with EcoRV from 7.5 to 6.5 kb. The Neo excised allele was designated Mbnl1$^{\Delta E3}$.

Two Mbnl1$^{+/\Delta E3}$ ES clones (1B3, 2C1) were transferred to 3.5 dpc C57BL/6J blastocysts which were then carried to term by B6D2F1/J recipients. One chimeric male was obtained from each clone. Contribution of CJ.7 (129S1/Sv-1mJ) ES cells to the germline was determined by mating the chimeric males with C57BL/6J females. Agouti pups in litters sired by the 1B3 chimeric male indicated germline transmission.

To detect heterozygotes in the F1 population derived from 1 B3, a combination of one forward primer (5'-CTACGATG-GCTGGCTGCAATATGCCTCACTGTAAG-3') (SEQ ID NO: 8) and two reverse primers [for the mutant allele (5'GGGTTGAATCTCGTTAGGGACACTGGGT-GTCTGTAA-3' (SEQ ID NO: 9)]; [for the wild-type allele (5'-TGGCAGACCCTTTGACACCG-3') (SEQ ID NO: 10)] were used for PCR. Amplification was performed for 30 cycles, each cycle consisting of 96° C. for 30 sec, 60° C. for 30 sec and 72° C. for 2 min. Heterozygotes were then mated to obtain Mbnl1$^{\Delta E3/\Delta E3}$ mice.

Loss of Mbnl1 E3 expression in Mbnl1$^{\Delta E3/\Delta E3}$: loss of E3 expression was confirmed by reverse transcription polymerase chain reaction (RT-PCR); primers in exons 3 and 6 were used to amplify a cDNA product from either Mbnl1$^{+/+}$ or Mbnl1$^{+/\Delta E3}$ mice that was absent in Mbnl1$^{\Delta E2/\Delta E3}$ mice (FIG. 1C). To confirm loss of exon 3, an RT-PCR strategy was used with the forward primer positioned in exon 3 (5'-TAGT-GTCACACCAATTCGGGACACAAA-3') (SEQ ID NO: 11) and an exon 6 reverse primer (5'CCCTTGATGTAATCCAT-GCAGACAGTGA-3') (SEQ ID NO: 12). Continued transcription of Mbnl1 in Mbnl1$^{\Delta E3/\Delta E3}$ lines was examined using exon 10 forward (5'-TGCACGGTGCTACGCCAGCC-3') (SEQ ID NO: 13) and exon 12 reverse (5'GTGACGA-CAGCTCTACATCTGGGTAACA-3') (SEQ ID NO: 14) primers, as well as exon 13 forward (5'-CCTGCTGCA-CACTGTTGCCTACAC-3') (SEQ ID NO: 15) and reverse (5'TGTCAGTTCCCTCCCTCACCATGT-3') (SEQ ID NO: 16) primers. For amplification, 27 cycles were performed each consisting of 45 sec at 95° C., 45 sec at 55° C. and 45 sec at 72° C., followed by a final 10 min extension at 72° C. As expected, Mbnl1 expression was not fully eliminated in Mbnl1$^{\Delta E3/\Delta E3}$ mice; RT-PCR products were apparent with primers in constitutively spliced exons 10 and 12, or within exon 13.

Immunoblot analysis (total spleen protein): for immunological detection of Mbnl1, tissues were placed in homogenization buffer (50 mM Tris-Cl [pH=8.0], 150 mM NaCl, 2 mM phenylmethylsulfonyl fluoride, 6 µg/ml aprotinin, 1 µg/ml leupeptin) and disrupted using a Polytron homogenizer and brief sonication (3×5 sec using a microtip sonicator). Following addition of IGEPAL CA-630 (Sigma) to 1%, homogenates were incubated on ice for 15 min, centrifuged at 16,000×g for 10 min. Proteins (30 µg per lane) were detected following SDS-PAGE and immunoblotting using anti-Mbnl1 mAb 3A4 (J. W. Miller et al., *EMBO J.* 19, 4439 (2000), A. Mankodi et al., *Ann. Neurol.*, in press). Total spleen was analyzed (FIG. 1D), because this tissue contains relatively high levels of both Mbnl1 and Cugbp1.

To confirm elimination of the Mbnl1 41- to 42-kD proteins in Mbnl1$^{\Delta E3/\Delta E3}$ mice, monoclonal antibody 3A4 was used, which recognizes Mbnl1 proteins containing exon 5[MS1]. The 41- to 42-kD isoforms in Mbnl1$^{+/+}$ and Mbnl1$^{+/\Delta E3}$ mice were missing in Mbnl1$^{\Delta E3/\Delta E3}$ (FIG. 1D). Previous studies suggested that elevated levels of another RNA-binding protein, CUGBP1, are responsible for DM-associated RNA splicing changes. However, Mbnl1$^{\Delta E3/\Delta E3}$ mice did not show increased CUGBP1 expression (FIG. 1D).

Example 2

Myotonia and Cataracts

Electromyography: electromyography was performed under general anesthesia (intraperitoneal ketamine, 100 mg/kg; xylazine, 10 mg/kg; and acepromazine, 3 mg/kg) using 30 gauge concentric needle electrodes to examine three hindlimb (tibialis anterior, gastrocnemius, vastus), two forelimb (flexor compartment of distal forelimb, triceps), and thoracolumbar paraspinal muscles. At least 10 needle insertions were performed in each muscle and myotonic discharges were graded on a 4 point scale: 0, no myotonia; 1, occasional myotonic discharge in <50% of needle insertions; 2, myotonic discharge with >50% of insertions; and 3, myotonic discharge with nearly all insertions. The mean score across all Mbnl1$^{\Delta E3/\Delta E3}$ limb muscles was 2.9 in mice age 7 to 11 weeks (n=10). Myotonic discharges were not observed in any muscle in heterozygous Mbnl1$^{+/\Delta E3}$ mice (n=9) or wild-type littermates (n=9).

Mbnl1$^{\Delta E3/\Delta E3}$ mice display overt myotonia beginning around 6 weeks of age. Delayed muscle relaxation was most noticeable after a period of rest and showed improvement during activity. A similar "warm up" phenomenon is characteristic of myotonia in human DM. Electromyographic recordings confirmed myotonic discharges in all Mbnl1$^{\Delta E3/\Delta E3}$ mice tested (n=10) (FIG. 2A).

ClC-1 splicing in DM mouse models: because myotonia in DM1 and DM2 muscle is associated with aberrant ClC-1 splicing, RT-PCR assays were used to investigate the effect of loss of Mbnl1 E3 on ClC-1 (encoded by Clcn1) expression (FIG. 2B). Total cellular RNA was extracted from either quadriceps or heart muscle of Mbnl1$^{+/+}$, Mbnl1$^{+/\Delta E3}$ and Mbnl1$^{\Delta E3/\Delta E3}$ mice by homogenizing the tissues in TRI-RE-AGENT (Sigma, St. Louis, Mo.) according to manufacturer's protocol. First strand cDNA was generated by reverse transcription (RT) using 5 μg of total RNA and SuperScript II RNase H$^-$ RT (Invitrogen, Carlsbad, Calif.) following the manufacturer's protocol. For subsequent PCR reactions, 20% of the RT reaction was used as template. Each PCR reaction was spiked with 10 μCi of ($\alpha^{32}$P)-dCTP (PerkinElmer Life Sciences, Boston, Mass.). PCR products were resolved on 5-8% non-denaturing polyacrylamide gels followed by autoradiography using Biomax MS film (Eastman Kodak, Rochester, N.Y.).

For ClC-1 mRNA analysis, the forward primer used corresponded to exon 5 (5'-GGAATACCTCACACTCAAG-GCC-3') (SEQ ID NO: 17) and the reverse primer to exon 8 (5'-CACGGAACACAAAGGCACTGAATGT-3') (SEQ ID NO: 18). PCR was performed for 27 cycles each consisting of 45 sec at 95° C., 45 sec at 55° C. and 45 sec at 72° C., followed by a final 10 min extension at 72° C. Full-length ClC-1 cDNA clones were generated from muscle RNA by RT-PCR as previously described (A. Mankodi et al., *Mol. Cell* 10, 35 (2002)). Sequence analysis of 10 clones from Mbnl1$^{\Delta E3/\Delta E3}$ mice revealed 6 clones with inclusion of exon 7a and 2 clones with retention of intron 2. All splice junctions were normal in 10 clones derived from wild-type littermates.

Remarkably, Mbnl1$^{\Delta E3/\Delta E3}$ mice showed abnormal inclusion of Clcn1 cryptic exons 7a and 8a in a pattern similar to that seen in HSA$^{LR}$ mice. Also, some full-length ClC-1 cDNA clones from Mbnl1$^{\Delta E3/\Delta E3}$ mice showed abnormal inclusion of intron 2, as has been observed in DM and HSA$^{LR}$ muscle. Notably, these abnormal splice isoforms have premature termination codons and do not encode functional chloride channels. By contrast, splicing of the Scn4a sodium channel, the only other ion channel previously associated with myotonia was normal in Mbnl1$^{\Delta E3/\Delta E3}$ muscle. These results suggested that changes in splice site selection result in the loss of functional ClC-1 from myofiber membranes.

ClC-1, Dys2, and α-sarcoglycan immunostaining: frozen sections of vastus (6 μm) were immunostained using polyclonal antibodies directed against the C-terminus of ClC-1 (Alpha Diagnostic, San Antonio) or monoclonal antibodies to dystrophin (Dys2) or a-sarcoglycan (NovoCastra, Newcastle upon Tyne) as described in A. Mankodi et al., *Mol. Cell* 10, 35 (2002).

Immunofluorescence analysis confirmed a major reduction of ClC-1 protein in Mbnl1$^{\Delta E3/\Delta E3}$ muscle relative to the muscle of wild-type sibs (FIGS. 2, C and D), whereas the membrane-associated proteins dystrophin (FIGS. 2, E and F) and α-sarcoglycan (FIG. 3) were unaffected. Because abnormalities of ClC-1 splicing in Mbnl1$^{\Delta E3/\Delta E3}$ muscle are more pronounced than in HSA$^{LR}$ muscle, and considering that HSA$^{LR}$ mice have a >80% reduction of chloride conductance, it is likely that myotonia in Mbnl1$^{\Delta E3/\Delta E3}$ mice is due to improper ClC-1 pre-mRNA splicing.

Analysis of muscle histology: frozen sections (10 μm) of vastus and gastrocnemius muscle were prepared for routine histologic (hematoxylin and eosin, modified Gomori trichrome, periodic acid-Schiff) and histochemical (cytochrome oxidase, acid phosphatase, nicotinamide adenine dinucleotide-tetrazolium reductase, myosin ATPase, succinate dehydrogenase) stains (V. Dubowitz, *Muscle Biopsy, A Practical Approach* (Bailliere Tindall, London, ed. 2, 1996)).

Figure 2:
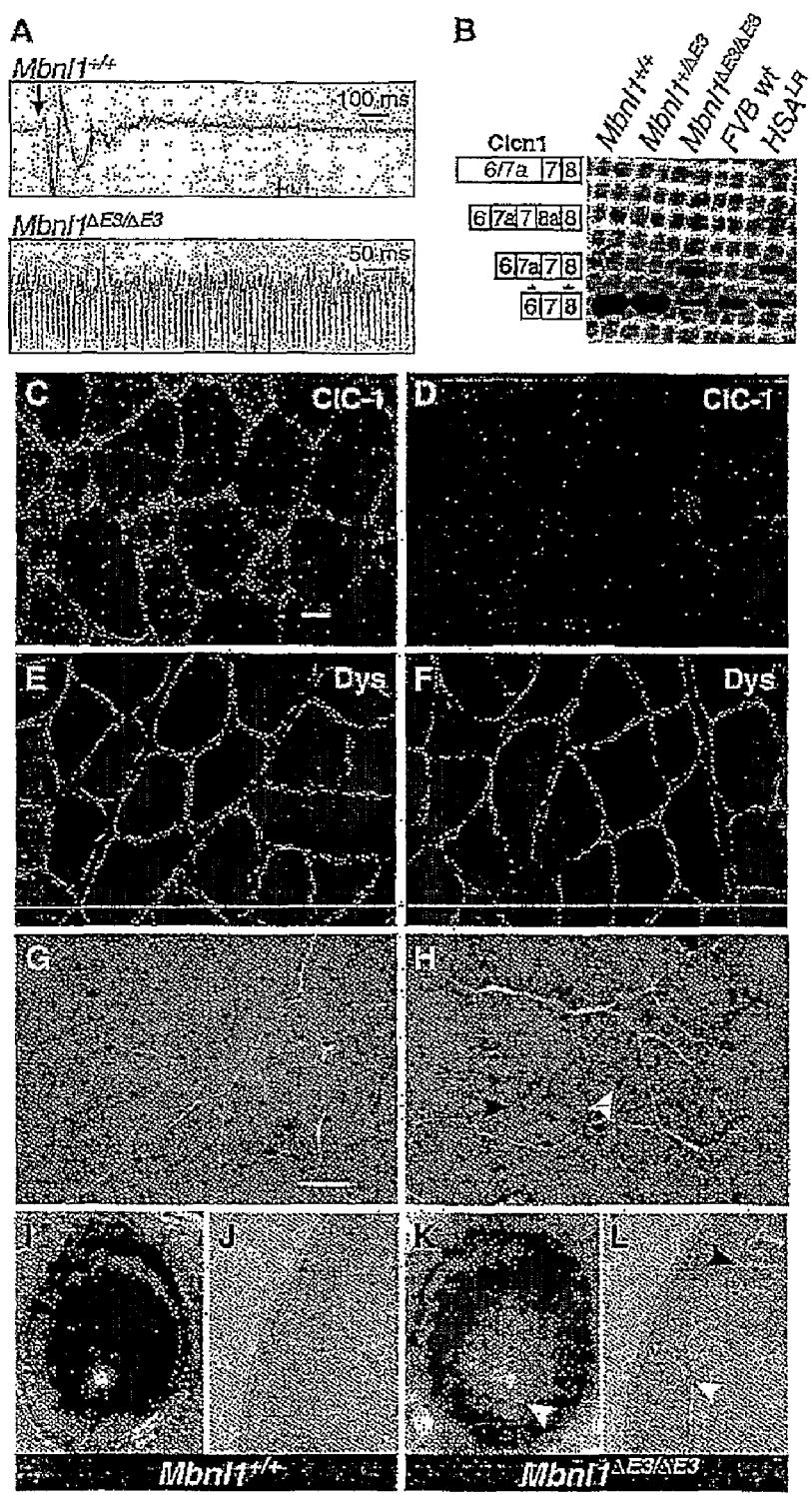
FIG. 2A shows an electromyograph (EMG) of Mbnl1 wild-type and mutant knockout vastus muscle. The arrow (top panel) indicates normal EMG electrode insertional activity in wild-type muscle, whereas insertion triggers myotonic discharges in Mbnl1$^{\Delta E3/\Delta E3}$ muscle (bottom panel).
FIG. 2B shows ClC-1 splicing in DM mouse models. Functional chloride channels are produced when Clcn1 exons 6, 7 and 8 are spliced directly together, whereas isoforms that include cryptic exons 7a or 8a encode truncated non-functional proteins. Clcn1 exons 7 to 8 are illustrated (open boxes) with the primer positions indicated via horizontal arrows. Inclusion of exons 7a and 8a occurs at low levels in wild-type (FVB wt, Mbnl1$^{+/+}$) and Mbnl1$^{+/\Delta E3}$ muscle but at increased levels in Mbnl1$^{\Delta E3/\Delta E3}$ and HSA$^{LR}$ muscle.
FIG. 2C and FIG. 2D depict the loss of ClC-1 protein observed in Mbnl1$^{\Delta E3/\Delta E3}$ vastus muscle. Representative images of sections from 11-week-old mice show reduced ClC-1 immunostaining in Mbnl1$^{\Delta E3/\Delta E3}$ mice (D) relative to wild-type mice (C). Scale bar, 20 μm.
FIG. 2E and FIG. 2F constitute representative images of sections from 11-week-old mice showing equivalent dystrophin (Dys) levels in Mbnl1$^{+/+}$ (E) and Mbnl1$^{\Delta E3/\Delta E3}$ (F) muscle.
FIG. 2G and FIG. 2H depict abnormal muscle histology. Hematoxylin and eosin (H&E)-stained vastus from wild-type (G) and Mbnl1$^{\Delta E3/\Delta E3}$ (H) mice, showing split myofibers (black arrowhead) and centralized myonuclei (white arrowhead). Scale bar, 30 μm.
FIG. 2I to FIG. 2L show cataract development. Dilated eyes of 18-week old mice showing a clear wild-type lens (I) but dust-like opacities (white arrowhead) in Mbnl1$^{\Delta E3/\Delta E3}$ mice (K). Center bright spot is the lamp reflection. H&E-stained anterior section (J, L) highlight increased fragmentation (black arrowhead) and opacities (white arrowhead) in Mbnl1$^{\Delta E3/\Delta E3}$ lens (L) compared to wild-type lens (J).
Figure 3:
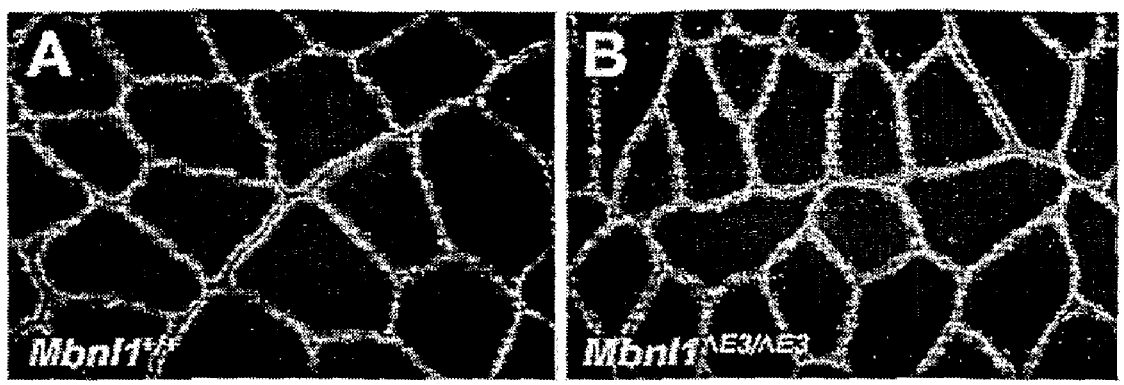
FIGS. 3A and 3B constitute representative images of sections from 11-week-old mice showing similar levels of α-sarcoglycan in (A) wild-type (Mbnl1$^{+/+}$) vastus muscle and (B) muscleblind E3 knockout (Mbnl1$^{\Delta E3/\Delta E3}$) vastus muscle.

Histological analysis of Mbnl1$^{\Delta E3/\Delta E3}$ mice up to 11 weeks of age did not show major degeneration of muscle fibers. Pathological features in Mbnl1$^{\Delta E3/\Delta E3}$ muscle included an increase in nuclei with an abnormal (central) position and splitting of myofibers (FIGS. 2, G and H). Histologic abnormalities were not observed in Mbnl1$^{+/+}$ or Mbnl1$^{+/\Delta E3}$ muscle.

Cataract development: besides muscle abnormalities, distinctive ocular cataracts that progress from subcapsular "dust-like" opacities to mature cataracts are a prominent DM-associated feature. Similar cataracts were observed in all Mbnl1$^{\Delta E3/\Delta E3}$ eyes examined (n=24; 3 to 8 months old) but not in wild-type siblings (FIG. 2, I to L).

For ocular lens evaluation, mice were sedated using intraperitoneal injection of 100 mg/kg ketamine (Ketaset, Fort Dodge, Iowa) and 10 mg/kg xylazine (Xylaject, Phoenix, St Joseph, Mo.) and anterior chambers and lenses were examined using a slit lamp (Haag Streit, Mason, Ohio). In vivo images were obtained using a Nikon 990 digital camera attached to the slit-lamp. Immediately after euthanasia, globes were enucleated, fixed in paraformaldehyde and embedded in paraffin blocks before being processed overnight in a Shandon Excelsior tissue processor (Thermo Electron, Waltham, Mass.). Sections (4 μm) were cut using an HM-315 microtome (Richard-Allan, Kalamazoo, Mich.), dried and H&E stained. Sections were photographed using a Canon EOS D60 digital camera attached to an Olympus Vanox microscope.

Example 3

Pre-mRNA Splicing

Abnormal regulation of alternative splicing—Tnnt2: abnormal regulation of alternative splicing has been observed in DM1 muscle for cardiac troponin T (TNNT2), insulin receptor (INSR), and ClC-1. Tnnt2 was analyzed using exon 2 forward (5'GCCGAGGAGGTGGTGGAGGAGTA-3') (SEQ ID NO: 19) exon 6 reverse (5'GTCTCAGCCTCAC-CCTCAGGCTCA-3') (SEQ ID NO: 20) and 27 PCR cycles (45 sec at 96° C., 45 sec at 58° C. and 45 sec at 72° C., followed by a final 10-min extension at 72° C.). Analysis of INSR is uninformative because human patterns of INSR alternative splicing are not conserved in mice. However, Mbnl1$^{\Delta E3/\Delta E3}$ adult heart shows abnormal retention of the Tnnt2 "fetal" exon 5 (FIG. 4A), as was observed for DM1.

Abnormal regulation of alternative splicing—Tnnt3: to determine whether alternative splicing of other genes is disrupted in Mbnl1$^{\Delta E3/\Delta E3}$, fast skeletal muscle troponin T (Tnnt3) was assessed. For mouse Tnnt3, the forward primer overlaps exons 2 and 3 (5'TCTGACGAGGAAACTGAA-CAAG-3') (SEQ ID NO: 21) while the reverse primer (5'TGT-CAATGAGGGCTTGGAG-3') (SEQ ID NO: 22) corresponds to exon 11. For human TNNT3, exon 2 forward (5'-TTCACCATGTCTGACGAGGAAG-3') (SEQ ID NO: 23) and exon 10 reverse (5'CTTCTGGGATCTTAGGAG-CAGTG-3') (SEQ ID NO: 24) primers were used. For mouse Tnnt3 and human TNNT3, 25 PCR cycles were performed each consisting of 45 sec at 95° C., 45 sec at 50° C. and 30 sec at 72° C., followed by a final 10-min extension at 72° C. The same amplification protocol was used to amplify the mouse Tnnt3 carboxyl terminal region using an exon 15 forward primer (5'-CCTTGTACCAACTGGAGACTGAC-3') (SEQ ID NO: 25) and an exon 18 reverse primer (5'-TGATG-GTCTCTGCTGCAGTG-3') (SEQ ID NO: 26).

Figure 4:
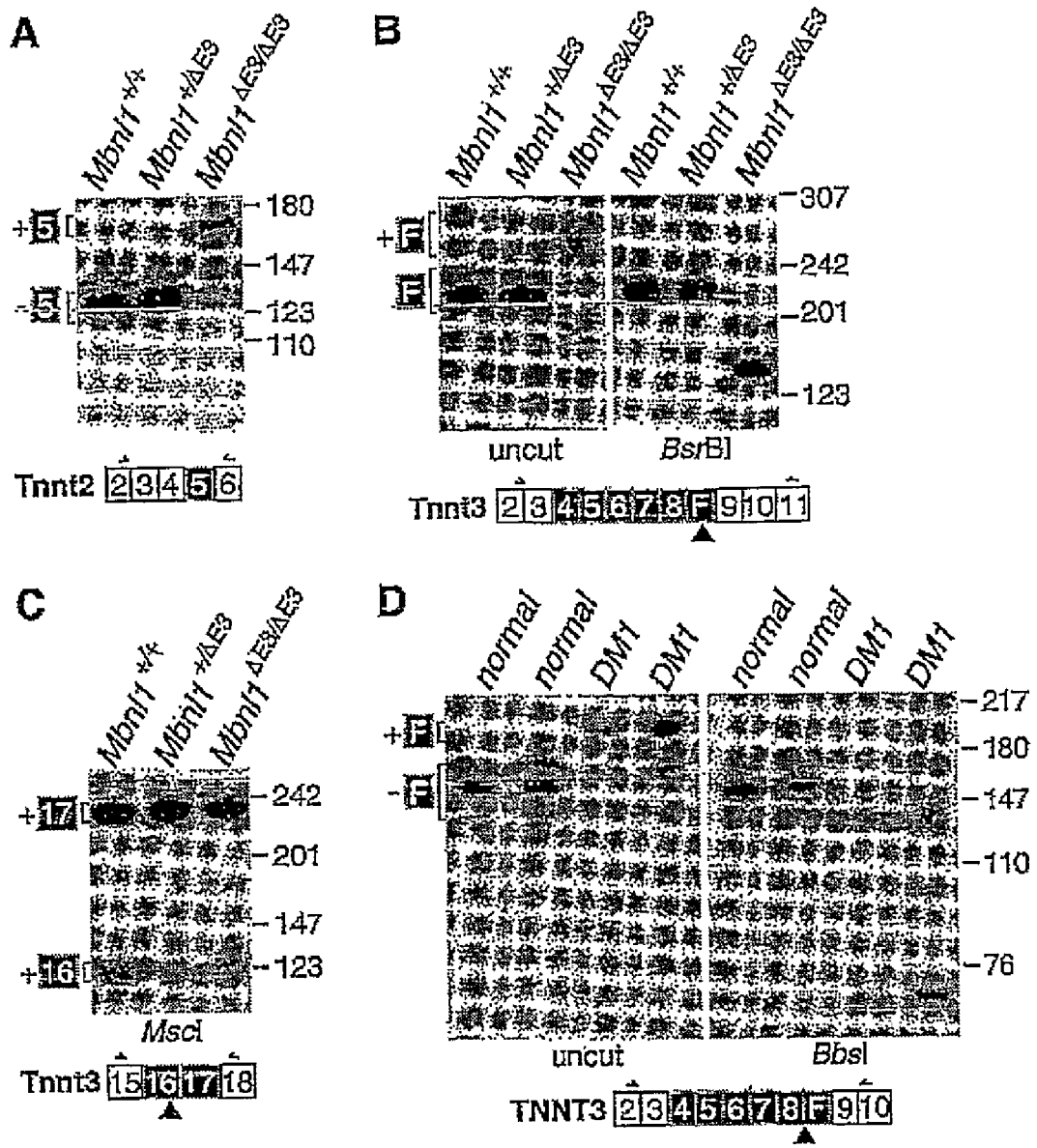
FIG. 4A shows adult retention of Tnnt2 exon 5 Mbnl1$^{\Delta E3/\Delta E3}$ heart. RT-PCR products with (+) and without (−) exon 5 (black box) are indicated (brackets). Size markers are pBR322 Msp I fragments.
FIG. 4B shows Tnnt3 fetal (F) exon inclusion in adult Mbnl1$^{\Delta E3/\Delta E3}$. The Tnnt3 protein contains variable N-terminal (alternative splicing of exons 4 to 8 and F) and C-terminal regions (exons 16 and 17) (23). RT-PCR (11-week-old mice) of Tnnt3 exons 2 to 11 (left panel) is shown with alternatively spliced exons 4 to 8 and the fetal (F) exon (black boxes). The F exon contains a BsrBI site (arrowhead) resulting in co-migrating smaller fragments in Mbnl1$^{\Delta E3/\Delta E3}$ (right panel).
FIG. 4C depicts RT-PCR of Tnnt3 exons 15 to 18 after MscI digestion.
FIG. 4D shows retention of Tnnt3 fetal (F) exon in adult DM1 skeletal muscle (left panel). The right panel shows cDNAs containing the F exon (bracket) cleaved with BbsI (arrowhead).

Primers in Tnnt3 exons 2 and 11 produced a single major RT-PCR product in adult Mbnl1$^{+/+}$ and Mbnl1$^{+/\Delta E3}$ mice that was undetectable in Mbnl1$^{\Delta E3/\Delta E3}$ mice (FIG. 4B). Instead, a cluster of larger cDNAs, all containing a "fetal" (F) exon, was prominent. In contrast, mutually exclusive splicing of Tnnt3 exons 16 and 17 was unaffected in Mbnl1$^{\Delta E3/\Delta E3}$ mice; this finding shows that altered Mbnl1 expression has specific effects on splice site selection even within the same pre-mRNA (FIG. 4C). Similar alterations of TNNT3 splicing in adult DM1 muscle (FIG. 4D) were found.

Abnormal regulation of alternative splicing—Scn4a: missense mutations in the Scn4a muscle-specific sodium channel are also associated with myotonia. The Scn4a pre-mRNA has two rare AT/AC splice sites but is not known to undergo alternative splicing. To screen for abnormalities of Scn4a splicing that might contribute to myotonia, RT-PCR analysis of muscle RNA was carried out. Partial cDNAs covering the entire Scn4a coding region (GenBank accession #AJ278787) were generated by PCR using the following primers: set 1 exon 1 (GACCTGGAAGCTGGCAAGAAC) (SEQ ID NO: 27) to exon 6 (TCCCTTCGTCATTGATGTAGGC) (SEQ ID NO: 28); set 2 exon 6 (CCATGAATGACACCAACACCAC) (SEQ ID NO: 29) to exon 12 (CTGAGGGTGACGAT-GAAGCTG) (SEQ ID NO: 30); set 3 exon 12 (TCT-TCACGGGCATCTTCACTG) (SEQ ID NO: 31) to exon 17 (CGCCGCTGTTCAATGTAGATG) (SEQ ID NO: 32); and set 4 exon 16 (TGCCTCTATGTGGACATCTCCC) (SEQ ID NO: 33) to exon 24 (CGACTCTTTCTTGACGTAGGCG) (SEQ ID NO: 34). RT-PCR products from primer sets 1, 2, 3, and 4 was analyzed on 1% agarose gels before and after restriction digest with ApaI, NcoI, BspEI and BsrGI-HindIII, respectively. Results showed no difference in the length of Scn4a cDNA fragments in Mbnl1$^{+/+}$, Mbnl1$^{+/\Delta E3}$, $^{Mbnl1}$1$^{\Delta E3/\Delta E3}$ or HSA$^{LR}$ mice (data not shown).

Loss of specific Mbnl1 isoforms that associate with expanded (CUG)$_n$ and (CCUG)$_n$ RNAs is sufficient to cause myotonia, cataracts, and RNA splicing defects that are similar to those seen in DM. Although muscleblind-like proteins may influence gene expression at multiple levels, these proteins may play a direct role in splice site selection. Recent co-transfection analysis in HEK293 cells using a Tnnt3 minigene indicated that the Mbnl1 41 kDa protein regulates alternative splice site choice by binding to a discrete RNA element upstream of the fetal (F) exon. Thus, MBNL proteins bind to distinct RNA sequence elements and influence exon use during splicing.

Young Mbnl1$^{\Delta E3/\Delta E3}$ mice do not develop the severe neo-natal muscle weakness associated with congenital DM1, and it is not yet known whether cardiac conduction problems develop in this model. Thus, some aspects of the DM phenotype may not result from loss of MBNL1 function alone. Additional muscleblind proteins (MBNL2 and MBNL3) are also recruited to nuclear RNA foci. It is contemplated that their sequestration may be required to fully replicate the multisystemic DM phenotype.

Example 4

AAV-MBNL1 Injection and Clcn1 Splicing

Figure 5A:
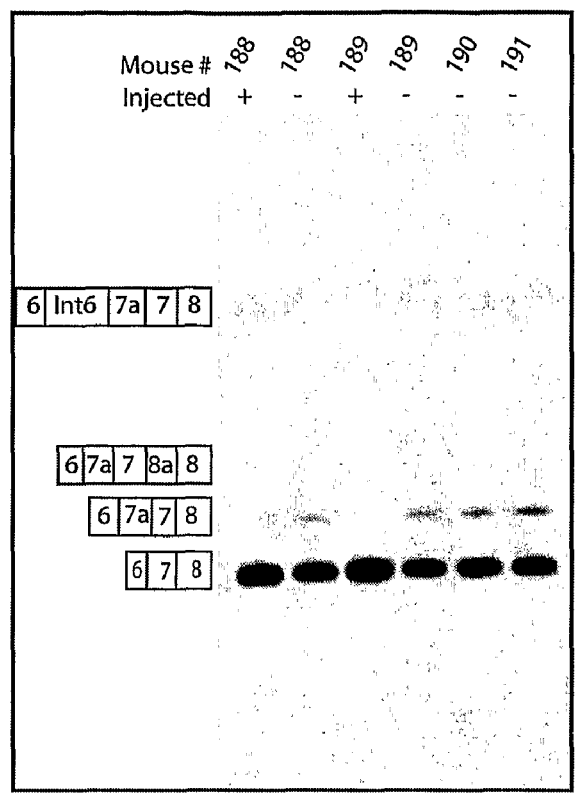
FIG. 5A shows reversal of the skeletal muscle major chloride channel (Clcn1) splicing defect following AAV-MBNL1 injection. +lanes represent AAV-mycMBNL1 injection into the Tibialis anterior (TA) muscles of $HSA^{LR}$ mice, while −lanes represent injection of PBS into the other leg. Boxes indicate Clcn1 exons. Shown are the normal (bottom, exons 6, 7, 8 spliced directly together) and aberrant (7a, 8a and intron 6 inclusion) splicing patterns. Mice 190 and 191 are uninjected controls.
Figure 5B:
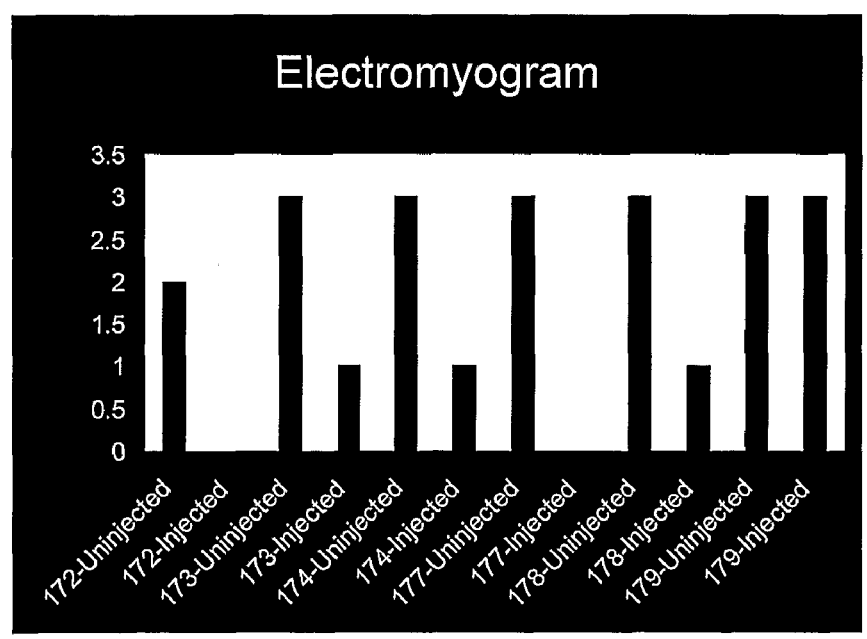
FIG. 5B shows an electromyogram depicting the results of the myotonia analysis performed. The scale (Y-axis) runs from 0 to 3, with 3 corresponding to severe myotonia. Zero equals no observed myotonic discharges, 1 equals occasional myotonic discharge, 2 equals abundant myotonic discharges and 3 equals myotonic discharge in nearly every insertion. The X-axis shows the mouse number and whether the TA was injected or uninjected with rAAV1/Myc-hMBNL1.

HSA$^{LR}$ mice were anesthetized using isoflurane, and the left tibialis anterior (TA) muscle was injected with 13.4 μL PBS containing 1×10$^{11}$ rAAV1Myc-hMBNL1, or the right leg was injected with PBS ("uninjected"). Four weeks post-injection, the mice were anesthetized using 2.5% avertin, and the left and right TAs were collected for total RNA preparation and assayed for recovery of the normal Clcn1 pre-mRNA splicing pattern (FIG. 5A)

Reverse transcription was carried out using 5 μg of total RNA and 300 ng of random hexamers in a final volume of 20 μl. After, RNase H treatment for 15 minutes at 37° C., 4 μl of cDNA was used for PCR. The final volume of the PCR reaction was 50 μl, which contained 30 pmoles of forward primer (5'-TGAAGGAATACCTCACACTCAAGGCC-3') (SEQ ID NO: 40) in exon 5 of Clcn1 and 30 pmoles of reverse primer (5'-CACGGAACACAAAGGCACTGAATGT-3') (SEQ ID NO: 41) in exon 8 of Clcn1. In addition, the reaction was spiked with 10 μCi of dCTP-[α$^{32}$P]. 27 cycles were carried out at annealing and extension temperatures of 55° C. and 72° C., respectively. Thirty percent of the total PCR products were resolved on a 5% acrylamide gel followed by exposure of the gel to an autoradiography film.

Mice number 188 and 189 were injected on the same day and processed together. Mouse number 190 and 191 were littermates that were neither injected with virus nor with PBS (included as uninjected controls). The results show that the levels of the abnormal splicing products were decreased, while the level of the normal splicing product was increased, following rAAV1Myc-hMBNL1 injection.

The mice were also tested for myotonia by electromyography (EMG). Four weeks post-injection, EMG was performed on the injected and uninjected (the latter corresponding, for this example, to those mice not injected with virus, but, rather, with PBS alone) TA of six HSA$^{LR}$ mice. The Y-axis shows the observed severity of myotonia following insertion of the electrode. Five out of six mice showed virtual elimination of myotonia in the injected TA muscles (injected with virus), while, in the uninjected TA of the same animal, robust myotonia (grade level=3) was observed. The results show that injection of the HSA$^{LR}$ mice with rAAV1Myc-hMBNL1 (41 kDa isoform expressed) into the tibialis anterior results in reduced myotonia in as little as four weeks' time.

Example 5

Effect of MBNL Proteins on Alternative Splicing

To determine whether MBNL proteins can alter the splicing patterns of pre-mRNAs known to be abnormally regulated in DM1 striated muscle, GFP fusion proteins of all three MBNL proteins were transiently expressed with human and chicken cTNT minigenes in primary chicken skeletal muscle cultures. GFP fusions with MBNL1, 2 and 3 were provided by Dr J D Brook (Fardaei M, Rogers M T, Thorpe H M, Larkin K, Hamshere M G, Harper P S, Brook J D (2002), *Hum Mol Genet* 11: 805-814). The cTNT, IR and clathrin light chain B minigenes were previously described (Kosaki A, Nelson J, Webster N J (1998), *J Biol Chem* 273: 10331-10337; Philips A V, Timchenko L T, Cooper T A (1998), *Science* 280: 737-741; Stamm S, Casper D, Hanson V, Helfman D M (1999), *Brain Res Mol Brain Res* 64: 108-118; Ladd A N, Charlet-B N, Cooper T A (2001), *Mol Cell Biol* 21: 1285-1296). The MBNL mutant human cTNT minigene was generated by inverse PCR.

Transient transfection and RT-PCR analysis: HEK293 cells were plated at 500 000 cells per well in a six-well plate in DMEM supplemented with 10% FBS and Gibco penicillin-streptomycin. At 24 h after plating, the cells were transfected with 1 μg of minigene and 2 μg of protein expression plasmid using Fugene6 (Roche, Indianapolis, Ind.), according to the manufacturer's directions. Protein and RNA were harvested 36-48 h after transfection.

Human and chicken cTNT and human IR minigenes were expressed with or without each of the three GFP-MBNL fusion proteins or with GFP alone. Duplicate transfections were used for extraction of RNA and protein. Inclusion of cTNT exon 5 or IR exon 11 was assayed by RT-PCR.

Chicken primary muscle cultures were prepared, maintained and transfected as previously described, using 0.5 µg minigene reporter and 1 µg expression plasmid Xu R, Teng J, Cooper T A (1993), Mol Cell Biol 13: 3660-3674). COSM6 cells were plated at 150 000 cells per well in a six-well plate in DMEM supplemented with 10% FBS, Gibco penicillin-streptornycin and L-glutamine. At 24 h after plating, the cells were transfected with 500 ng of minigene and 1 µg of protein expression plasmid using Fugene6 (Roche, Indianapolis, Ind.) according to the manufacturer's directions. Protein and RNA were harvested 36-48 h after transfection. RNA isolation and RT-PCR analysis for the cTNT, IR, and clathrin light-chain B minigenes were performed as described previously (Philips A V, Timchenko L T, Cooper T A (1998), Science 280: 737-741; Stamm S, Casper D, Hanson V, Helfman D M (1999), Brain Res Mol Brain Res 64: 108-118; Savkur R S, Philips A V, Cooper T A (2001), Nat Genet 29: 40-47).

Western blot analysis to investigate alternative splicing related to MBNL: cells were harvested in protein loading buffer (62.5 mM Tris-HCl (pH 6.8), 2% SDS, 10% glycerol and 5% 2-β-mercaptoethanol) and the protein concentration was quantitated with the Non-Interfering Protein Assay (Genotech, St Louis, Mo.). Total protein lysates from HEK293 (20 µg) and primary chicken skeletal (30 µg) cultures were loaded on a 12.5% acrylamide gel and transferred to Immobilon-P membranes (Millipore, Bedford, Mass.). GFP was detected using JL-8 monoclonal antibody (BD Biosciences, Palo Alto, Calif.) at a dilution of 1:2000. The secondary antibody was a goat anti-mouse HRP conjugate (Jackson Immunoresearch, West Grove, Pa.) at a dilution of 1:5000.

To detect endogenous MBNL1, HeLa (50 µg) protein lysates were loaded on a 12.5% acrylamide gel. Blots were probed with the monoclonal 3A4 (16 mg/ml) at a dilution of 1:500. The secondary antibody was a sheep anti-mouse HRP conjugate (Amersham Biosciences, Piscataway, N.J.) at a dilution of 1:5000. For GAPDH in HeLa cells, 15 µg of total protein lysates was run on a 12.5% acrylamide gel, transferred to membranes and detected using the 6G5 monoclonal (Biogenesis, Kingston, N.H.) at a dilution of 1:100 000. The secondary antibody was a goat anti-mouse HRP conjugate (Jackson Immunoresearch, West Grove, Pa.) at a dilution of 1:5000.

GFP-MBNL1, 2 and 3 strongly repressed inclusion of both human and chicken cTNT exon 5 in primary chicken skeletal muscle cultures, while expression of GFP to levels comparable to, or greater than, GFP-MBNL fusion proteins had no effect on splicing (FIGS. 6A and 6B). Of note, GFP-MBNL1 was found to have a novel MBNL1 isoform lacking exons 7, 9 and 10 and containing a frameshift in exon 12. In addition, there were no differences in the splicing activity of GFP fusion proteins compared to Xpress epitope-tagged MBNL proteins (data not shown). Therefore, MBNL proteins are directly antagonistic to endogenous CELF activity, which activates cTNT exon inclusion in muscle (Charlet-B N, Logan P, Singh G, Cooper T A (2002a), Mol Cell 9: 649-658).

Another pre-mRNA target that is misregulated in DM striated muscle is the IR (Savkur R S, Philips A V, Cooper T A (2001), Nat Genet 29: 40-47; Savkur R S, Philips A V, Cooper T A, Dalton J C, Moseley M L, Ranum L P, Day J W (2004), Am J Hum Genet 74: 1309-1313). To test whether the MBNL family can also regulate human IR, the three MBNL family members were co-expressed with a human IR minigene. In contrast to the inhibitory effect of MBNL on cTNT splicing, coexpression of MBNL family members with an IR minigene strongly induces exon inclusion, whereas GFP alone had no effect (FIG. 6C).

To determine whether the MBNL family has a general effect on alternative splicing, all three MBNL proteins were co-expressed with a clathrin light-chain minigene containing the neuron-specific exon EN. The EN alternative exon in this minigene strongly responds to over-expression of the SR family of proteins and htra2-β1, but not CELF proteins (Stamm S, Casper D, Hanson V, Helfman D M (1999), Brain Res Mol Brain Res 64: 108-118; Singh G, Charlet B N, Han J, Cooper T A (2004), Nucleic Acids Res 32: 1232-1241; data not shown). Over-expression of GFP-MBNL1, 2 and 3 with the clathrin light-chain minigene had no effect on alternative splicing of exon EN (FIG. 6D). MBNL expression also did not affect splicing of an artificial alternative exon flanked by splice sites from human β-globin intron 1 (data not shown). These results demonstrate that MBNL proteins do not have a general effect on alternative splicing, but, rather regulate specific pre-mRNA targets. In summary, MBNL1, 2 and 3 regulate splicing of cTNT and IR alternative exons.

Example 6 siRNA-Mediated Depletion of MBNL1 and Splicing of cTNT and IR

To determine whether depletion of endogenous MBNL1 protein could also affect the splicing patterns of known DM pre-mRNA targets in human cells, siRNA constructs were designed to target MBNL1, but not MBNL2 and MBNL3. To confirm the specificity of the effects, two siRNA constructs were designed to target different regions of the MBNL1 mRNA.

SiRNA construct design and transfection: two custom siRNA duplexes were designed for RNAi against human MBNL1 using the Dharmacon siDESIGN program available on the world wide web at dharmacon.com, and were synthesized by Dharmacon. The sequences are as follows: THH31 mRNA target (AA-N19 format 5'→3') AACAGACAGACU-UGAGGUAUG (SEQ ID NO: 35), THH2 mRNA target (AA-N19 format 5'43 3') AACACGGAAUGUAAAUUUGCA (SEQ ID NO: 36), GFP siRNA duplex (Dharmacon, Lafayette, Colo. cat. no. D-001300-01-20). 300 000 HeLa cells were plated in 2 ml of antibiotic-free growth media (DMEM supplemented with 10% FBS) per well in a six-well plate. HeLa cells were chosen because they express MBNL1 (Miller J W, Urbinati C R, Teng-Umnuay P, Stenberg M G, Byrne B J, Thornton C A, Swanson M S (2000), EMBO J 19: 4439-4448) and are amenable to siRNA-mediated depletion (Elbashir S M, Harborth J, Lendeckel W, Yalcin A, Weber K, Tuschl T (2001), Nature 411: 494-498).

At 12 h after plating, the media was exchanged with 800 µl serum-free media (DMEM) per well. siRNA duplex (2.66 µg) was transfected using Oligofectamine (Invitrogen, Carlsbad, Calif.). 1 ml of 3× serum-containing media (DMEM supplemented with 30% FBS) was added after 4 h. After 12 h, the 3×serum-containing media was replaced with antibiotic-free growth media and the cells were transfected with 1 µg of minigene and 2.66 µg of siRNA duplex using Lipofectamine 2000 (Invitrogen, Carlsbad, Calif.). The media was exchanged with antibiotic-free growth media 6 h later. RNA and protein were harvested 48 h after transfection of the minigene.

Figure 7:
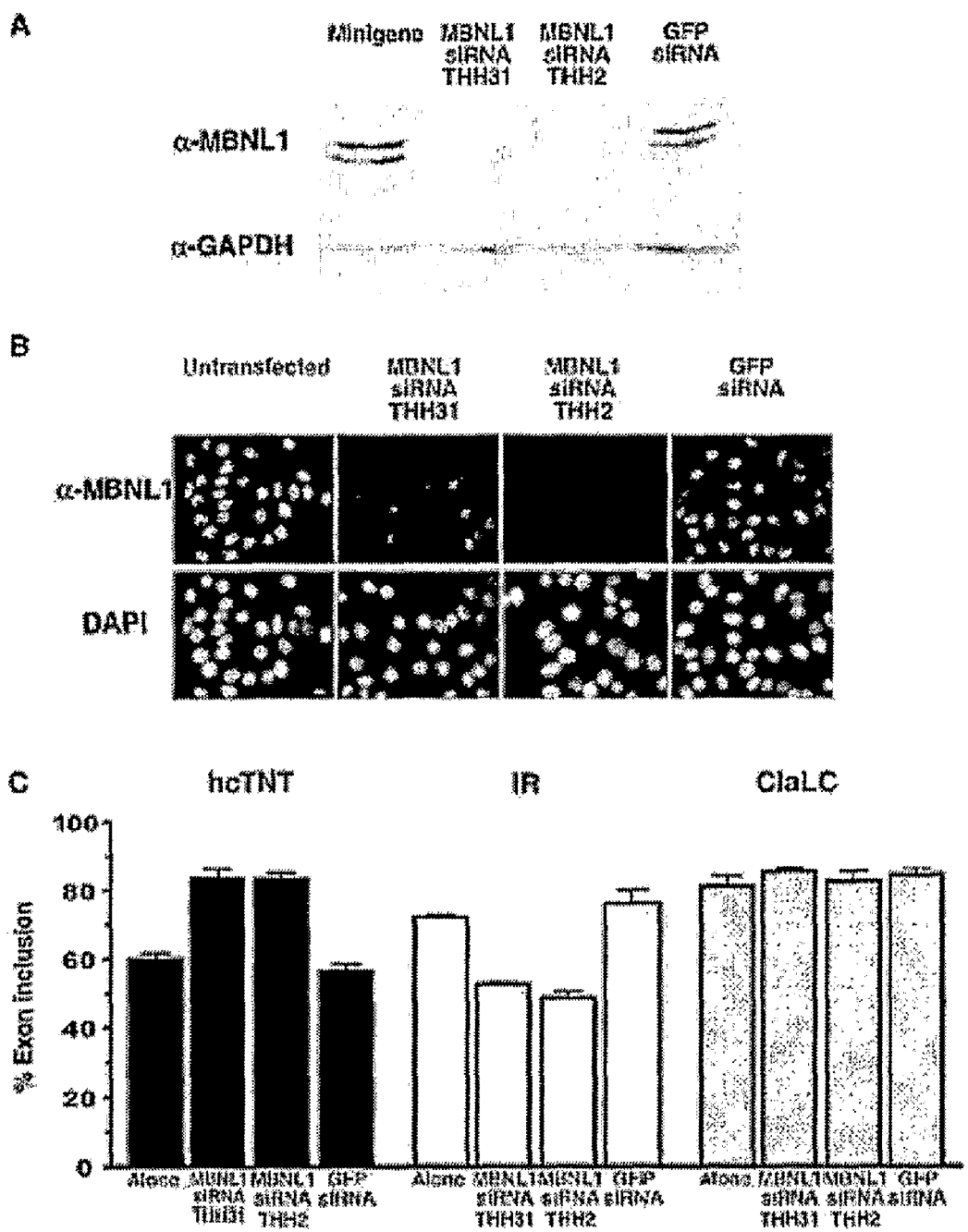
FIG. 7A shows a Western blot confirming depletion of endogenous MBNL1 by independent transfection of two different siRNA constructs using the MBNL1 monoclonal (mAb) 3A4, which recognizes two MBNL1 isoforms generated by alternative splicing (~41 and 42 kDa). GAPDH (~36 kDa) was used as a loading control.
FIG. 7B shows the results of immunofluorescence analysis using mAb 3A4 to confirm depletion of endogenous protein after independent transfection of each MBNL1 siRNA construct. Scale bar, 10 μm.
FIG. 7C shows, in bar graph form, the RT-PCR results from at least three transfections.

Independent transient transfection of each siRNA construct resulted in a knockdown of endogenous MBNL1 protein to less than 10-20%, based on comparisons to serial dilutions of the untransfected or mock-transfected lysates (FIG. 7A; data not shown).

Immunofluorescence analysis of MBNL1 depletion: HeLa cells were grown on coverslips in six-well plates and transfected with 2.66 µg siRNA using Oligofectamine. The coverslips were washed with cold PBS (pH 7.4) and fixed in 4% paraformaldehyde/PBS for 15 min. After three washes with PBS, the cells were dehydrated with 70% ethanol overnight at 4° C. The coverslips were then rehydrated with PBS for 10 min and incubated with 3% BSA/PBS for 15 min at room temperature. The cells were washed once with PBS and incubated with the primary antibody 3A4 (10 mg/ml) at a dilution of 1:1000 in 3% BSA/PBS at room temperature for 1 h. The cells were then washed three times with PBS and incubated with the secondary antibody, Alexa Fluor-labeled goat anti-mouse IgG (2 mg/ml, Molecular Probes, Eugene, Oreg.), at a dilution of 1:100 in 3% BSA/PBS at room temperature for 1 h. The cells were then washed with PBS three times, counterstained with DAPI (MolecularProbes, Eugene, Oreg.) and mounted for visualization by fluorescence microscopy.

Analysis of MBNL1 depletion by immunofluorescence demonstrated predominantly nuclear expression that was greatly reduced in the majority of cells by each siRNA construct (FIG. 7B). In addition, the siRNA constructs silenced effectively the expression of GFP-MBNL1, but not GFP-MBNL2, GFP-MBNL3 or GFP from transiently transfected plasmids, and neither MBNL1 siRNA affected the levels of endogenous MBNL2 protein (data not shown). These results indicate that the siRNAs preferentially silence MBNL1.

MBNL1 depletion and cTNT and IR minigene splicing: to determine whether depletion of endogenous MBNL1 affected alternative splicing of cTNT, IR and clathrin light chain, the minigenes were transfected with each siRNA construct. Depletion of MBNL1 promoted exon inclusion in cTNT, exon skipping in IR and only minimal splicing changes in the clathrin light-chain minigene (FIG. 7C). siRNA-mediated depletion of MBNL1 with two independent constructs reproduces the DM splicing patterns for cTNT and IR minigenes. GFP siRNA had no effect on splicing of any of the tested minigenes. MBNL1 siRNA had minimal effects on splicing of a rat clathrin light-chain minigene.

These splicing effects were not caused by general activation of the mammalian RNAi machinery because siRNA targeting GFP or luciferase and nonspecific pools of siRNA had minimal effects on splicing of the three minigenes (FIG. 7C; plus data not shown). Furthermore, the alteration in cTNT splicing caused by MBNL1 depletion in HeLa cells can be reversed by expression of GFP-MBNL2 or GFP-MBNL3, but not GFP (data not shown), demonstrating that adding back MBNL isoforms not targeted by MBNL1 siRNA rescues the splicing effects of MBNL1 deficiency.

The data indicate that endogenous MBNL1 regulates the splicing of human cTNT and IR minigenes. Interestingly, siRNA-mediated depletion of MBNL1 reproduces the splicing pattern observed in DM1 for cTNT (exon inclusion) and IR (exon skipping), and is opposite to the pattern observed when MBNL1 is over-expressed. The over-expression and depletion data indicate that endogenous MBNL1 regulates the alternative splicing of cTNT and IR minigenes, and suggest that MBNL1 regulates these pre-mRNAs via specific cis-regulatory elements. The effects of MBNL on the cTNT and IR alternative exons are the opposite of the splicing patterns induced by CELF proteins, implying an antagonistic relationship between these protein families.

Example 7

Figure 8:
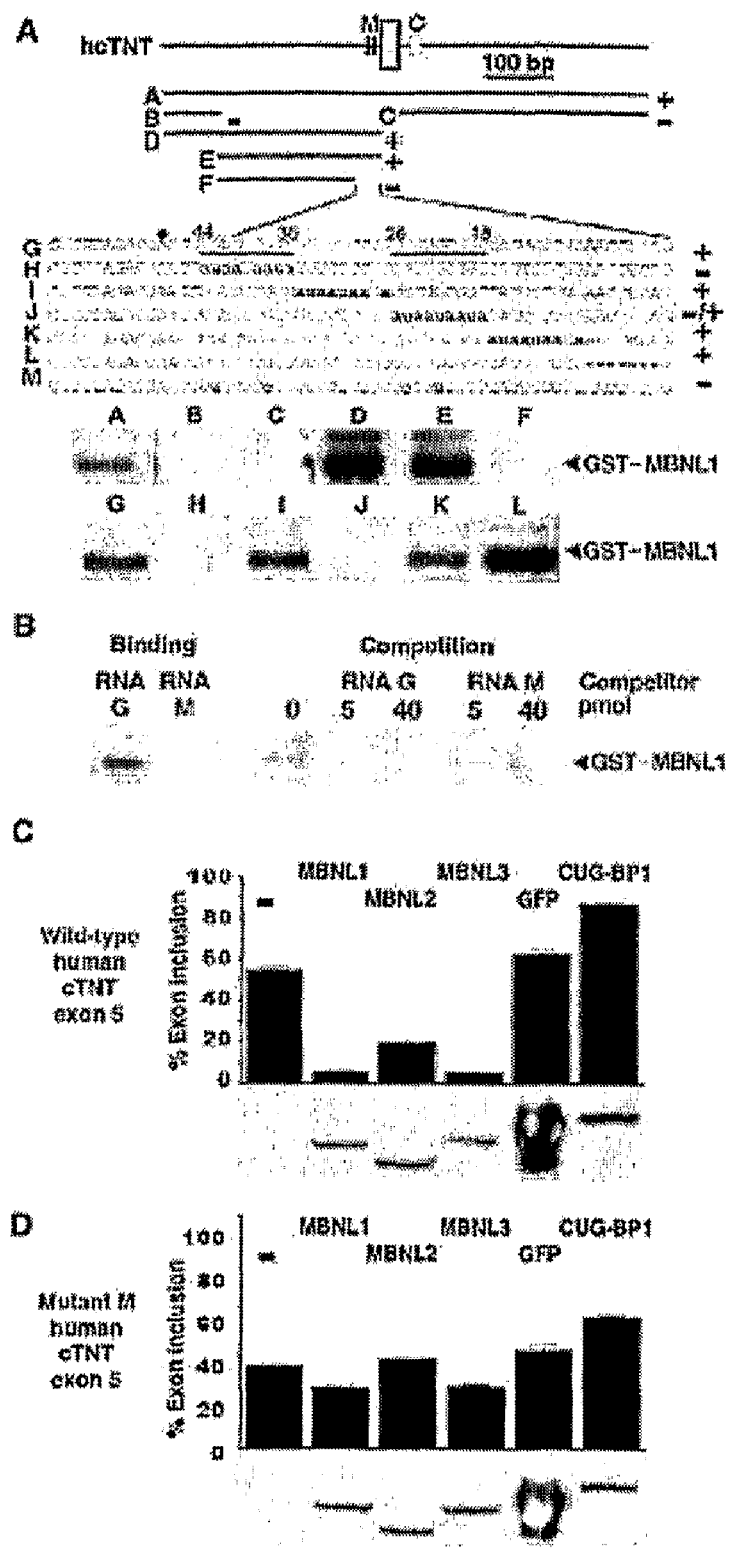
FIG. 8 shows MBNL1 binds upstream of exon 5 in human cTNT at a site distinct from the CUG-BP1-binding site. (A) Binding of recombinant GST-MBNL1 to uniformly $^{32}$P-labeled RNA was assayed by UV cross-linking. Scanning mutagenesis was performed by replacing 6 nt blocks with AUAAUA and identified two binding sites 18 and 36 nt upstream of the alternative exon. The MBNL1-binding sites (M) and the CUG-BP1-binding site (C) are located on opposite sides of exon 5. (+) and (−) indicate binding; (·)indicates a putative branch point adenosine. (B) Four nucleotide substitutions significantly reduce binding of recombinant MBNL1 detected by UV-cross-linking. Competition of GST-MBNL1 binding to $^{32}$P-labeled RNA G by the indicated picomoles of non-labeled RNAs G or M shown in A). (C, D) MBNL1-binding site mutations reduce responsiveness to MBNL1, MBNL2 and MBNL3 co-expression but not CUG-BP1 in COSM6 cells. Human cTNT minigenes containing the natural sequence (C) or the four nucleotide substitutions (mutation M in A) in the MBNL1-binding site (D) were co-expressed with GFP or the indicated GFP fusion proteins. Exon inclusion was assayed by RT-PCR.
Figure 9:
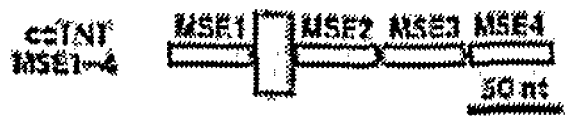
FIG. 9A schematically depicts how the chicken cTNT MSE1-4 RNA contains an alternative exon flanked by four MSEs. Below.
FIG. 9B shows UV-cross-linking assay results for competition of GST-MBNL1 binding to labeled chicken cTNT MSE1-4 RNA by non-labeled MSE RNAs. Picomoles of competitor RNA are indicated.
FIG. 9C shows the results of the scanning mutagenesis performed, identifying two MBNL1-binding sites within MSE4.
FIG. 9D shows an alignment of the four MBNL1-binding motifs in human and chicken cTNT, which reveals a common motif.
Figure 9:
Figure 9:
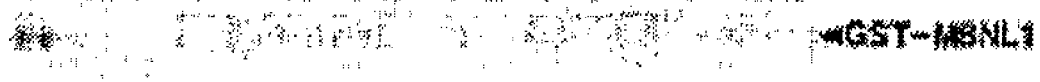
Figure 9:

Binding of MBNL1 to Introns Adjacent to the Human and Chicken cTNT alternative Exons UV cross-linking analysis of MBNL1 binding to human cTNT: to determine whether the splicing effects of MBNL1 on pre-mRNA targets were direct or indirect, a UV-cross-linking assay was performed using purified recombinant GST-MBNL1 and uniformly labeled in vitro-transcribed segments from the human cTNT gene. Uniformly $^{32}$P-labeled RNAs were transcribed in vitro using [α-$^{32}$P]GTP and [α-$^{32}$P]UTP (Perkin-Elmer, Wellesley, Mass.) from PCR products or cloned regions of the human or chicken introns 4 and 5, as represented in FIGS. 8 and 9.

UV-cross-linking assays were performed using radiolabeled transcripts standardized for picomoles of G and U. UV-cross-linking assays included 1 µg of purified GST-MBNL1 in the presence of 1 µg BSA, 1 µg tRNA, 0.3 µg heparin, 0.3 mM magnesium acetate, in 2 mM magnesium acetate, 2 mM ATP, 16 mM HEPES (pH 7.9), 65 mM potassium glutamate, 0.16 mM EDTA, 0.4 mM DTT and 16% glycerol. Binding was for 10 min at 30° C. Recombinant GST-MBNL1 protein was produced as described (Miller J W, Urbinati C R, Teng-Umnuay P, Stenberg M G, Byrne B J, Thornton C A, Swanson M S (2000), *EMBO J* 19: 4439-4448). Competitions were performed as described previously (Singh G, Charlet B N, Han J, Cooper T A (2004), *Nucleic Acids Res* 32: 1232-1241). The indicated amounts of non-labeled competitor RNAs were added to the binding reaction 10 min prior to addition of labeled substrate RNA.

Figure 6:
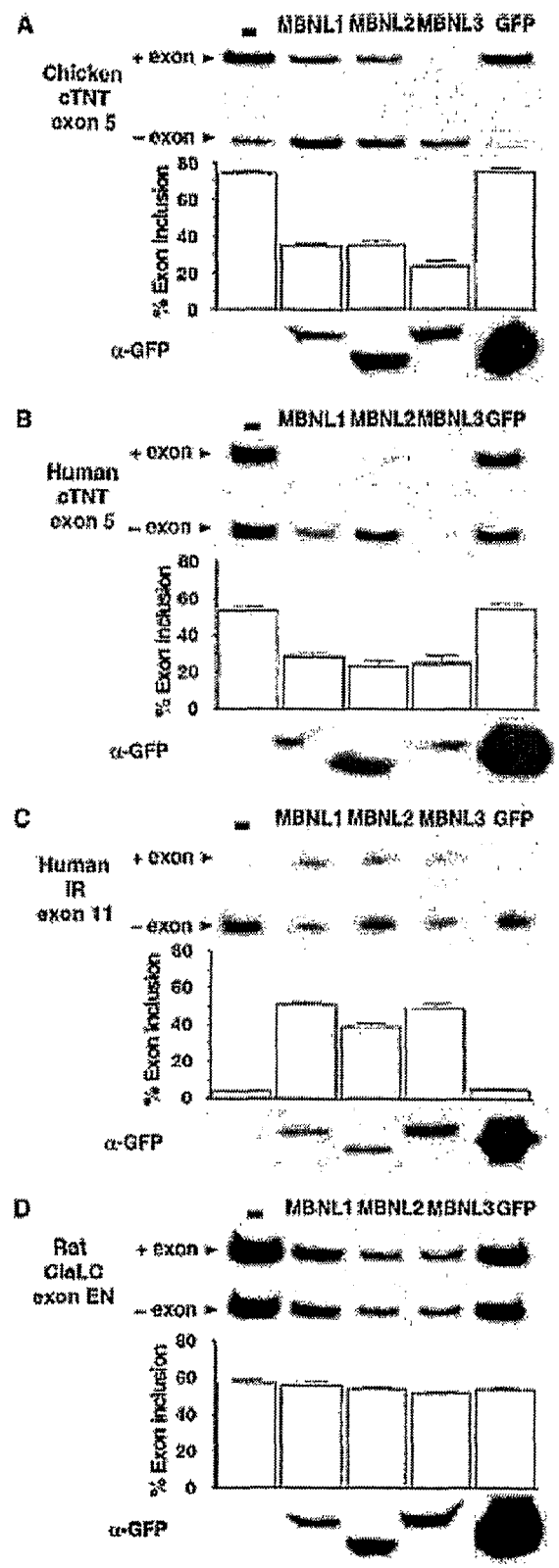
FIG. 6 shows the results of RT-PCR analysis of exon inclusion. Percent exon inclusion is calculated as ((mRNA+exon)/(mRNA−exon+mRNA+exon))×100. Results are derived from at least three independent experiments. Expression of GFP-MBNL1 (~72 kDa), GFP-MBNL2 (~58 kDa), GFP-MBNL3 (~70 kDa) and EGFP (~27 kDa) was detected by Western blot analysis using an anti-GFP monoclonal antibody. All three MBNL proteins promote exon 5 skipping of (A) chicken and (B) human cTNT exon 5 in primary skeletal muscle cultures. (C) All three MBNL proteins promote exon 11 inclusion in a human IR minigene in HEK293 cells. (D) MBNL proteins have minimal effects on splicing of exon EN in a clathrin light-chain B minigene in primary skeletal muscle cultures.

The human cTNT minigene contains a 732 nucleotide (nt) cTNT genomic fragment that is necessary and sufficient to respond to MBNL1 over-expression and depletion (FIGS. 6 and 7C). To identify MBNL1-binding sites within this cTNT pre-mRNA region, uniformly $^{32}$P-labeled, in vitro-transcribed RNAs covering the entire region were used for UV-cross-linking binding assays. As shown in FIG. 8A, the binding of GST-MBNL1 on human cTNT was mapped to a 41 nt region within the 3' splice site of exon 5 (compare RNAs C, D, E and F) located between a near-consensus branch point sequence and the 3' cleavage site of the upstream intron.

Scanning mutagenesis identification of binding sites: scanning mutagenesis identified two MBNL1-binding sites located 18 and 36 nt upstream from exon 5 (FIG. 8A). The absence of binding to long intronic segments (RNAs F and C) and RNAs containing nucleotide substitutions (RNAs H, J and M; see below) demonstrate binding specificity. This analysis indicates that, for cTNT, the MBNL1-binding site is distinct from the CUG-BP1-binding site, which is located downstream from the alternative exon (Philips A V, Timchenko L T, Cooper T A (1998), *Science* 280: 737-741).

UV cross-linking analysis of binding of MBNL1 with nucleotide substitutions: nucleotide substitutions that disrupt both MBNL1-binding sites were introduced into the human cTNT minigene to test whether MBNL1 binding was required to affect responsiveness to MBNL1 expression in vivo. As the MBNL-binding site is located within the 3' splice site of intron 4, only four nucleotide substitutions were introduced to reduce the effects of MBNL-binding site mutations on basal splicing efficiency (RNA M, FIG. 8A). These substitutions prevented binding of recombinant MBNL1 to an RNA that is otherwise identical to RNA G containing the wild-type sequence (FIG. 8B). In addition, non-labeled RNA M was much less efficient than RNA G in competing binding of MBNL1 to labeled RNA G (FIG. 8B).

When introduced into the human cTNT minigene, the MBNL1-binding site mutation significantly reduced (MBNL1 and MBNL3) or eliminated (MBNL2) responsiveness to MBNL proteins (FIGS. 8C and 8D), demonstrating that loss of MBNL1 binding in vitro directly correlates with decreased responsiveness to MBNL1 in vivo. These results demonstrate that regulation by MBNL protein is mediated via binding the pre-mRNA, and suggest that all three MBNL proteins regulate human cTNT splicing by binding to the same site. In contrast, the MBNL1-binding site mutations had little effect on responsiveness to CUG-BP1 (FIGS. 8C and 8D). GFP alone had minimal effects on splicing. Thus, MBNL proteins regulate splicing by binding to the human cTNT pre-mRNA, and regulation by CUG-BP1 does not require the MBNL1-binding site.

UV cross-linking analysis of MBNL1 binding to chicken cTNT: UV-cross-linking analysis was performed to identify MBNL1-binding site(s) associated with the chicken cTNT alternative exon 5. The genomic segment of chicken cTNT that responds to MBNL expression contains 99 and 142 nt of upstream and downstream introns flanking the alternative exon, respectively. Within the intronic segments are four muscle-specific splicing enhancers (MSEs, FIG. 9A) previously shown to be required for enhanced exon inclusion in embryonic striated muscle (Ryan K J, Cooper T A (1996), Mol Cell Biol 16: 4014-4023; Cooper T A (1998), Mol Cell Biol 18: 4519-4525) and required for regulation by all the six CELF family members (Ladd A N, Charlet-B N, Cooper T A (2001), Mol Cell Biol 21: 1285-1296; Ladd A N, Nguyen N H, Malhotra K, Cooper T A (2004), J Biol Chem 279: 17756-17764). RNAs containing MSEs 1-4 or individual MSEs were transcribed in vitro as uniformly $^{32}$P-labeled RNAs and used for UV cross-linking. GST-MBNL1 bound strongly to MSE4 and slightly to MSE1 (FIG. 9A).

In competition studies, non-labeled MSE1 RNA poorly competed in the binding of GST-MBNL1 to RNA containing MSE1-4, while MSE4 effectively competed in binding (FIG. 9B), consistent with the UV-cross-linking results. The absence of competition by MSE2 or MSE3 demonstrates the sequence specificity of MBNL1 binding (FIG. 9B). To define the MBNL1-binding site(s) within MSE4, scanning mutagenesis was performed. Two regions required for MBNL1 binding were identified at 94 and 120 nt downstream from the exon (FIG. 9C). Alignment of the four MBNL1-binding sites in chicken and human cTNT revealed a common motif of YGCU(U/G)Y (FIG. 9D). Taken together, these data indicate that MBNL1 directly binds to introns adjacent to the human and chicken cTNT alternative exons.

Of note, proteins from all three MBNL genes contain two pairs of Cys3His zinc-finger-related motifs with identical spacing between cysteine and histidine residues in fingers 1 and 3 (CX7CX6CX3H) and fingers 2 and 4 (CX7CX4CX3H) (Miller J W, Urbinati C R, Teng-Umnuay P, Stenberg M G, Byrne B J, Thornton C A, Swanson M S (2000), EMBO J 19: 4439-4448; Fardaei M, Rogers M T, Thorpe H M, Larkin K, Hamshere M G, Harper P S, Brook J D (2002), Hum Mol Genet 11: 805-814; Squillace R M, Chenault D M, Wang E H (2002), Dev Biol 250: 218-230). The Cys3His-type zinc-finger is an evolutionarily conserved motif found in a number of proteins that perform diverse RNA-processing functions, and mutation of this motif results in a loss of RNA binding and disrupts protein function (Bai C, Tolias P P (1996), Mol Cell Biol 16: 6661-6667; Bai C, Tolias P P (1998), Nucleic Acids Res 26: 1597-1604; Lai W S, Carballo E, Strum J R, Kennington E A, Phillips R S, Blackshear P J (1999), Mol Cell Biol 19: 4311-4323; Stoecklin G, Colombi M, Raineri I, Leuenberger S, Mallaun M, Schmidlin M, Gross B, Lu M, Kitamura T, Moroni C (2002), EMBO J 21: 4709-4718).

MBNL1 also binds to specific sequences within single-stranded RNA, consistent with the results from other Cys3His zinc-finger proteins (Cheng Y, Kato N, Wang W, Li J, Chen X (2003), Dev Cell 4: 53-66; Michel S L, Guerrerio A L, Berg J M (2003), Biochemistry 42: 4626-4630). The above-delineated results demonstrate that MBNL1 binds to cis-elements in chicken cTNT intron 5 required for muscle-specific splicing.

Example 8

CELF Protein Cis-Regulatory Elements in cTNT and IR and Regulation by MBNL1

The CUG-BP1-binding site located downstream from exon 5 in the human cTNT minigene is required for regulation by all six CELF proteins (Philips A V, Timchenko L T, Cooper T A (1998), Science 280: 737-741); T Ho, unpublished data), and is distinct from the MBNL-binding site mapped in FIG. 8. The results shown previously demonstrate that CUG-BP1 regulates minigenes in which MBNL1-binding site mutations have greatly reduced or eliminated MBNL responsiveness (FIG. 8D).

Figure 10:
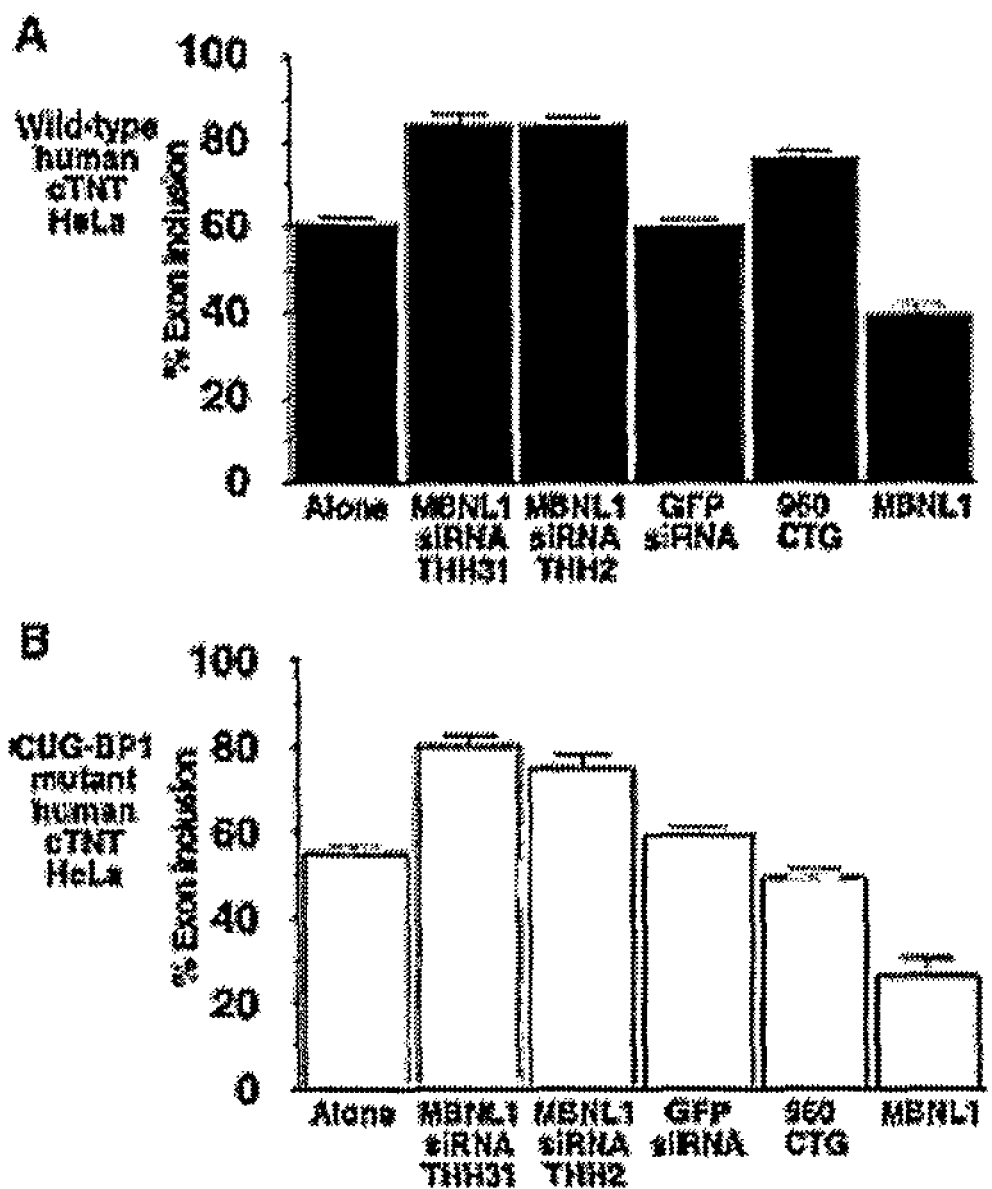
FIG. 10A shows, in bar graph form, the results of the over-expression and depletion experiments with respect to the wild-type cTNT minigene, co-transfected with the indicated siRNA constructs, a plasmid expressing a DMPK minigene with 960 CUG repeats (Philips et al, 1998) or a GFP-MBNL1 expression plasmid in HeLa cells.
FIG. 10B shows the results with respect to the mutant cTNT minigene with point mutations that prevent CUG-BP1 binding and regulation.

Analysis of the importance of the CUG-BP1 binding site to minigene regulation by MBNL1: to determine whether MBNL1 can regulate minigenes lacking the CUG-BP1-binding site, GFP-MBNL1 or MBNL1 siRNA was cotransfected with a human cTNT minigene containing mutated CUG-BP1-binding sites. Plasmids expressing DMPK exons 11-15 containing 960 interrupted CUG repeats in exon 15 were cloned using techniques as previously described (Philips A V, Timchenko L T, Cooper T A (1998), Science 280: 737-741). The over-expression and depletion results demonstrate that cTNT minigenes containing the mutant and wild-type CUG-BP1-binding sites are equally responsive to MBNL1 (FIGS. 10A and 10B). GFP-MBNL2 and 3 also showed similar regulation of wild-type and mutant human cTNT minigenes (data not shown). These results indicate that the regulation of human cTNT by MBNL1 is independent of CELF regulation.

Figure 11:
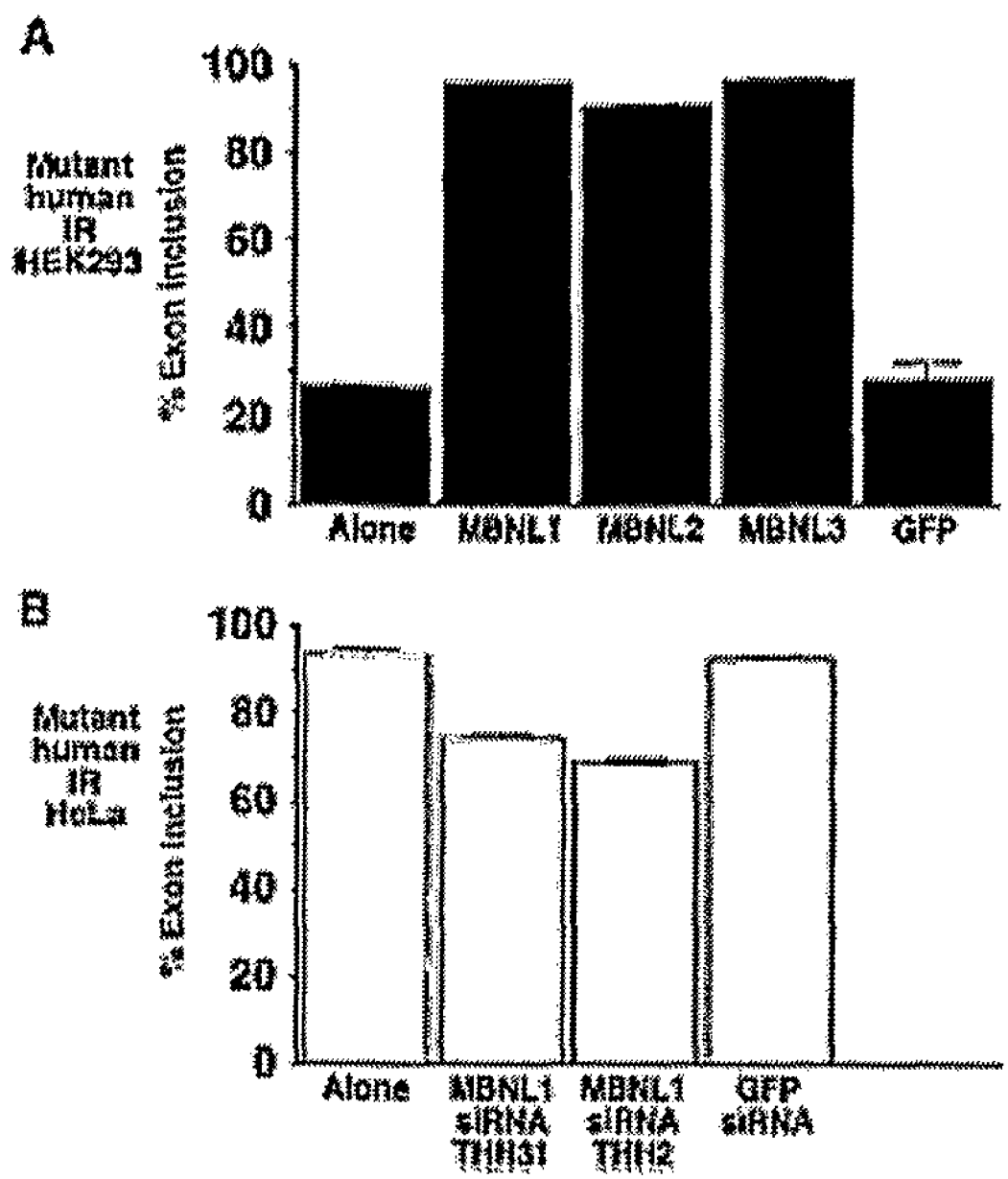
FIG. 11A shows, in bar graph form, the results of the over-expression and depletion experiments with respect to the mutant human IR minigene lacking the CUG-BP1-binding site in HEK293 cells.
FIG. 11B shows the results with respect to the human IR minigene lacking the CUG-BP1-binding site.

Similarly, for the IR minigene, regulation by CUG-BP1 requires a CUG-BP1-binding site in a 110 nt region located upstream of IR exon 11 (Savkur R S, Philips A V, Cooper T A (2001), Nat Genet 29: 40-47). A mutant IR minigene lacking the CUG-BP1-binding site was co-expressed with GFP-MBNL1, 2 and 3 in HEK293 cells (FIG. 11A) or MBNL1 siRNA constructs in HeLa cells (FIG. 11B) to determine whether regulation by MBNL proteins requires the CUG-BP1-binding site. The mutant IR minigenes displayed regulation by MBNL proteins, which was comparable to the wild-type IR minigenes (compare FIGS. 11A and 6C and 11B and 7C). These results indicate that regulation of human cTNT and IR by MBNL proteins does not require the CUG-BP1-binding site. In other words, the deletion of the human IR CUG-BP1-binding site does not affect regulation by MBNL1. All three of the MBNL proteins promoted exon 11 inclusion of the mutant human IR minigene lacking the CUG-BP1-binding site in HEK293 cells (FIG. 11A). Furthermore, RNAi depletion of MBNL1 in HeLa cells using the indicated siRNA constructs promoted exon 11 skipping in the human IR minigene lacking the CUG-BP1-binding site (FIG. 11B).

Mutant cTNT and IR minigenes lacking the CUG-BP1-binding site respond as strongly as non-mutated minigenes to MBNL1 depletion by RNAi (FIGS. 10B and 11B). However, neither of these minigenes respond to the trans-dominant effects of co-expressed CUG repeat RNA as do the non-mutated minigenes (Philips A V, Timchenko L T, Cooper T A (1998), *Science* 280: 737-741; Savkur R S, Philips A V, Cooper T A (2001), *Nat Genet* 29: 40-47; 960CTG, FIG. 9). The RNAi results demonstrate that the mutated cTNT and IR minigenes are 'competent' to respond to MBNL1 depletion, and, yet, they do not respond to co-expression of CUG repeat RNA. Therefore, while it has been demonstrated that MBNL proteins are alternative splicing regulators of cTNT and IR alternative exons, these results indicate that MBNL depletion by CUG repeat RNA is not sufficient to account for the trans-dominant effect of CUG repeat RNA on splicing.

As shown previously, and in FIG. 10B, here, the cTNT and IR minigenes made insensitive to CELF regulation by mutations in the CUG-BP1-binding site no longer respond to expanded CUG repeat RNA, suggesting that the trans-dominant effect is mediated at least in part via an intact CUG-BP1-binding site (FIG. 10B; Philips A V, Timchenko L T, Cooper T A (1998), *Science* 280: 737-741; Savkur R S, Philips A V, Cooper T A (2001), *Nat Genet* 29: 40-47). The present results show that the mutated cTNT and IR minigenes are competent to respond to MBNL depletion by RNAi as strongly as the non-mutated minigenes, yet they do not respond to CUG repeat RNA. If expanded CUG repeats affected cTNT and IR splicing simply by sequestering and depleting MBNL, then the co-expression of CUG repeats should have affected splicing of the mutated as well as non-mutated minigenes. It is, thus, indicated that the repeats have a trans-dominant effect on splicing by a mechanism more complex than MBNL depletion alone.

Example 9

Fluorescence in situ Hybridization (FISH) and Immunofluorescence (IF) Analysis of DM1 Brain Origin and preparation of tissue samples: to study the expression and distribution of expanded poly(CUG)RNA in relation to putative RNA binding proteins in the brain, autopsy materials were obtained from ten DM1 patients (mean age 56 years, range 44-78 years, 7 men and 3 women) and 13 controls (6 with no neurologic disease, 2 with Alzheimer disease, 4 with Huntington disease, and one with refractory epilepsy). The mean post-mortem interval for DM1 patients was 6 hours (range 2 to 14 hours). At the time of autopsy, coronal sections of brain were prepared and placed on aluminum slabs cooled on dry ice. In addition, selected regions were dissected and flash frozen in liquid nitrogen. All samples were stored at −70° C.

Nine of the DM1 patients had signs of classical DM1 before age 30 and died of complications related to the disease (respiratory failure in 7, sudden cardiac death in 2). The other DM1 patient had minimal symptoms of DM1 and died at age 78 yrs of unrelated disease. Genetic confirmation was performed as previously described by PCR or Southern blot on DNA isolated from postmortem brain tissue (Thornton, C. A., Johnson, K., an Moxley, R. T. (1994), *Ann. Neurol.*, 35, 104-107). Southern blots of cortical DNA samples showed a broad range of expanded alleles ranging in size from 5 to 12 kb (not shown). The individual with the minimal DM phenotype had a CTG repeat expansion length of 77 repeats in DNA isolated from peripheral blood, brain, and other tissues.

Fluorescence in situ hybridization (FISH) analysis of brain sections: FISH was performed as described (Mankodi, A., Urbinati, C. R., Yuan, Q. P., Moxley, R. T., Sansone, V., Krym, M., Henderson, D., Schalling, M., Swanson, M. S., and Thornton, C. A. (2001), *Hum. Mol. Genet.*, 10, 2165-2170) with slight modifications. Frozen sections (12 μm) were fixed in 3% paraformaldehyde PBS for 30 min, permeabilized in 2% acetone PBS (pre-chilled at −20° C.) for 5 min, and then prehybridized in 30% formamide and 2×SSC at room temperature for 10 min. Next, sections were hybridized with probe (1 ng/μl) for 2 h at 37° C. in buffer (30% formamide, 2×SSC, 0.02% BSA, 66 μg/ml yeast rRNA, 2 mM vanadyl complex) and then washed for 30 min in 30% formamide/2× SSC at 42° C. followed by 1×SSC for 30 min at room temperature. Probes were HPLC purified 2-O-methyl RNA 20-mers (IDT, Coralville, Iowa) composed of CAG-, CUG- or GUC-repeats, and labeled with Texas Red at the 5' end. Images were obtained on an Olympus AX70 epifluorescence microscope at 1,000-fold magnification. To compare the relative fluorescence intensities for RNA foci, sections were processed on the same slide, imaged under the same illumination and exposure settings, and then analyzed using MCID v6.0 software (Imaging Research Inc., St. Catherines, Ontario).

Fluorescence in situ hybridization (FISH) of brain sections with CAG repeat probes revealed nuclear RNA foci in every individual with DM1 (n=10, FIG. 12A) but not in controls with (n=7) or without (n=6) neurologic disease. RNA foci were not observed with CUG (sense) or GUC repeat probes. The hybridization of CAG probes to nuclear foci in DM1 did not-require denaturation of genomic DNA. These results indicate that CAG repeat probes recognize CUG expansion RNA rather than a cross-reactive RNA or DNA.

Figure 12:
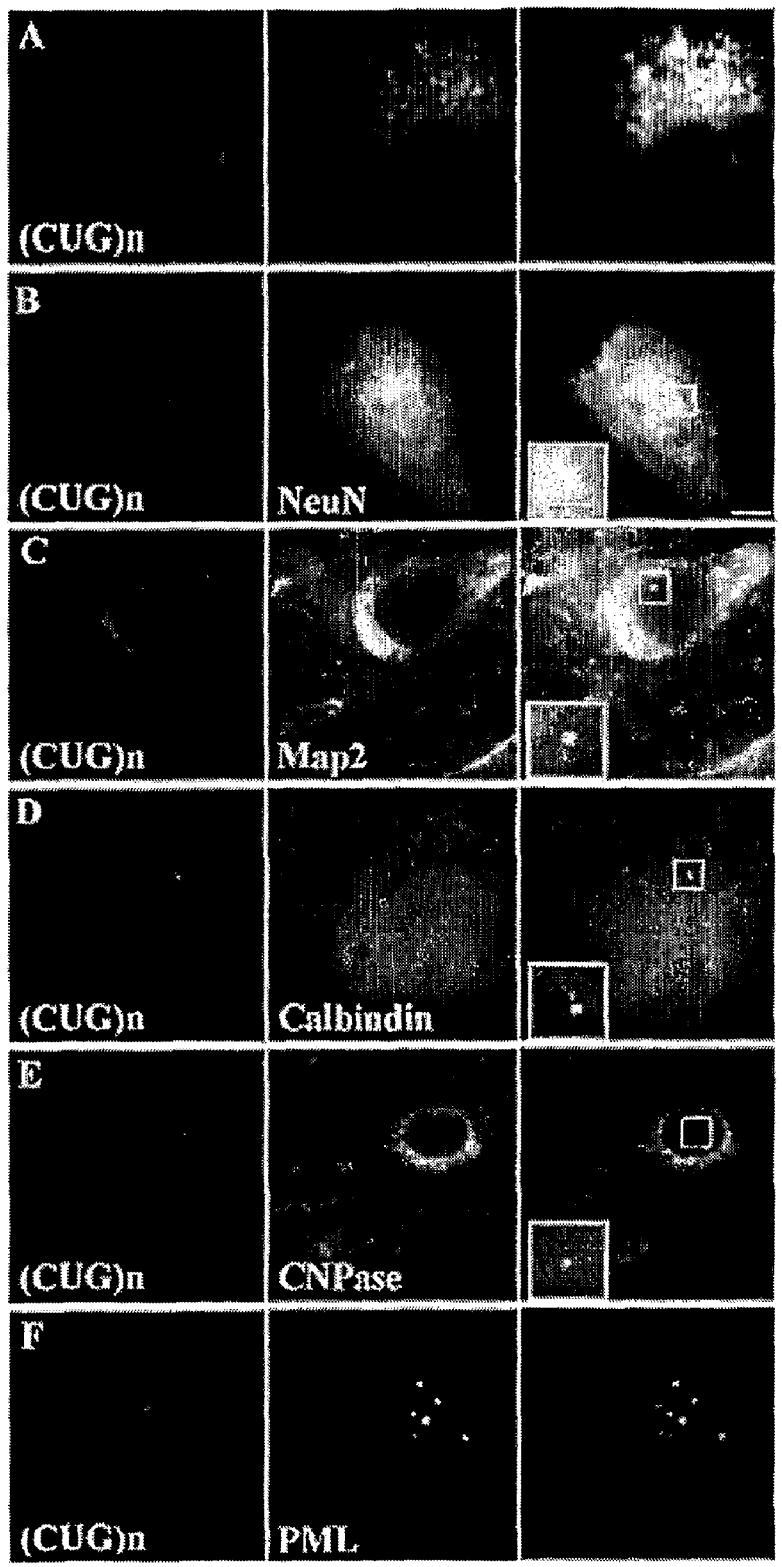
FIG. 12 shows the results of FISH (left panels) and IF (middle panels) analyses of frozen sections of DM1 brain showing nuclear foci of mutant DMPK mRNA. FISH, IF, and nuclear stain (DAPI, blue) images are merged in panels on the right. In (A), FISH (without IF) using Texas Red-labeled CAG repeat probe shows an RNA inclusion in frontal cortical neuron. Autofluorescence from lipofuscin occurs at broad spectrum of wavelengths. It appears in every color channel and as yellow-brown perinuclear material in the merged image. RNA inclusions in cerebral cortex are confined to neurons identified by IF for NeuN (B) or MAP2 (C). Small foci are present in cerebellar Purkinje cells (D) or oligodendrocytes of the centrum semiovale (E) identified by IF for calbindin or CNPase, respectively. (F) RNA foci do not colocalize with PML bodies in cortical neurons. Bar, 5 μm, applies to all panels.

Nuclear RNA foci ranged in diameter from 0.2 to 2 μm. Resolution of these small structures required direct fluorescence detection methods. However, the autofluorescent material in brain (lipofuscin) was a complicating factor. The RNA foci were clearly distinguished from lipofuscin when the epifluorescence from three color channels was merged in a single image. As shown in FIG. 12A, the nuclear foci appeared in a single channel determined by the probe label (Texas red). Lipofuscin, which excites and emits at a broad spectrum of wavelengths, generated signal in all channels and appeared as a different color (typically yellow-brown) in the merged image. These observations formed the basis for distinguishing RNA foci in subsequent experiments. RNA foci were red, sharply demarcated structures in the nucleus. Lipofuscin was yellow-brown perinuclear material with indistinct margins.

Immunofluorescence (IF) combined with FISH: to determine which cells express mutant DMPK and form RNA inclusions, different brain regions were surveyed using FISH in combination with antibodies that mark specific cell types. In cerebral cortex, the nuclear foci were distributed throughout all cortical layers and were confined to neurons, as determined by immunofluorescence (IF) for neuronal markers NeuN (FIG. 12B) or MAP2 (FIG. 12C).

| Target Antigen | Final Dilution |
| --- | --- |
| Muscleblind (MBNL1) | mAb (3B10): 1:1500 |
| | pAb (EXP 42): 1:1500 |
| Muscleblind (MBNL2) | mAb (2D9): 1:10,000 |
| CUGBP1 | mAb (3B1): 1:500 |
| CELF4 | pAb (#440): 1:500 |
| ERT3 | pAb (#163): 1:1500 |
| PKR | pAb (pT451): 1:500 |
| | pAb (M515): 1:500 |
| | pAb (D20): 1:500 |
| | mAb (B10): 1:500 |
| RNA helicase A | pAb 1:500 |
| ADAR1 | mAb: 1:500 |
| HRBP | pAb (#1683): 1:500 |

-continued

| Target Antigen | Final Dilution |
|---|---|
| NF90 (DRBP76) | pAb (p90 AB4): 1:500 |
| Staufen | pAb 1:500 (AB 5819) |
| Proteasome | |
| 19S S10a | pAb: 1:500 |
| 11S α | pAb: 1:1000 |
| 11S γ | pAb: 1:1000 |
| 20S β3 (HC10) | mAb: 1:500 |
| 20S α | pAb: 1:1000 |
| Ubiquitin | pAb: 1:1000 |
| p80 coilin | pAb: (R288): 1:500 |
| C23 nucleolin | mAb: 1:500 |
| PML | pAb: 1:500 |
| PTB | pAb: 1:500 |
| PM-Scl 75 | pAb: 1:500 |
| hnRNP H | |
| C-terminal | pAb: 1:100 |
| N-terminal | pAb: 1:500 |
| hnRNP F | pAb: 1:1000 |
| hnRNP H | pAb: 1:1000 |
| hnRNP F | pAb: 1:1000 |
| hnRNPI/PTB | pAb: 1:1000 |
| KSRP | pAb: 1:1000 |
| 4F4 (hnRNP C) | mAb: 1:500 |
| 1D8 (hnRNP M) | mAb: 1:500 |
| CNPase | mAb: 1:1000 |
| MAP2 | mAb: 1:500 |
| NeuN | mAb: 1:500 |
| Sp1 (sc-59) | pAb: 1:500 |
| RARγ(sc-550) | pAb: 1:500 |
| Staufen (AB5819) | pAb: 1:500 |
| SUMO-1 | mAb |

Following the 1×SSC post-hybridization wash of the FISH procedure, sections were incubated in primary antibodies (Table 1, above) overnight at 4° C., washed five times with PBS for 2 min, and then incubated in secondary antibody (Alexa 488-labeled goat anti-rabbit polyclonal or Alexa 488-labeled goat anti-mouse polyclonal, Molecular Probes) and 33 nM diamidino-2-phenylindole (DAPI) for 30 min at room temperature. The antibody sources were as follows: CELF4 and ETR3 (T. Cooper, TX), PKR and C23 nucleolin and PML (Biosource Intl, CA), RNA helicase A (C. Lee, NJ), ADAR1 (D. Cho, PA), NF90 (G. Sen, OH), Staufen and NeuN (Chemicon, CA), proteasome (Affiniti, UK), Ubiquitin (DAKO, DK), p80 coilin (K L Chan, CA), PTB (E. Wagner, NC), PM-Scl 75 and hn RNP H and F (J. Wilusz, NJ and D. Black, CA), CNPase and MAP2 (Sigma, MO), Sp1 and RARγ (Santa Cruz Biotechnology, CA), and SUMO-1 (Zymed Laboratories, Inc., CA). Sections were washed five times in PBS prior to mounting.

To estimate relative MBNL1 concentration in nucleoplasm in DM1 nuclei vs. controls, sections of temporal cortex were processed on the same slide and imaged under the same exposure settings. Merged images for Texas red (to visualize RNA foci), Alexa 488 (for MBNL1) and DAPI (for nuclear DNA) were obtained. Regions of interest were manually defined as nuclear area excluding nucleolus, RNA foci, and overlapping lipofuscin. MBNL1 fluorescence intensity (mean optical density in monochrome mode in arbitrary units) in the region of interest was determined for 20 cortical neuronal nuclei per subject. Because of the difficulty of estimating background fluorescence from brain sections, the results are not corrected for background. This approach provides a conservative estimate of the fold-reduction for MBNL1 in DM1 nucleoplasm.

Counts of 100 NeuN-positive cells from temporal and frontal cortex of 4 patients with classical DM1 (selected for best relative preservation of cortical architecture) showed RNA foci in >85% of cortical neurons in each case. More than one focus was visible in ~30% of cortical neurons, and occasional neurons had up to 15 small foci. In contrast, the individual having a small CTG repeat expansion (77 repeats) and mild phenotype (cataracts, mild weakness, and cognitive impairment after age 60 years) had foci in only 39% of NeuN-positive neurons in temporal cortex.

Example 10

FISH and IF Analysis of Other Neuronal Populations in DM1

Figure 13:
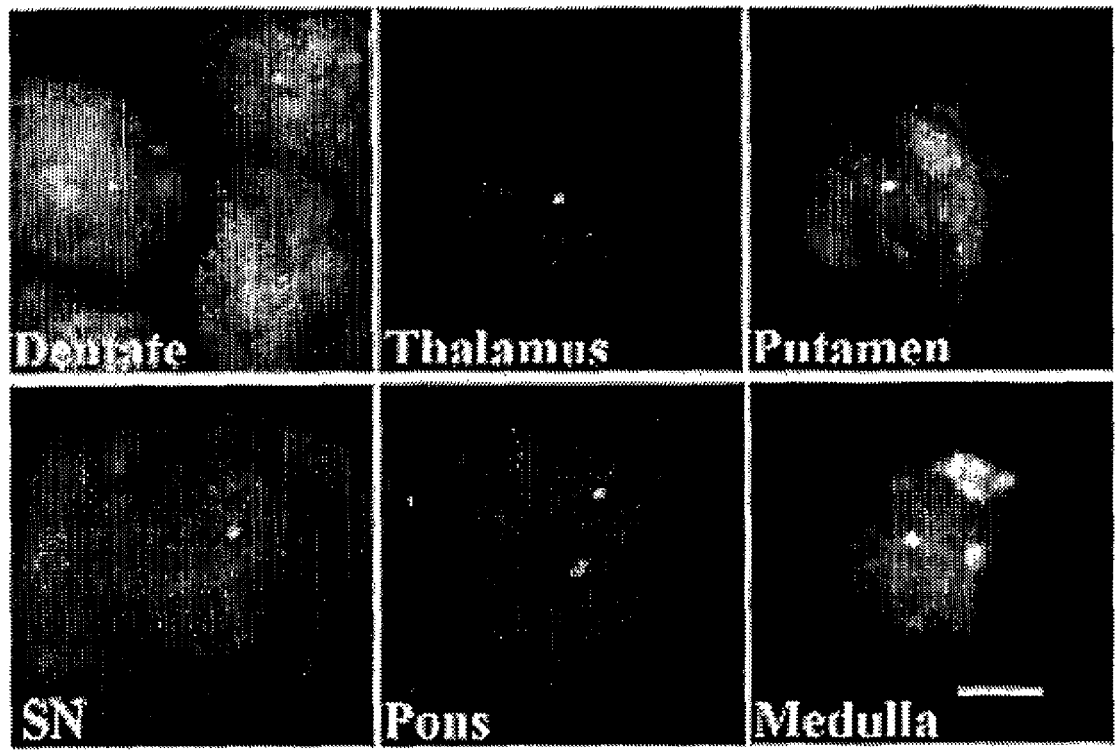
FIG. 13 shows RNA foci in dentate gyrus and subcortical neurons in DM1, as visualized by FISH and IF analysis. FISH (CAG repeat probe, red) merged with IF (anti-NeuN antibody, green) and nuclear stain (DAPI, blue). SN, substantia nigra. Bar, 5 μm, applies to all panels.

RNA foci were widely distributed in other neuronal populations, including the hippocampus (all sectors), dentate gyrus, thalamus, and also the substantia nigra and brain stem tegmentum (each of 4 patients examined) (FIG. 13). The main exception was in cerebellar cortex, where small foci were detected in some Purkinje cells but not in neurons of the molecular or granular cell layers (n=6 patients examined) (FIG. 12D).

RNA foci were also present in the subcortical white matter and corpus callosum in occasional cells expressing 2'3'-cyclic nucleotide 3'-phosphodiesterase (CNPase), a marker for oligodendrocytes (FIG. 12E). However, these foci were smaller and less intense than those in cortical neurons. In sections processed on the same slide and imaged under the same exposure settings, quantitation of FISH signals indicated that the amount of CUG expansion RNA in frontal cortical neurons was 2.9-fold greater (area×intensity) than in Purkinje cells ($p<10^{-10}$) and 18-fold greater than in oligodendrocytes ($p<10^{-10}$) within the same individual (n=3 patients, 60 nuclei per patient).

Example 11

FISH and IF Analysis of Neuronal and Muscle Populations in DM1

Figure 14:
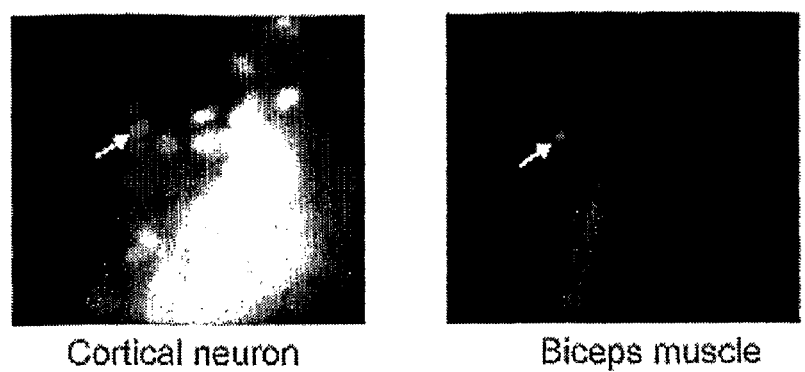
FIG. 14(A) shows foci of mutant RNA in neuronal and muscle nuclei, as visualized by FISH and IF analysis. Processing was carried out on the same slide and imaging under the same exposure settings. (B) depicts, in bar graph form, fluorescence area×intensity of RNA foci in paired samples of frontal cortex and skeletal muscle from the same patient; n=3 patients, 20 nuclei per sample ($p<10^{-10}$).
Figure 14:
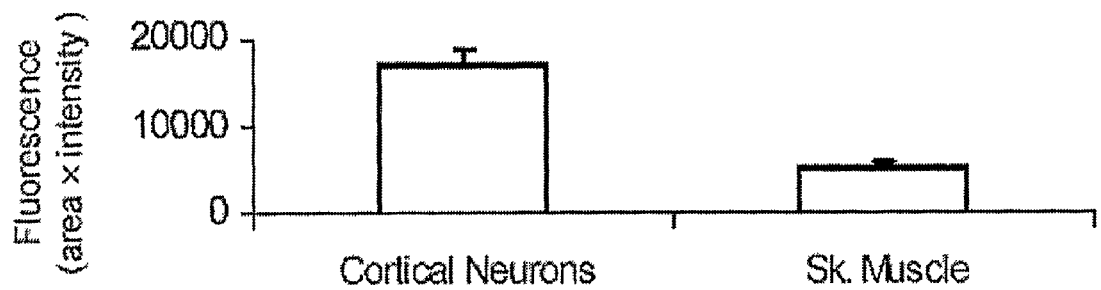

Paired samples of frontal cortex and biceps muscle were available for three patients. When sections of skeletal muscle and cerebral cortex from same patient were processed on the same slide and imaged under the same exposure settings, the RNA inclusions were larger and more intense (3.1-fold greater, area×intensity) in frontal cortical neurons than in skeletal muscle from the same individual ($p<10^{-10}$, FIG. 14).

Example 12

Localization of Mutant RNA

To determine if mutant RNA resides in a previously identified nuclear domain, mutant RNA was tested for colocalization with proteins that mark different nuclear compartments. These and subsequent experiments localizing protein relative to expanded poly(CUG) RNA were performed on a subset of 4 DM1 and 3 non-disease control samples showing the best preservation of cortical architecture. In contrast to nuclear inclusions of polyglutamine proteins (Skinner, P. J., Koshy, B. T., Cummings, C. J., Klement, I. A., Helin, K., Servadio, A., Zoghbi, H. Y., and Orr, H. T. (1997), *Nature,* 389, 971-974), RNA foci did not colocalize with PML bodies (FIG. 12F).

Colocalization of mutant RNA was likewise not found with the nucleolus (visualized by DNA staining or antibodies to C23 nucleolin), perinucleolar compartment (antibodies to polypyrimidine tract binding protein), or "speckles" (antibodies to hnRNP C) (data not shown). The possibility of colocalization with Cajal bodies cannot be eliminated, because p80 coilin antibodies did not consistently identify Cajal bodies in cortical neurons stained by the presently described methods.

Example 13

FISH and IF Analysis of Temporal and Frontal Cortical Neurons

Figure 15:
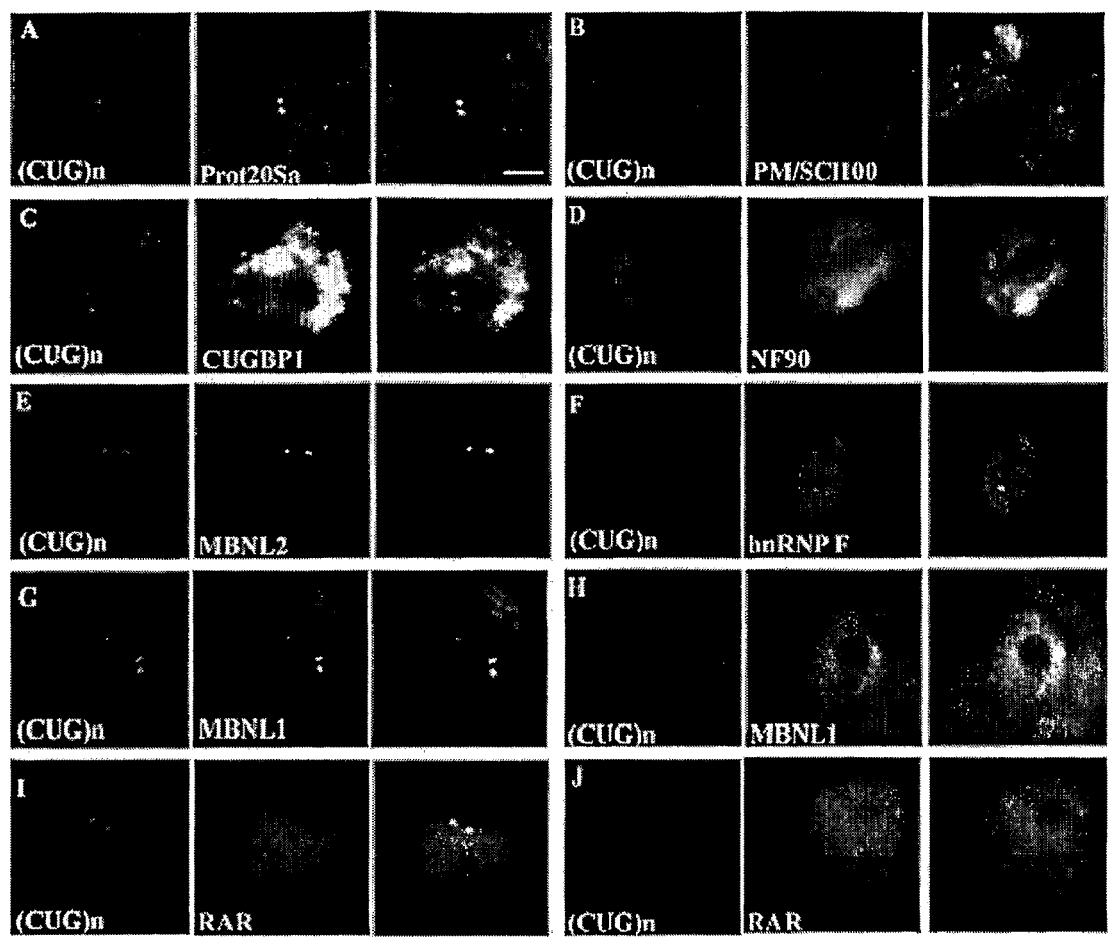
FIG. 15 shows the results of FISH and IF analyses of sections of temporal or frontal cortical neurons showing colocalization of mutant DMPK mRNA [(CUG)n] with 20Sa subunit of proteasome (A), MBNL2 (E), and hnRNP F (F). There is a marked redistribution of MBNL1 into RNA foci in DM1 cortical neurons (G), compared to the distribution in the nucleus (excluding nucleolus) and cytoplasm of normal neurons (H). Mutant DMPK mRNA does not colocalize with the PM/Scl100 (nuclear) component of the exosome (B), CUGBP1 (C), or NF90 (D). RARγ does not colocalize with RNA foci in DM1 cortical neurons (I). The distribution of RARγ in the DM1 (I) and non-neurologic-disease (J) neuronal nucleus is similar. Bar, 5 μm, applies to all panels.
Figure 16:
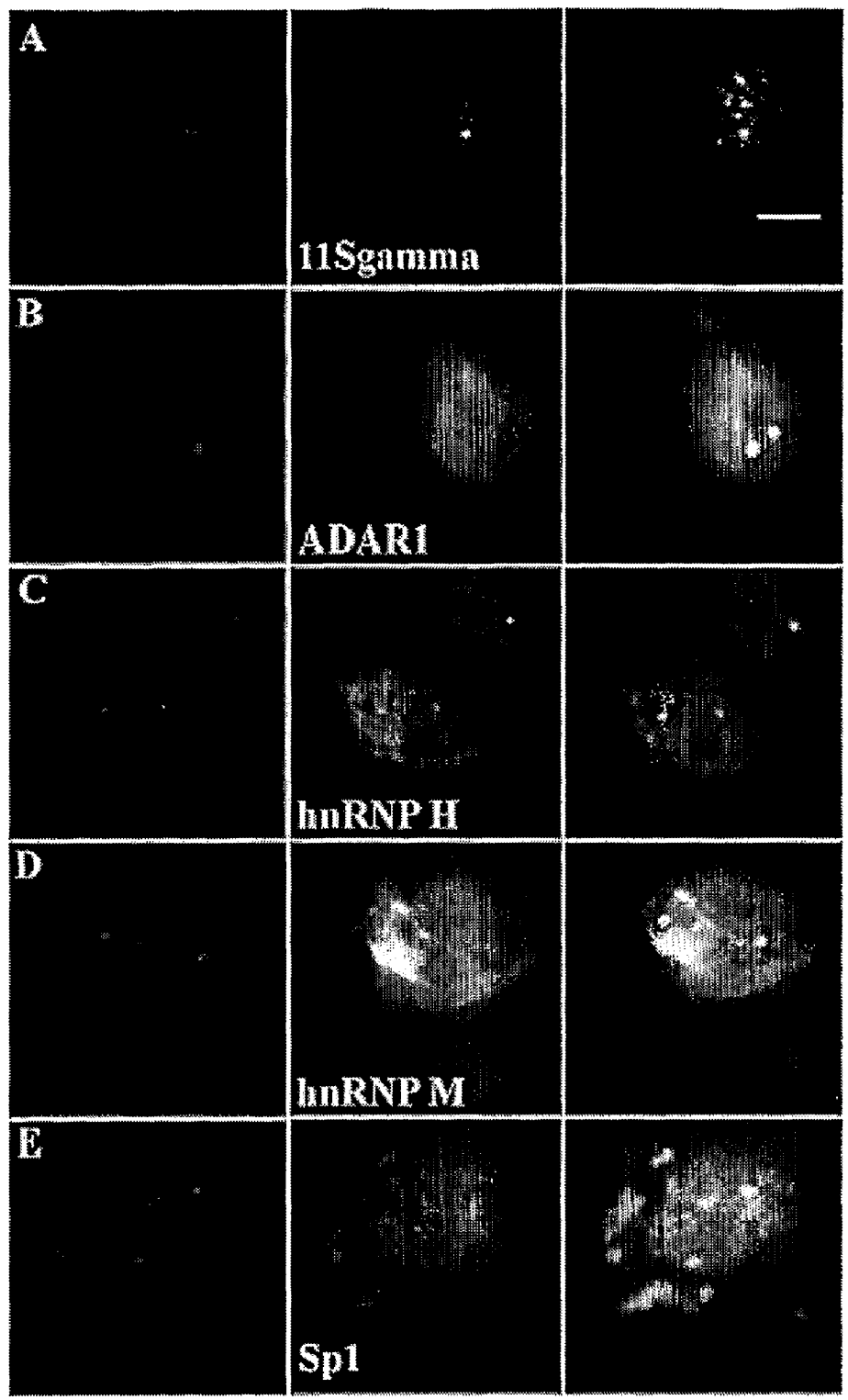
FIG. 16 shows the results of FISH analysis combined with IF analysis of sections of DM1 temporal or frontal cortex. FISH (CAG repeat probe, red, left panels) and IF (middle panels, antibody to indicated protein, green) are merged with nuclear stain (DAPI, blue) in right panels. CUG expansion RNA colocalizes with proteasome 11Sγ subunit (A) and hnRNP H (C) but not with double-stranded RNA binding protein ADAR1 (B), hnRNP M (D), or Sp1 (E). Bar, 5 μm, applies to all panels.

Recruitment of proteasome and exosome to nuclear RNA foci: the proteasome and exosome are multisubunit complexes responsible for protein and RNA degradation, respectively. To determine if these complexes are recruited to nuclear RNA foci, FISH analysis was combined with immunofluorescence using antibodies to components of the proteasome or exosome. Three components of the proteasome (20Sa, 11Sy and 11Sa subunits) were recruited to RNA foci in cortical neurons (FIG. 15A; FIG. 16A). No evidence was found, however, for ubiquitination or sumoylation of the foci (not shown). In contrast, antibodies to the PM/Scl75 or PM/Scl100 components of the exosome did not colocalize with RNA foci (FIG. 15B). This observation indicates that the proteasome may be recruited by conformational changes in MBNL1, MBNL2, or other poly(CUG) binding proteins. In such a case, loss of muscleblind function in DM1 may result from the combined effects of sequestration and accelerated degradation.

Monoclonal antibody 3B1 showed strong expression of CUGBP1 in cortical neurons (FIG. 15C). The distribution of this protein in neuronal nucleus and cytoplasm appears similar in DM1 patients and controls, and FISH/IF analysis shows that CUGBP1 is not recruited into RNA foci. Polyclonal antibodies to other members of the CUGBP1 family, ETR3 and CELF4, also fail to colocalize with foci (not shown). None of six different dsRNA binding proteins in neuronal nuclei (staufen, NF90, ADAR1, PACT, PKR, RNA helicase A) colocalize with RNA foci (representative images for NF90 are shown in FIG. 15D and ADAR1 in FIG. 16B).

The RNA binding proteins hnRNP Al, hnRNP I, hnRNP M, KSRP and HuR did not colocalize with RNA foci (representative image for hnRNP M is shown in FIG. 16D). In contrast, hnRNPs H and F colocalized with foci in cortical neurons to a limited extent (FIG. 15F, FIG. 16C), and these results were verified using two different polyclonal antibodies for each protein. The intensity of immunofluorescence for these proteins was greatest at the site of RNA foci; however, there did not appear to be significant depletion of hnRNP H or hnRNP F elsewhere in the neuronal nucleoplasm.

The splicing of neuron-specific exon N1 of c-src, which is promoted by hnRNPs H and F (Min, H., Chan, R. C., and Black, D. L. (1995), *Genes Dev.*, 9, 2659-2671; Chou, M. Y., Rooke, N., Turck, C. W., and Black, D. L. (1999), *Mol. Cell Biol.*, 19, 69-77) was not reduced in DM1 cerebral cortex. Indeed, inclusion of the N1 exon showed a slight (1.3-fold, p<0.02) increase in DM1 with respect to controls, opposite to the predicted effect of hnRNP F or H depletion (not shown). This fits with expectations that the number and density of binding sites on a single transcript, hence the capacity for protein sequestration, is much greater for proteins that bind to expanded poly(CUG) than for proteins that bind DMPK mRNA outside of the repeat tract.

Mutant DMPK mRNA is reported to interact with transcription factors retinoic acid receptor gamma (RARγ) and Sp1 (Ebralidze, A., Wang, Y., Petkova, V., Ebralidse, K., and Junghans, R. P. (2004), *Science*, 303, 383-387). In cortical neurons, these transcription factors were readily detected by immunofluorescence but they did not colocalize with RNA foci (FIGS. 15I and 16E) and their distribution was similar in DM1 patients and controls (FIGS. 15I and 15J).

Polyclonal antisera recognizing all members of the muscleblind family (MBNL1, MBNL2, and MBNL3) showed strong colocalization with RNA foci (not shown). We used monoclonal antibodies raised against epitopes specific for MBNL1 or MBNL2 to determine which muscleblind proteins interact with CUG expansion RNA in neurons. MBNL3 was not examined because its expression in adults is mainly restricted to placenta (Fardaei, M., Rogers, M. T., Thorpe, H. M., Larkin, K. Hamshere, M. G., Harper, P. S., and Brook, J. D. (2002), *Hum. Mol. Genet.*, 11, 805-814; Kanadia, R. N., Urbinati, C. R., Crusselle, V. J., Luo, D., Lee, Y. J., Harrison, J. K., Oh, S. P., and Swanson, M. S. (2003), *Gene Expr. Patterns*, 3, 459-462). In normal controls, monoclonal antibody 3A4 showed expression of MBNL1 in nuclei and cytoplasm of cortical neurons (FIG. 15H).

Figure 17:
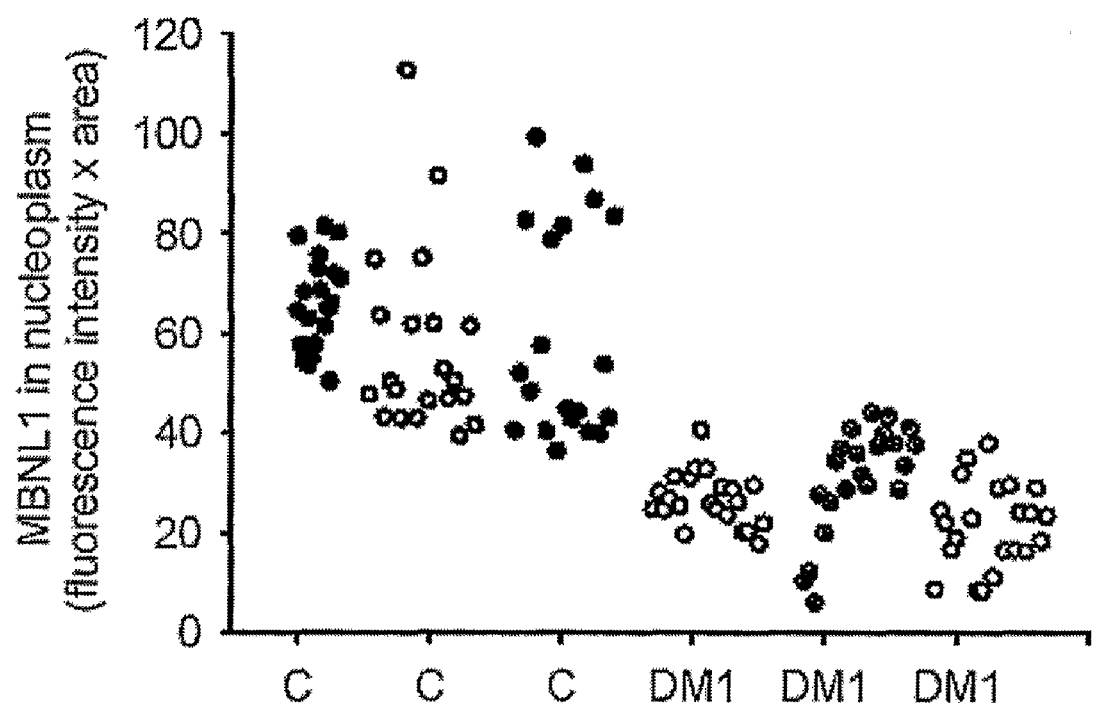
FIG. 17 depicts, in graph form, immunofluorescence (area×intensity) for MBNL1 in the nucleus, excluding nucleolus and RNA foci, as determined for 20 neurons in sections of temporal cortex from 3 individuals with DM1 and 3 controls without neurologic disease (C).

In DM1, MBNL1 was strongly recruited into RNA foci, whereas staining elsewhere in the nucleus was markedly reduced (FIG. 15G). Quantitative analysis was performed on 3 DM1 patients and non-neurologic disease controls having the shortest postmortem intervals and best preservation of cortical architecture (FIG. 17). The mean immunofluorescence intensity for MBNL1 in the nucleoplasm (excluding RNA foci and nucleoli) was 2.3-fold lower in DM1 neurons than in non-disease controls (26±9 area×intensity units in DM1 patients vs 61±17 in controls, 20 neuronal nuclei per subject, p<0.00001). Monoclonal antibody 2D9 showed that MBNL2 was also recruited into RNA foci (FIG. 15E). However, immunofluorescence signals in neurons with MoAb 2D9 were lower in relation to background staining in the neuropil, precluding a reliable quantification of its distribution. The finding of depletion of MBNL1 in the nucleoplasm of DM1 cells supports a model where CUG expansion RNA accumulates to levels sufficient to sequester and compromise the nuclear functions of MBNL1.

Example 14

DM1 and Alternative Splicing in the Brain

To determine if DM1 is associated with altered regulation of alternative splicing in brain, 45 exons (in 31 genes) known to undergo alternative splicing in brain (Table 2, below) were examined.

TABLE 2

List of exons screened for abnormal regulation of alternative splicing in DM1 compared to control without neurologic disease. "Nucleotides" indicates which portion of the specified cDNA (GenBank accession number) was amplified by RT-PCR.

| Gene Name | Unigene | Alternatively Spliced Exon | Acc. No. | Nucleotides* |
|---|---|---|---|---|
| Amyloid beta (A4) precursor protein | APP | ex2 | NM_000484 | 205-372 |
|  |  | ex7 | NM_000484 | 1013-1180 |
|  |  | ex15 | NM_000484 | 1181-1237 |
| Actin-related protein 3-beta | ARP3BETA | ex2 | BC008682.1 | 134-189 |

TABLE 2-continued

List of exons screened for abnormal regulation of alternative splicing in DM1 compared to control without neurologic disease. "Nucleotides" indicates which portion of the specified cDNA (GenBank accession number) was amplified by RT-PCR.

| Gene Name | Unigene | Alternatively Spliced Exon | Acc. No. | Nucleotides* |
|---|---|---|---|---|
| Beta-site APP-cleaving enzyme 2 | BACE2 | ex9 | NM_012105 | 1448-1597 |
| | | ex10 | NM_012105 | 1598-1766 |
| Neuronal apoptosis inhibitory protein | BIRC1 | ex10-11 | NM_004536 | 1314-1453 |
| Calcium channel, voltage-dependent, P/Q type, alpha 1A subunit | CACNA1A | ex38 | AF004883 | 5783-5879 |
| Calcium/calmodulin protein kinase II dependent delta | CAMK2D | alt splice donor in ex21(44 bp) | NM_172127 | 1709-1981 |
| Clathrin light chain B | CLTB | exon cassette | NM_007097 | 641-694 |
| Homo sapiens discs, large homolog 1 | DLG1 | ex8 | NM_004087 | 771-824 |
| Dopamine receptor type 2 | DRD2 | ex6 | NM_000795 | 889-975 |
| Erythrocyte membrane protein band 4.1-like 1 | EPB41L1 | ex5 | NM_012156 | 514-618 |
| | | ex21 | NM_012156 | 2356-2439 |
| GABA receptor alpha 2 | GABRA4 | ex3-8 | NM_000809 | 345-1274 |
| Gephyrin | GPHN | ex9 | NM_020806 | 742-840 |
| | | ex12 | NM_020806 | 976-1018 |
| LIM domain binding 3 | LDB3 | ex10 | AB 014513 | 918-1106 |
| NMDA receptor NR1 | GRIN1 | ex5 | AF015730 | 644-706 |
| | | ex20 | NM_007327 | 3683-3793 |
| | | ex21 | NM_007327 | 3794-3910 |
| Neurotrophic tyrosine kinase, receptor, type 2 | NTRK2 | exon cassette | AF410901 | 1878-1926 |
| C-Jun N-terminal kinase 2 | JNK2 | E6b, E6a | NM_002752 | 666-737 |
| Netrin G1 | Ntng2 | E5 | NM_032536 | 1115-1138 |
| Neogenin | NEO1 | ex26 | NM_002499 | 3879-4037 |
| Neurofibromin 1 | NF1 | ex9a | NT010799 | 108004-108033 |
| Neuronatin | NNAT | ex2 | NM_005386 | 200-280 |
| Neurorexin 1 | NRXN1 | ex3a | NM_004801 | 965-1024 |
| | | ex4 | | |
| | | ex5 | | |
| | | ex7a | NM_004801 | 1327-1250 |
| | | ex12 | NM_004801 | 2540-2566 |
| Neurorexin 2 | NRXN2 | ex12 | NM_015080 | 2829-2855 |
| | | ex20 | NM_015080 | 4197-4286 |
| Neurorexin 3 | NRXN3 | ex12 | NM_004796 | 1621-1647 |
| NUMB | NUMB | ex8 | AF015040 | 480-512 |
| | | ex15 | AF015040 | 1367-1510 |
| Presynaptic cytomatrix protein | PICO | ex10 | AB011131 | 3056-3082 |
| Peanut-like 2 | PNUTL2 | ex2 | NM_004574 | 189-579 |
| Protein phosphatase 2, regulatory subunit B (PR 52), beta isoform | PPP2R2B | ex6 | MN_181674 | 364-557 |
| REST/NRSF/SBR | REST | ex5 | AF228045 | 410-459 |
| Microtubule-associated protein tau | MAPT | ex2 | NM_005910 | 370-456 |
| | | ex10 | NM_005910 | 1059-1151 |
| Sarcolemma associated protein | SLMAP | ex4 | NM_007159 | 273-395 |
| v-src sarcoma (Schmidt-Ruppin A-2) viral oncogene homolog (avian) | SRC | exon cassette | NM_005417 | additional exon cassette (18 bp or 50 bp) |

*"Nucleotides" indicates which portion of the specified cDNA (GenBank accession number) was amplified by RT-PCR.

RT-PCR analysis of alternative splicing: total RNA was isolated from temporal cortex gray matter of 7 DM1 patients and 5 non-neurologic disease controls using TriReagent (Molecular Research Center, Cincinnati). cDNA was synthesized using SuperScript II reverse transcriptase (Invitrogen) with a mixture of oligo(dT)12-18 and random hexamer primers. The cDNA was digested with RNase H and then amplified using PCR primers flanking alternatively spliced exons (Table 2).

PCR products were resolved on agarose gels, stained with SybrGreenII (Molecular Probes), and analyzed on a fluorimager. An initial screen was performed on a subset of samples (4 DM1 and 2 control). Four exons appeared to show deregulated splicing in DM1. These differences were quantified in a second experiment including the full panel of 7 DM1 and 5 control samples. The fraction of exon inclusion was determined on triplicate reactions using ImageQuant software (Amersham, Piscataway).

Figure 18:
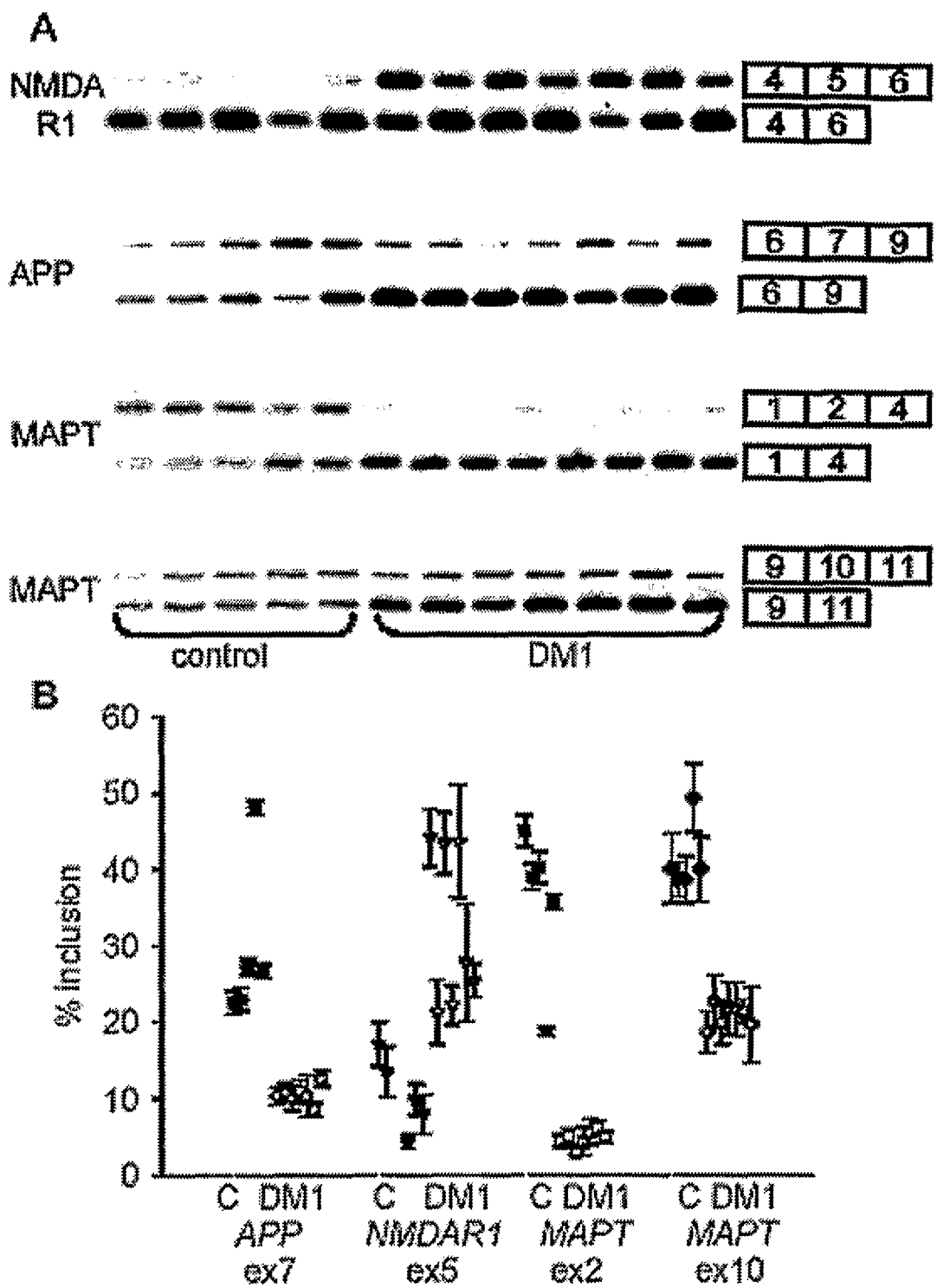
FIG. 18 shows the regulation of alternative splicing of the NMDA NR1 receptor (NMDAR1), amyloid beta precursor protein (APP), and microtubule-associated protein tau (MAPT) in DM1. (A) shows splice products obtained by RT-PCR amplification of RNA isolated from non-disease control (n=5) or DM1 (n=7) temporal cortex. Exon utilization for each splice product is shown in diagram. (B) provides quantification of RT-PCR splicing assay (triplicates). ex, exon.

For each exon, the ratio of inclusion versus exclusion isoforms was determined by reverse transcriptase PCR (RT-PCR) using primers flanking the regulated exon. An initial screen was performed using total RNA extracted from superior temporal cortex from two controls without neurological disease and four DM1 patients. Among 45 exons screened, 4 appeared to show a change in the ratio of exon inclusion/exclusion splice products in DM1. These differences were then confirmed and quantified in triplicate assays using temporal cortex RNA from 7 patients with DM1 and 5 controls (FIG. 18). DM1 was associated with decreased inclusion of amyloid precursor protein exon 7 ($10\pm1\%$ in DM1, $30\pm11\%$ in controls, $p<0.001$), increased inclusion of NMDA NR1 receptor exon 5 ($33\pm11\%$ in DM1, $11\pm5\%$ in controls, $p<0.01$), decreased inclusion of tau exon 2 ($5\pm1\%$ in DM1, $36\pm10\%$ in controls, $p<10^{-5}$), and decreased inclusion of tau exon 10 ($21\pm1\%$ in DM1, $41\pm5\%$ in controls, $p<10^{-6}$).

MBNL regulates fetal exon skipping in adults. The associated disease constitutes the failure in tissues to splice out specific fetal exons. Without MBNL, the fetal exons are retained. Other exons similarly regulated by MBNL remain to be identified.

Notably, DM1 is associated with reduced exon 10 inclusion (FIG. 18), and FTDP-17 and DM1 are both associated with neurofibrillary tangles and neuronal aggregates of hyperphosphorylated tau (Foster, N. L., Wilhelmsen, K., Sima, A. A., Jones, M. Z., D'Amato, C. J., and Gilman, S. (1997), *Ann. Neurol.*, 41, 706-715; Kiuchi, A., Otsuka, N., Namba, Y., Nakano, I., and Tomonaga, M. (1991), *Acta Neuropathol.*, 82, 1-5; Yoshimura, N., Otake, M., Igarashi, K., Matsunaga, M., Takebe, K., and Kudo, H. (1990), *Clin. Neuropathol.*, 9, 234-239; Vermersch, P., Sergeant, N., Ruchoux, M. M., Hofmann-Radvanyi, H., Wattez, A., Petit, H., Dwailly, P., and Delacourte, A. (1996), *Neurology*, 47, 711-717.

Neuronal intranuclear inclusions are characteristic of several neurological disorders. In the polyglutamine disorders, the core component of the inclusion is mutant protein or a cleavage product containing the polyglutamine tract (Davies, S. W., Turnaine, k M., Cozens, B. A., DiFiglia, M., Sharp, A. H., Ross, C. A., Scherzinger, E., Wanker, E. E., Mangiarini, L., and Bates, G. P. (1997), *Cell*, 90, 537-548; DiFiglia, M., Sapp, E., Chase, K. O., Davies, S. W., Bates, G. P., Vonsattel, J. P., and Aronin, N. (1997), *Science*, 277, 1990-1993). In Fragile X tremor ataxia syndrome (FXTAS), FMR1 mRNA having an expanded CGG repeat leads to formation of nuclear inclusions (Greco, C. M., Hagerman, R. J., Tassone, F., Chudley, A. E., Del Bigio, M. R., Jacquemont, S., Leehey, M., and Hagerman, P. J. (2002), *Brain*, 125, 1760-1771). The above-delineated results indicate that DM1 should be added to the list of disorders characterized by neuronal intranuclear inclusions.

Furthermore, in DM1 muscle tissue, evidence indicates that RNA inclusions are directly involved in disease pathogenesis, through a mechanism that involves sequestration of muscleblind proteins and mis-regulation of alternative splicing (Kanadia, R. N., Johnstone, K. A., Mankodi, A., Lungu, C., Thornton, C. A, Esson, D., Timmers, A. M., Hauswirth, W. W., and Swanson, M. S. (2003), *Science*, 302, 1978-1980; Mankodi, A., Logigian, E., Callahan, L., McClain, C., White, R., Henderson, D., Krym, M., and Thornton, C. A. (2000), *Science*, 289, 1769-1773). The strong expression of expanded poly(CUG) RNA in DM1 neurons, formation of RNA inclusions, redistribution of muscleblind proteins, and altered regulation of alternative splicing shown above indicate that CNS symptoms of DM1 may also be triggered by RNA inclusions.

Despite evidence that mutant DMPK RNA accumulates to higher levels in cortical neurons (FIG. 14), the cell degeneration is more severe in muscle. The present results also indicate that splicing abnormalities are less frequent and less severe in cerebral cortex than in skeletal muscle (FIG. 18), suggesting that muscleblind proteins are more effectively sequestered in muscle nuclei, or that compensation for muscleblind deficiency is more effective in neurons, perhaps due to expression of additional RNA binding proteins. The exact determinants of cell vulnerability in DM1 are unknown, but the stoichiometry of CUG expansion RNA in relation to muscleblind proteins is likely to play an important role. Of note, while the present studies establish that the mutant DMPK mRNA is widely expressed in cortical and subcortical neurons, the failure to detect DMPK immunologically likely reflects its relatively low concentration in brain homogenates.

The 3-fold increase in the fraction of NMDA receptor 1 (NMDAR1) mRNA that includes exon 5 observed in DM1 brain is of significance, since inclusion of this exon influences the pharmacologic behavior, gating, and cellular distribution (somatic rather than somatodendritic expression) of NMDAR1 (Pal, R., Agbas, A., Bao, X., Hui, D., Leary, C., Hunt, J., Naniwadekar, A., Michaelis, M. L., Kumar, K. N., and Michaelis, E. K. (2003), *Brain Res.*, 994, 1-18).

NMDAR1 function is required for normal long term potentiation in the hippocampus and learning (Tsien, J. Z., Huerta, P. T. and Tonegawa, S. (1996), *Cell*, 87, 1327-1338). Thus, altered splicing of exon 5 may contribute to the memory impairment observed in DM1 (Rubinsztein, J. S., Rubinsztein, D. C., McKenna, P. J., Goodburn, S., and Holland, A. J. (1997), *J. Med. Genet.*, 34, 229-233).

Inclusion of tau exon 2 is reduced in DM1, confirming previous observations (Sergeant, N., Sablonniere, B., Schraen-Maschke, S., Ghestem, A., Maurage, C. A., Wattez, A., Vermersch, P., and Delacourte, A. (2001), *Hum. Mol. Genet.*, 10, 2143-2155). These results predict that fetal isoforms of tau (excluding exons 2, 3, and 10) are inappropriately expressed in adult DM1 brain, findings that correlate well with previous studies of tau protein in DM1 brain (Sergeant, N., Sablonniere, B., Schraen-Maschke, S., Ghestem, A., Maurage, C. A., Wattez, A., Vermersch, P., and Delacourte, A. (2001), *Hum. Mol. Genet.*, 10, 2143-2155).

Expression of human fetal tau in transgenic mice leads to formation of neurofibrillary tangles and axonopathy (Ishihara, T., Zhang, B., Higuchi, M., Yoshiyama, Y., Trojanowksi, J. Q., and Lee, V. M. (2001), *Am. J. Pathol.*, 158, 555-562). It is unclear, however, whether the extent of the tau missplicing in DM1 is sufficient to cause neuronal dysfunction. Together with the above-described finding that DM1 is associated with increased expression of fetal splice isoforms for APP (exon 7 exclusion products), it is indicated that accumulation of mutant DMPK mRNA in the neuronal nucleus compromises a specific developmental program of alternative splicing.

The methods, techniques and compositions disclosed and claimed herein can be made and executed without undue experimentation in light of the present disclosure. While the compositions and methods of this invention have been illustrated with several examples and preferred embodiments, it will be apparent to those of skill in the art that variations may be applied to the methods and compositions, in the steps or in the sequence of steps and in modifications of the compositions without departing from the concept, spirit and scope of the invention. Accordingly, the exclusive rights sought to be patented are as described in the claims below.

Additional Sequences

```
SEQ ID NO: 1
Mus musculus muscleblind-like 1 (Drosophila)
(Mbnl1), mRNA.
ACCESSION NM_020007
(bases 1 to 5588)
ORIGIN
    1 ggcgacatgc cacagtctct cgccgcagcc cgtcgagtcg
      gggcgctcgc catgctcccg 61 tgacccggac ccggccagtt ccctttcccg tggcgggcat
      cccggagtcg cgatcccaca 121 atgccccggg cagtcggggc cccggcgggc agcctgcacg
      gccacgtgag aggttggtac 181 taagaagtgc ctttcctgac gtctctgctg cttggaaccg
      cttctagagc agcctctgct 241 tttgccttgc ttgctgccag ctagactgac gacagcacat
      ccgccctcca cctctagccc 301 agacacccca tttctacttc taatcaggag aaaagctctg
      agtatctgcc attgccctag 361 gctgctttag tttagaagaa aagtttgctg aaaaagtaag
      ataccttctg ccaggaaatc 421 aaggaggaaa aaaaaaaatc attttctcga ttttgctcta
      aactgctgca tctgtctatg 481 ccaaactaat caataccgat tgcaccacca aactccatcg
      caaatcagct gtgaggagat 541 tccctgtcag acaactttgc tgaaagcagc ttggaaattc
      ggtgtcaaag ggtctgccac 601 gttttcatgc ttgcattttg ggctccaaat tggcactggg
      aaggggttac tgagcacacg 661 gctgagtcca ggcctcctct aaacacccat ctacttacag
      tcctggtatt cctctcaaaa 721 ccaaaacctc tttgaattaa cagtttcatg ctgtgaattt
      ctagcggagg tctttccctt 781 tatattgaag tcacacttt ccatgtgccg ttaaatcggg
      gacgggggaa gcagcctttc 841 ggacattttc acagttatct cacactctga gttttatcag
      ttcctatttt gtttagtttt 901 tgtcttttgt tttggttgct gatttttttt ttctattttt
      cttttctctt ttcttttctt 961 ttttctttt tgttttttcc ttttttttt tttggagagg
      ggttgggttt gttggtttca 1021 ttgaacattt aactacctgt aaaatataaa catggctgtt
      agtgtcacac caattcggga 1081 cacaaaatgg ctaacactgg aagtatgtag agagtttcaa
      aggggggactt gctcacgacc 1141 agacacggaa tgtaaatttg cacatccttc gaaaagctgc
      caagttgaaa atggacgagt 1201 aatcgcctgc tttgattcac tgaaaggtcg ttgctccaga
      gagaactgca aatatcttca 1261 tccaccccca cacttaaaaa cacagttaga gataaatggg
      cggaataact tgattcagca 1321 gaagaacatg gccatgctgg cccagcaaat gcagttagcc
      aatgccatga tgcccggtgc 1381 cccgttgcag cccgtgccaa tgttttcagt tgcaccaagc
      ttagccacca gtgcatcagc 1441 agcctttaac ccttacctgg ggcctgtttc cccaagcctg
      gttccagcag agatcttgcc 1501 gactgcacca atgttggtca cggggaatcc tggagttcca
      gtgccagcag ctgccgcagc 1561 tgctgcacag aagttaatgc ggacagacag actggaggtg
      tgtcgagagt accagcgtgg 1621 caattgcaac agaggagaaa atgactgtcg gtttgctcat
      cctgctgaca gcacaatgat 1681 tgataccaat gacaacacag tcactgtctg catggattac
      atcaagggga gatgctctcg 1741 ggaaaagtgc aaatacttcc atcctcccgc acacctgcaa
      gccaagatca aggctgccca 1801 ataccaggtc aaccaggctg cagcagcaca ggctgcagct
      actgcagctg ccatgggaat 1861 tcctcaagct gtacttcccc cattgccaaa gaggcctgct
      cttgaaaaaa ccaacggtgc 1921 caccgcagtc tttaacactg gtattttcca ataccaacag
      gctctagcca acatgcagtt 1981 acagcagcat acagcatttc tcccaccagg ctcaatattg
      tgcatgacac ccgctacaag 2041 tgttgttccc atggtgcacg gtgctacgcc agccactgtg
      tccgcagcaa caacatctgc 2101 cacaagtgtt cccttcgctg caacagccac agccaaccag
      atacccataa tatctgccga 2161 acatctgact agccacaagt atgttaccca gatgtagagc
      tgtcgtcaca aaacaatcat 2221 acaaagagga aaggacagtg tgcttgatta gagtaaggac
      gacgtcatta gccatattgt 2281 atataccgtc aagcaacaca tacaaaaatc cctcagccac
      aagacatcca catattgcat 2341 gttaaccaga agaaacgaca acatgggaac ctgctgcaca
      ctgttgccta cacactttgt 2401 acattcagtt ggtatttgtg ctgaggtgat attcctatct
      aaaacaacaa cattgtcttt 2461 cttttgtagc acagagttat gcattaaaat atgcatacgt
      aattagtttc ctatatattc 2521 atgccatctt gaaaagacag actatggtgt gaccatgatt
      ctattatgta ttggtacgtc 2581 tgtagaccaa gatataattt tttaaaaata agtttatttc
      tttcaaggtt tacaagtaac 2641 caaggtgcac cttgtattta aaatcgccgt tagagctgag
      agcgcgcatg cagagtcatt
```

-continued

```
2701 tttgtttgag agtaatattt ttactgtaat agattgtacg
     acatggtgag ggagggaact 2761 gacagatgaa tgtgccaagc aaaaccacaa ctgtgtatat
     tttaaagcac accatggctt 2821 taagtaccat gttgttaagg attctcatga agtgccatag
     actgtacatc aaattagagt 2881 attatttctt cagtgttatt gtttctggag ccacattttg
     ttgcttattt gctagtacta 2941 atcaatcaaa gggcaccatt ctttctttt ttgttttga
     aaccaaagct gtctcagaaa 3001 tggccaattt aactttacag taacaataga cagcacaaca
     caaactcaat acagataacc 3061 tttcacatac tggagatata tatgatagat atataaaatt
     attttaatgc attgtagtgt 3121 aatatttatg catactctac tatataacat gttattcaaa
     agggatatgc catttctgag 3181 acacaataac aaaaaatgtt tgaggaaatt attttgcttc
     tatttatagc ctctgtcaaa 3241 agtcaaaaga ctataaatgc tttgcagaaa tgggttcacg
     tttgcttaaa cgcttcatca 3301 cagtcacatt caaaatagtg actctaaaca aagagaacag
     cactgtcatc agatgcatga 3361 taaaccaaaa tatgaaaatg ggaaatgttt aattaaccta
     gtaattgggt gggttaagta 3421 catgggtgaa tttatatgt gattcttttg ttcagattaa
     ctgcttatag ccttagaaag 3481 ccttttaaaa aattttaaaa atagatgtgc attcagtttt
     taagaatgga ttcatccaaa 3541 ggaattcccc ttttttgtgg tttggatgtt gcagctagga
     aaggctattt ttgctctgtt 3601 cagcagttct aaaatcgctg agtaggggcc aggtcactgg
     cagttctagt gtggaatggg 3661 agaagtgaga gttctgttat agaactttcc atacttccaa
     gtttactgca agttttatg 3721 cttgagagag atgctttcta atataagact gatgtgttga
     ttttcctgat tgtactgtac 3781 atctattaaa gccttagatt attacattac gggttggaac
     ccataccaat gtaatttcaa 3841 tcgtgttaag agagtaatgg tgacttcaca tgttattgta
     gttagttacg ttatagaata 3901 ttacttattt ttcttgttaa aatgtagttt ttcatttcct
     acatttattg gattttcatt 3961 ttctattaac agttgaatac catttcagtt tttagactat
     tgttttatta gattttacca 4021 atgaattttt caaaatacaa aaaattaaa gtagtttttt
     cttcataaca tactcagttt 4081 taaattacat gtagtgtcat atgaatatcc gtattattgt
     taactaaatg atttatattt 4141 tactgattta atattacagt gtaagaatgt cagtcattgt
     tcttgtctag ttttcattaa 4201 aagaacaaag atctttata tggatatctt ataaatatat
     aatcattgct aagtaagaag 4261 ttaagttgtt gctatggcaa caatcctggc agacaattga
     gtaatatttt gatgatttat
```

-continued

```
4321 tttgtttgta attagttatt atgagaagat ctagatccta
     gatattagaa taaaatttat 4381 tttctactgt atccatttca aatgttaaag tattgtttaa
     tattttgaa atccctgaat 4441 atcaggcctt gttataaata agctgcataa tcaataaata
     gaacaaggga cttttttgttg 4501 ataatccaaa tactcaaagt ttacgtaatg agaattttag
     cgtgtgtgca aactcttgag 4561 ggttgatgat gctgcaattt agcatgttgg aaagtctaga
     gagaaggttg acttttttgca 4621 cttctgtata tagtcaaaag agagaaacct gtataatagc
     aagatcttat tttgaataaa 4681 aacgtctata attacaagga gttttgttaa ggctaatgaa
     atgacagact gagcaaaatt 4741 gcttgcaaaa gtggcacaga gttagcactc catacccttc
     aaacacgtcg ctttgctttt 4801 tgtggacagc ttgtagtttg ccaggatttt tcagctggaa
     agatttgcca tccttccaag 4861 atctcatgac tgacaaaact ccattgggcc aaatctgcct
     gaagatcatt accaaaaaat 4921 agcaggtact tcagccacta agatgaaatc atggatcaga
     tatcccttac attgttttca 4981 aaactactgc atgtttaaaa cttcaacaaa aagagagaaa
     gaactatgct aaggacatat 5041 attattcaga tcgatatcta ccaatttcag tggtttaatg
     ttcacaaaat gaaatcttga 5101 aaataactat tgactttcac aaaattttaa ccataaacag
     gcaaaccaaa cagcacacct 5161 gtagttgttc tgtgattgtt ttttaattgc tgtagatcat
     gttctttccg caggtggaaa 5221 aaaaaaaaaa aaaaaaaaaa gaagttcaaa tttcacagtt
     ttaattttca actcagaagc 5281 aaaagagcaa aatgtgacaa tggccacttg tttaatgact
     tggttgccca gctgtcactg 5341 cagctggcta ctgatgttgc acttaccagc aacccaccca
     ccttcatctg ccgaaaggac 5401 agtgagcttg gttttacgat tatgtaatca caacttactt
     tctgcttgta gtggcttaaa 5461 attatgtatt ttgtctaggg ctgcaatttg ttttatgctt
     actttattat tactgcagta 5521 gttgacttttg ctgtatggaa aaataaagcg aaattgccct
     aataaaactt ctctttctta 5581 agtaaaaa
```

SEQ ID NO: 2
*Mus musculus* muscleblind-like 2 (Mbnl2),
transcript variant 2, mRNA.
ACCESSION NM_207515
(bases 1 to 4527)
ORIGIN

```
  1 agcagtggta acaacgcaga gtacgggggg tgggaaggaa
    gggctgcagc tcacagcaac 61 agagtttaga ctgtctttgc ttcatcatct gaaggtaaaa
    ttttccagcc acggccggcg 121 gctcgcagag tacaataaac agggacggag aactatttgc
    atggaccccc cttcctcatg
```

```
 181 atgcggtgga gaagccacgg ccactcggtc ctgccagatg
     ttcttggggt tactgtacat 241 ggggaagacg agcagagcta acaagaatt taaagaggac
     gaaggaagga aagcgccatc 301 ctgctcaaat acaaagatct aagagggttg ttttcccaca
     tcctccaaag ctgtgagcat 361 tagaactaat attttcccaa agagtgccat cgtattaaag
     ccactttatt aaggagggt 421 gtatctgcaa aacagtcaag agactagaac cctgggagcc
     agagatgaca gtgagcacgc 481 actgcttgtg gctcacagtc ttccagtggg gcctatcgat
     cggtgactga cttcctgctt 541 gctgacacat tcccctccc cggtttcctg gattggactg
     cattaaagaa ttcactgctt 601 accttcaaac ttacatgttg gagttttcac ggcggttgtt
     ttgagatcat tgagactcgg 661 attgatttcg acatttaacc gaaaggaaca gagcccaaag
     tagttctcat catggccttg 721 aacgttgccc ccgtgagaga cacaaagtgg ctgacgctgg
     aggtctgcag acagtaccag 781 agaggaacgt gctcacgctc cgacgaagaa tgcaagtttg
     ctcaccccc caaaagttgc 841 caggttgaaa atggaagagt aattgcctgc tttgattccc
     tcaagggccg ctgttcaaga 901 gagaactgca aatatcttca tcctccgaca cacttaaaaa
     cccagctaga gattaatggg 961 aggaacaatt tgatccagca aaaaactgca gcagcgatgc
     ttgcccagca gatgcaattt 1021 atgtttccag gaacgccgct ccatcctgtg cccactttc
     ctgtaggtcc caccatagg 1081 acaaatgcgg ctattagctt tgctccttac ttagcgcctg
     tcaccctgg agttgggtta 1141 gtcccaacag aggttctacc cactacaccg gtcattgttc
     ccggaagtcc accggtcact 1201 gtcccgggct caactgcaac tcagaaactt ctcaggactg
     ataaactgga ggtatgcagg 1261 gagttccagc gaggaaactg tgcccgggga gagacagact
     gccgctttgc acacccggca 1321 gacagcacca tgatcgacac aaacgacaac accgtaaccg
     tttgtatgga ttacataaag 1381 gggcgttgca tgagggagaa atgcaaatat tttcaccctc
     ctgcacactt gcaggccaaa 1441 atcaaagctg cgcagcacca agccaaccag gccgcggtgg
     ccgcccaggc agccgcggcc 1501 gcggccacag tcatggcctt ccctccgggt gctcttcatc
     ccttaccaaa gagacaagca 1561 cttgaaaaaa gcaacgggc cagcacggtc ttcaacccca
     gcgtcttgca ctaccagcag 1621 gctctgacca gtgcgcagct gcagcagcac acggcgttca
     tcccacagt acccatgatg 1681 cacagcgcta cgtccgccac tgtctctgca gcaacaactc
     ctgcaacaag tgtcccctcc 1741 gcagcaacag ccacagccaa tcagataatt ctgaataat
     caacagaaat ggaatggaat
```

```
1801 gccaagaatc tgcattgaga ataactaaac attgttactg
     tacatattac cccgtttcct 1861 cctcaataga attgccacaa actgcatgct aaatttagtt
     cttctggaca gaccacaacc 1921 ctaaggctag ttctgctatg tcatatatga gtattaaata
     tggtatgctt agtatactcc 1981 agcctaagat agttaaccac ctgagaccag ctgtgatgtt
     cgaagacata caggatgagg 2041 ttttctttca cagggttctg agcatagttt ctgtcccagg
     aatattgtct tatctccata 2101 actatagctg atgcagaaag tccagacaat atactcattt
     cgactcagaa tatttcaaat 2161 ttagcaataa acagttagct ttagttttaa gtacctattc
     caagggcagg ttcgattgta 2221 actccaatca caaccatttc atttcctgac tggatcgaag
     ggtatgattc acttcttgag 2281 gagacggaca gtcgcagcag agagaagtga agtaaaacat
     acgcctgcct cgcaggtcta 2341 aagtctgagt ggcagctcaa gcacaattgc caggggacac
     atcagagtgt ggggttcgct 2401 ttgccaggag atgccgcact gaatcatggg attctagaat
     aacattgcat agattgaaaa 2461 aaaaaaaaaa actttgcacg tatgagctt catacccaac
     ccaacaaagt cttgaaggta 2521 ttattttaca agtatatttt taaagttgtt ttataagaga
     gactttgtag aagtgcctag 2581 attttgccag acttcatcca gcttgacaag aatgaaaggc
     tcatgccaat agtcgaatct 2641 aagggattgg tctttcaaac tcgccctccg gttgcctgtt
     accgaataac tcttctaaac 2701 taaaacctag tcaaacaggg aagctgtagg tgaggaggtc
     tgtataatat tccagtttaa 2761 gtacgtctga gtttagtcac tacagatgca aactgtgact
     ttaatctaaa ttactatgta 2821 aacgaaaaaa aaaagtagat agtttcactt tttaaaaact
     ccattactgt ttttgcattt 2881 taagagttgg attaaagggt tgtaagtaac tgcagcatgg
     aaaaatagtt cttttaattc 2941 tttcaccta aagcatattt tatgtctcaa agtataaaa
     aactttaata caagtacaca 3001 catattatat atacacatac atatatatac tatatatgga
     tgaaacatat tttaatgttg 3061 tttacttttt ttaaatactt ggttgatctt caaggtaata
     gcgatacaat taaatttgt 3121 tcagaaagtt tgttttaaag tttattttaa gcactatcgt
     accaaatatt tcatatttca 3181 catttatat gttgcacata gcctacacag tacctacata
     gttttaaat tattgtttaa 3241 gaaatgaaac agctgttata aatggatatt atgtgtaatt
     gtttaaaaca tccatttct 3301 ttgtgaacat tttagtgatt gaagtatttt gacttttgag
     attgaatgta aaatatttta 3361 aattttggta tcatcgcctg ttctgaaaac tagaggcatc
     caaccatatc attttttttg
```

-continued

```
3421 attgaaaaaa gatctgcatt taattcatgt tggtcaaagt
     ctaattacta tttatcttac 3481 atcatagatc tgataactgt atcgaaaaga gaaatcacat
     tctgagtgta atccttgcata 3541 gtgcttgtgt cgtgtttgtt tttaatttgt ggaaaggtat
     tgtatctaac ttgtatcacc 3601 ttgatagttc tcatctttat gtattattga tatttgtaat
     ttcctcagct ataacaatgt 3661 agttacgcta caacttgcct aaaacactca tacttttttt
     tttctttact tactcattta 3721 aactcattga gaagatagta gactaaaaag gtaaattatg
     ggaatcactg aaatattttt 3781 gtagactaat tgttgtaact gtcctttctt cctttcattt
     catgattttt attttaaaaa 3841 ttattagcac atagctattt tcagcccttt aataactgat
     catcaaaaca tcacctgtat 3901 cccccagcca atatagatga ctgtattttt tactatgata
     tccattttcc agaattgtga 3961 ttataatatg cagagtcaaa tatgccattt acaataagga
     ggaggccagg caaatgcata 4021 gatgtacaaa tatatgtaca acagattttg cttttfattt
     atttataatg taattttata 4081 gaataattct gggatttgag aggatctaaa actattttc
     tgtataaata ttatttgcca 4141 aaagtttgtt tatattcaga agtctgacta tgatggataa
     atcttaaatg ctttgtttaa 4201 ttacaaaaac aaaatcacca atatccaaga caggaagatc
     tcagttcaac agctccggta 4261 gttagggaac taactccact tgcacaggac ttcatttcac
     tcttggtttt caggctataa 4321 cagcacttca cagaactatt cttcagcca tacaccactg
     gtcacatttc tactaaatct 4381 ttctgtaaca cttcttaaag aattccctca ttcgttatct
     tacagtgtaa acaggactct 4441 aatttgtatc aattatatgt tttggttgta atattcagtt
     cactcaccca atgtacaacc 4501 aatgaaataa aagaagcatt taaaagg
```

SEQ ID NO: 3
*Mus musculus* muscleblind-like 3 (*Drosophila*)
(Mbnl3), mRNA.
ACCESSION NM_134163
(bases 1 to 1967)
ORIGIN

```
   1 ctgaaggatc acgtaactca gaaaatctaa acacattat
     gtgtccaaat cagttcttct 61 gagttacgcg gacgcgtggg tttcacgacg caagtgcgtc
     ctacaggaag aaagtgcccc 121 cagtcggagc gcgagcagga gcgcgacttt tggcgctct
     ttgcgagcga gccgcaagga 181 ggcggaagac ggtcccgggc cggggcgcgg gaatcggggc
     agcgagcgcc gcacggggga 241 gttcctgcgc gtggcgtcct gcagcgaga cgccgctgga
     gtcgctcact cggagagatt 301 ccttgaacca tctgcagtca taatattctc tgaagagggt
     gcacttgatt gccaatttgc 361 tctcagtatg acacctgtca atgtagctct aatccgtgat
     accaagtggc tgactttaga 421 agtctgtaga gaattcaga gaggaacttg ctctcgagct
     gatgcagagt gcaggtttgc 481 ccatccgcca agagtttgcc atgtggaaaa tggccgagtg
     gtggcctgtt ttgattcact 541 aaagggtcgg tgcactcgtg agaactgcaa gtacctccac
     cctccaccgc acttaaagtc 601 gcagctagaa gttaatggga gaaacaatct gattcaacag
     aagactgccg cagccatgtt 661 cgcccagcac atgcaactca tgctgcagaa cgctcagatg
     tcatctcttg cgtcttttcc 721 tatgaatcca tcacttgcag ctaatcctgc catggctttc
     aatccttaca tgactcatcc 781 tggcatgggc ctggttcctg ctgagctttt accaaatggt
     ccggttctga tttctggaaa 841 ccctcctctt gcactgccag gagttcctgg tccaaagcca
     attcgtacag atagactgga 901 ggtttgccgt gaatttcagc gtggaaattg tacccgtggg
     gagagcgagt gccgctatgc 961 tcaccctacg gatgtttcca tgattgaagt cactgataat
     tctgtgacaa tctgcatgga 1021 ttacattaaa ggccgatgct cccgggagaa atgcaagtac
     tttcatcctc ctccccactt 1081 gcaggccaaa ctcagggcag ctcatcacca gatgaaccat
     tctgctgcca atgcaatggc 1141 cctgccgcat ggtgcacttc aactgatacc aaagaggtca
     gcccttgaca aggccaatgg 1201 tgccactcca gtctttaacc ccagtgtttt ccactgccaa
     caggctctgg ctaacatgca 1261 gattcctcag caggctttta tcccaacagt gcccatgatg
     cacggtgcta caccttccac 1321 tgtgtctaca gcaacaccac ctgccagcaa cgttccctac
     gttccaacaa ctacaggcaa 1381 ccagttgaaa tattgagcag cagagttaca gagtatcaga
     atctctcaac aagaaactcc 1441 gtgtggcctt tctatatgta ttctcgtatg tcttcttgta
     ccaacacgac aataagcatg 1501 gtgcagtcaa tatactaaag cgcatatacc tgttgacaaa
     ttcaaatttt aaaaatctgt 1561 ggagatgtta aagcaaatag aaaattaacc agtatgtgtt
     accttatacg gattcattgt 1621 atatgaatta gcatacaata tacaaccata caggtttgtc
     atgtatatga attatcagat 1681 ccatattaca tgaattttcc atatgatatg aattaccata
     ttgaatataa ctgtaaaatg 1741 ttgtgactgc tttccagtaa tggtttataa taaatgaact
     tccacagtgt actgtaggct 1801 tactgtatac tcttggtgga taaattctgt tttggaagtg
     ttaccttact gttttgttta 1861 caagatagtc tataggattg atgtagaatg taactgatat
     ttcccacacc attttcctcc 1921 attggtatat tgtattaaat tgggttctgc ttaaaaaaaa
     aaaaaaa
```

SEQ ID NO: 37
Homo sapiens amyloid beta (A4) precursor protein
(protease nexin-II, Alzheimer disease) (APP),
transcript variant 1, mRNA.
ACCESSION NM_000484
(bases 1 to 3641)
ORIGIN

```
   1 gctgactcgc ctggctctga gccccgccgc cgcgctcggg
     ctccgtcagt ttcctcggca
  61 gcggtaggcg agagcacgcg gaggagcgtg cgcgggggcc
     ccgggagacg cggcggtgg
 121 cggcgcgggc agagcaagga cgcggcggat cccactcgca
     cagcagcgca ctcggtgccc
 181 cgcgcagggt cgcgatgctg cccggtttgg cactgctcct
     gctggccgcc tggacggctc
 241 gggcgctgga ggtacccact gatggtaatg ctggcctgct
     ggctgaaccc cagattgcca
 301 tgttctgtgg cagactgaac atgcacatga atgtccagaa
     tgggaagtgg gattcagatc
 361 catcagggac caaaacctgc attgatacca aggaaggcat
     cctgcagtat tgccaagaag
 421 tctaccctga actgcagatc accaatgtgg tagaagccaa
     ccaaccagtg accatccaga
 481 actggtgcaa gcggggccgc aagcagtgca agacccatcc
     ccactttgtg attccctacc
 541 gctgcttagt tggtgagttt gtaagtgatg cccttctcgt
     tcctgacaag tgcaaattct
 601 tacaccagga gaggatggat gtttgcgaaa ctcatcttca
     ctggcacacc gtcgccaaag
 661 agacatgcag tgagaagagt accaacttgc atgactacgg
     catgttgctg ccctgcggaa
 721 ttgacaagtt ccgaggggta gagtttgtgt gttgcccact
     ggctgaagaa agtgacaatg
 781 tggattctgc tgatgcggag gaggatgact cggatgtctg
     gtggggcgga gcagacacag
 841 actatgcaga tgggagtgaa gacaaagtag tagaagtagc
     agaggaggaa gaagtggctg
 901 aggtggaaga agaagaagcc gatgatgacg aggacgatga
     ggatggtgat gaggtagagg
 961 aagaggctga ggaacccctac gaagaagcca cagagagaac
     caccagcatt gccaccacca
1021 ccaccaccac cacagagtct gtggaagagg tggttcgaga
     ggtgtgctct gaacaagccg
1081 agacggggcc gtgccgagca atgatctccc gctggtactt
     tgatgtgact gaagggaagt
1141 gtgccccatt cttttacggc ggatgtggcg gcaaccggaa
     caactttgac acagaagagt
1201 actgcatggc cgtgtgtggc agcgccatgt cccaaagttt
     actcaagact acccaggaac
1261 ctcttgcccg agatcctgtt aaacttccta caacagcagc
     cagtaccccT gatgccgttg
1321 acaagtatct cgagacacct ggggatgaga atgaacatgc
     ccatttccag aaagccaaag
1381 agaggcttga ggccaagcac cgagagagaa tgtcccaggt
     catgagagaa tggaagagg
1441 cagaacgtca agcaaagaac ttgcctaaag ctgataagaa
     ggcagttatc cagcatttcc
1501 aggagaaagt ggaatctttg gaacaggaag cagccaacga
     gagacagcag ctggtggaga
1561 cacacatggc cagagtggaa gccatgctca atgaccgccg
     ccgcctggcc ctggagaact
1621 acatcaccgc tctgcaggct gttcctcctc ggcctcgtca
     cgtgttcaat atgctaaaga
1681 agtatgtccg cgcagaacag aaggacagac agcacaccct
     aaagcatttc gagcatgtgc
1741 gcatggtgga tcccaagaaa gccgctcaga tccggtccca
     ggttatgaca cacctccgtg
1801 tgatttatga gcgcatgaat cagtctctct ccctgctcta
     caacgtgcct gcagtggccg
1861 aggagattca ggatgaagtt gatgagctgc ttcagaaaga
     gcaaaactat tcagatgacg
1921 tcttggccaa catgattagt gaaccaagga tcagttacgg
     aaacgatgct ctcatgccat
1981 cttTgaccga aacgaaaacc accgtggagc tccttcccgt
     gaatggagag ttcagcctgg
2041 acgatctcca gccgtggcat tcttttgggg ctgactctgt
     gccagccaac acagaaaacg
2101 aagttgagcc tgttgatgcc cgccctgctg ccgaccgagg
     actgaccact cgaccaggtt
2161 ctgggttgac aaatatcaag acggaggaga tctctgaagt
     gaagatggat gcagaattcc
2221 gacatgactc aggatatgaa gttcatcatc aaaaattggt
     gttctttgca gaagatgtgg
2281 gttcaaacaa aggtgcaatc attggactca tggtgggcgg
     tgttgtcata gcgacagtga
2341 tcgtcatcac cttggtgatg ctgaagaaga aacagtacac
     atccattcat catggtgtgg
2401 tggaggttga cgccgctgtc acccccagagg agcgccacct
     gtccaagatg cagcagaacg
2461 gctacgaaaa tccaacctac aagttctttg agcagatgca
     gaactagacc cccgccacag
2521 cagcctctga agttggacag caaaaccatt gcttcactac
     ccatcggtgt ccatttatag
2581 aataatgtgg gaagaaacaa acccgtttta tgatttactc
     attatcgcct tttgacagct
2641 gtgctgtaac acaagtagat gcctgaactt gaattaatcc
     acacatcagt aatgtattct
2701 atctctcttt acattttggt ctctatacta cattattaat
     gggtttttgtg tactgtaaag
2761 aatttagctg tatcaaacta gtgcatgaat agattctctc
     ctgattattt atcacatagc
2821 cccttagcca gttgtatatt attcttgtgg tttgtgaccc
     aattaagtcc tactttacat
2881 atgctttaag aatcgatggg ggatgcttca tgtgaacgtg
     ggagttcagc tgcttctctt
2941 gcctaagtat tccttTcctg atcactatg attttaaagt
     taaacatttt taagtatttc
3001 agatgcttta gagagatttt ttttccatga ctgcattttTa
     ctgtacagat tgctgcttct
3061 gctatatttg tgatatagga attaagagga tacacacgtt
     tgtttcttcg tgcctgtttt
```

-continued

```
3121 atgtgcacac attaggcatt gagacttcaa gcttttcttt
     ttttgtccac gtatctttgg 3181 gtctttgata agaaaagaa tccctgttca ttgtaagcac
     ttttacgggg cgggtgggga 3241 ggggtgctct gctggtcttc aattaccaag aattctccaa
     aacaattttc tgcaggatga 3301 ttgtacagaa tcattgctta tgacatgatc gctttctaca
     ctgtattaca taaataaatt 3361 aaataaaata accccgggca agacttttct ttgaaggatg
     actacagaca ttaaataatc 3421 gaagtaattt tgggtgggga aagaggcag attcaatttt
     ctttaaccag tctgaagttt 3481 catttatgat acaaaagaag atgaaaatgg aagtggcaat
     ataaggggat gaggaaggca 3541 tgcctggaca aacccttctt ttaagatgtg tcttcaattt
     gtataaaatg gtgttttcat 3601 gtaaataaat acattcttgg aggagcaaaa aaaaaaaaaa a
```

SEQ ID NO: 38
*Homo sapiens* NMDAR1 subunit isoform 3b
(hNMDARF-3b) mRNA, complete cds.
ACCESSION AF015730
(bases 1 to 3150)
ORIGIN

```
   1 aagcttatcg atccgtcgac ctcgaggggg ggcccgcgtt
     cgccgcgcag agccaggccc 61 gccgggcgag cccatgagca ccatgcgcct gctgacgctc
     gccctgctgt tctcctgctc 121 cgtcgcccgt gccgcgtgcg accccaagat cgtcaacatt
     ggcgcggtgc tgagcacgcg 181 gaagcacgag cagatgttcc gcgaggccgt gaaccaggcc
     aacaagcggc acggctcctg 241 gaagattcag ctcaatgcca cctccgtcac gcacaagccc
     aacgccatcc agatggctct 301 gtcggtgtgc gaggacctca tctccagcca ggtctacgcc
     atcctagtta gccatccacc 361 tacccccaac gaccacttca ctcccacccc tgtctcctac
     acagccggct tctaccgcat 421 accgtgctg gggctgacca cccgcatgtc catctactcg
     gacaagagca tccacctgag 481 cttcctgcgc accgtgccgc cctactccca ccagtccagc
     gtgtggtttg agatgatgcg 541 tgtgtacagc tggaaccaca tcatcctgct ggtcagcgac
     gaccacgagg gccgggccgc 601 tcagaaacgc ctggacgc tgctggagga gcgtgagtcc
     aagagtaaaa aaaggaacta 661 tgaaaacctc gaccaactgt cctatgacaa caagcgcgga
     cccaaggcag agaaggtgct 721 gcagtttgac ccaggaccaa gaacgtgac ggccctgctg
     atggaggcga aagagctgga 781 ggcccgggtc atcatccttt ctgccagcga ggacgatgct
     gccactgtat accgagcagc 841 cgcgatgctg aacatgacgg ctccgggta cgtgtggctg
     gtcggcgagc gcgagatctc 901 ggggaacgcc ctgcgttacg ccccggacgg catcctcggg
     ctgcagctca tcaacggcaa 961 gaacgagtcg gcccacatca gcgacgccgt aggcgtggtg
     gcccaggccg tgcacgagct 1021 cctcgagaag gagaacatca ccgacccgcc gcggggctgc
     gtgggcaaca ccaacatctg 1081 gaagaccggg ccgctcttca gagagtgct gatgtcttcc
     aagtatgcgg atgggggtgac 1141 tggtcgcgtg gagttcaatg aggatgggga ccggaagttc
     gccaactaca gcatcatgaa 1201 cctgcagaac cgcaagctgg tgcaagtggg catctacaat
     ggcacccacg tcatccctaa 1261 tgacaggaag atcatctggc caggcggaga gacagagaag
     cctcgagggt accagatgtc 1321 caccagactg aagattgtga cgatccacca ggagcccttc
     gtgtacgtca agcccacgct 1381 gagtgatggg acatgcaagg aggagttcac agtcaacggc
     gacccagtca agaaggtgat 1441 ctgcaccggg cccaacgaca cgtcgccggg cagcccccgc
     cacacggtgc ctcagtgttg 1501 ctacggcttt tgcatcgacc tgctcatcaa gctggcacgg
     accatgaact tcacctacga 1561 ggtgcacctg gtggcagatg gcaagttcgg cacacaggag
     cgggtgaaca acagcaacaa 1621 gaaggagtgg aatgggatga tgggcgagct gctcagcggg
     caggcagaca tgatcgtggc 1681 gccgctaacc ataaacaacg agcgcgcgca gtacatcgag
     ttttccaagc ccttcaagta 1741 ccaggggctg actatgctgg tcaagaagga gattcccggg
     agcacgctgg actcgttcat 1801 gcagccgttc cagagcacac tgtggctgct ggtggggctg
     tcggtgcacg tggtggccgt 1861 gatgctgtac ctgctggacc gcttcagccc cttcggccgg
     ttcaaggtga acagcgagga 1921 ggaggaggag gacgcactga ccctgtcctc ggccatgtgg
     ttctcctggg gcgtcctgct 1981 caactccggc atcggggaag gcgcccccag aagcttctca
     gcgcgcatcc tgggcatggt 2041 gtgggccggc tttgccatga tcatcgtggc ctcctacacc
     gccaacctgg ccgctttcct 2101 ggtgctggac cggccggagg agcgcatcac gggcatcaac
     gaccctcggc tgaggaaccc 2161 ttctgacaag tttatctact ccacggtgaa gcagagctcc
     gtggatatct acttccgggc g 2221 ccaggtggag ctgagcacca tgtaccggca tatggagaag
     cacaactacg agagtgcggc 2281 ggaagccatc caggccgtga gagacaacaa gctgcatgcc
     ttcatctggg actcggcggt 2341 gctggagttc gaggcctcgc agaagtgcga cctggtgacg
     actggagagc tgtttttccg 2401 ctcgggcttc ggcataggca tgcgcaaaga cagcccctgg
     aagcagaacg tctccctgtc 2461 catcctcaag tcccacgaga atggcttcat ggaagacctg
     gacaagacgt gggttcggta 2521 tcaggaatgt gactcgcgca gcaacgcccc tgcgaccctt
     acttttgaga acatggccgg
```

-continued

```
2581 ggtcttcatg ctggtagctg ggggcatcgt ggccgggatc
     ttcctgattt tcatcgagat 2641 tgcctacaag cggcacaagg atgctcgccg aagcagatg
     cagctggcct ttgccgccgt 2701 taacgtgtgg cggaagaacc tgcagcagta ccatcccact
     gatatcacgg gcccgctcaa 2761 cctctcagat ccctcggtca gcaccgtggt gtgaggcccc
     cggaggcgcc cacctgccca 2821 gttagcccgg ccaaggacac tgatgggtcc tgctgctcgg
     gaaggcctga gggaagccca 2881 cccgccccag agactgccca ccctgggcct cccgtccgtc
     cgcccgccca ccccgctgcc 2941 tggcgccacc ctgctggacc aaggtgcgga ccggagcggc
     tgaggacggg gcagagctga 3001 gtcggctggg cagggcgcag gcgcgtgcac ggcagaggca
     gggcctgggg tctctgagca 3061 gtggggagcg ggggctaact ggcccaggcg agggccttg
     gagcagagac ggcagcccca 3121 tccttcccgg cagcaccagc gtgagggcca
```

SEQ ID NO: 39
Homo sapiens microtubule-associated protein tau
(MAPT), transcript variant 2, mRNA.
ACCESSION NM_005910 NM_173727
(bases 1 to 2796)
ORIGIN

```
   1 cctcccctgg ggaggctcgc gttcccgctg ctcgcgcctg
     ccgcccgccg gcctcaggaa 61 cgcgccctct cgccgcgcgc gccctcgcag tcaccgccac
     ccaccagctc cggcaccaac 121 agcagcgccg ctgccaccgc ccaccttctg ccgccgccac
     cacagccacc ttctcctcct 181 ccgctgtcct ctcccgtcct cgcctctgtc gactatcagg
     tgaactttga accaggatgg 241 ctgagccccg ccaggagttc gaagtgatgg aagatcacgc
     tgggacgtac gggttggggg 301 acaggaaaga tcaggggggc tacaccatgc accaagacca
     agagggtgac acggacgctg 361 gcctgaaaga atctcccctg cagaccccca ctgaggacgg
     atctgaggaa ccgggctctg 421 aaacctctga tgctaagagc actccaacag cggaagatgt
     gacagcaccc ttagtggatg 481 agggagctcc cggcaagcag ctgccgcgc agccccacac
     ggagatccca gaaggaacca 541 cagctgaaga agcaggcatt ggagacaccc ccagcctgga
     agacgaagct gctggtcacg 601 tgacccaagc tcgcatggtc agtaaaagca agacgggac
     tggaagcgat gacaaaaaag 661 ccaggggggc tgatggtaaa acgaagatcg ccacaccgcg
     gggagcagcc cctccaggcc 721 agaaggggca ggccaacgcc accaggattc agcaaaaac
     cccgcccgct ccaaagacac 781 caccagctc tggtgaacct ccaaaatcag gggatcgcag
     cggctacagc agcccggct 841 ccccaggcac tcccggcagc cgctcccgca cccgtcccct
     tccaacccca cccacccggg
```

-continued

```
 901 agcccaagaa ggtggcagtg gtccgtactc cacccaagtc
     gccgtcttcc gccaagagcc 961 gcctgcagac agccccgtg cccatgccag acctgaagaa
     tgtcaagtcc aagatcggct 1021 ccactgagaa cctgaagcac cagccgggag gcgggaaggt
     gcagataatt aataagaagc 1081 tggatcttag caacgtccag tccaagtgtg gctcaaagga
     taatatcaaa cacgtcccgg 1141 gaggcggcag tgtgcaaata gtctacaaac cagttgacct
     gagcaaggtg acctccaagt 1201 gtggctcatt aggcaacatc catcataaac aggaggtgg
     ccaggtggaa gtaaaatctg 1261 agaagcttga cttcaaggac agagtccagt cgaagattgg
     gtccctggac aatatcaccc 1321 acgtccctgg cggaggaaat aaaaagattg aaacccacaa
     gctgaccttc cgcgagaacg 1381 ccaaagccaa gacagaccac ggggcggaga tcgtgtacaa
     gtcgccagtg gtgtctgggg 1441 acacgtctcc acggcatctc agcaatgtct cctccaccgg
     cagcatcgac atggtagact 1501 cgccccagct cgccacgcta gctgacgagg tgtctgcctc
     cctggccaag cagggtttgt 1561 gatcaggccc ctggggcggt caataattgt ggagaggaga
     gaatgagaga gtgtggaaaa 1621 aaaaagaata atgacccggc ccccgccctc tgcccccagc
     tgctcctcgc agttcggtta 1681 attggttaat cacttaacct gcttttgtca ctcggctttg
     gctcgggact tcaaaatcag 1741 tgatgggagt aagagcaaat ttcatctttc caaattgatg
     ggtgggctag taataaaata 1801 tttaaaaaaa aacattcaaa aacatggcca catccaacat
     ttcctcaggc aattcctttt 1861 gattcttttt tcttcccct ccatgtagaa gagggagaag
     gagaggctct gaaagctgct 1921 tctgggggat ttcaaggac tgggggtgcc aaccacctct
     ggccctgttg tggggttgt 1981 cacagaggca gtggcagcaa caaaggattt gaaaactttg
     gtgtgttcgt ggagccacag 2041 gcagacgatg tcaaccttgt gtgagtgtga cgggggttgg
     ggtggggcgg gaggccacgg 2101 gggaggccga ggcaggggct gggcagaggg gaggaggaag
     cacaagaagt gggagtggga 2161 gaggaagcca cgtgctggag agtagacatc cccctccttg
     ccgctgggag agccaaggcc 2221 tatgccacct gcagcgtctg agcggccgcc tgtccttggt
     ggccgggggt gggggcctgc 2281 tgtgggtcag tgtgccaccc tctgcagggc agcctgtggg
     agaagggaca gcgggttaaa 2341 aagagaaggc aagcctgcca ggagggttgg cacttcgatg
     atgacctcct tagaaagact 2401 gaccttgatg tcttgagagc gctggcctct tcctccctcc
     ctgcagggta gggcgcctga 2461 gcctaggcgg ttccctctgc tccacagaaa ccctgttta
     ttgagttctg aaggttggaa
```

2521 ctgctgccat gattttggcc actttgcaga cctgggactt
     tagggctaac cagttctctt 2581 tgtaaggact tgtgcctctt gggagacgtc cacccgtttc
     caagcctggg ccactggcat 2641 ctctggagtg tgtgggggtc tgggaggcag gtcccgagcc
     ccctgtcctt cccacggcca 2701 ctgcagtcac cccgtctgcg ccgctgtgct gttgtctgcc
     gtgagagccc aatcactgcc 2761 tataccctc atcacacgtc acaatgtccc gaattc SEQ ID NO: 54
Homo sapiens troponin T2, cardiac (TNNT2),
transcript variant 4, mRNA.
ACCESSION NM_001001432
(bases 1 to 1114)
ORIGIN
    1 ccccgctgag actgagcaga cgcctccagg atctgtcggc
      agctgctgtt ctgagggaga 61 gcagagacca tgtctgacat agaagaggtg gtggaagagt
      acgaggagga ggagcaggaa 121 gagcaggagg aggcagcgga agaggatgct gaagcagagg
      ctgagaccga ggagaccagg 181 gcagaagaag atgaagaaga agaggaagca aaggaggctg
      aagatggccc aatggaggag 241 tccaaaccaa agcccaggtc gttcatgccc aacttggtgc
      ctcccaagat ccccgatgga 301 gagagagtgg actttgatga catccaccgg aagcgcatgg
      agaaggacct gaatgagttg 361 caggcgctga tcgaggctca ctttgagaac aggaagaaag
      aggaggagga gctcgtttct 421 ctcaaagaca ggatcgagag acgtcgggca gagcgggccg
      agcagcagcg catccggaat 481 gagcgggaga aggagcggca gaaccgcctg gctgaagaga
      gggctcgacg agaggaggag 541 gagaacagga ggaaggctga ggatgaggcc cggaagaaga
      aggctttgtc caacatgatg 601 cattttgggg gttacatcca gaaggcccag acagagcgga
      aaagtgggaa gaggcagact 661 gagcgggaaa agaagaagaa gattctggct gagaggagga
      aggtgctggc cattgaccac 721 ctgaatgaag atcagctgag ggagaaggcc aaggagctgt
      ggcagagcat ctataacttg 781 gaggcagaga agttcgacct gcaggagaag ttcaagcagc
      agaaatatga gatcaatgtt 841 ctccgaaaca ggatcaacga taaccagaaa gtctccaaga
      cccgcgggaa ggctaaagtc 901 accggcgct ggaaatagag cctggcctcc ttcaccaaag
    atctgctcct cgctcgcacc 961 tgcctccggc ctgcactccc ccagttcccg ggccctcctg
    ggcaccccag gcagtccctg 1021 tttggaaatg gggagctggc ctaggtggga gccaccactc
     ctgcctgccc ccacacccac 1081 tccacaccag taataaaaag ccaccacaca ctga SEQ ID NO: 55
Homo sapiens troponin T3, skeletal, fast (TNNT3),
mRNA.
ACCESSION NM_006757
(bases 1 to 1000)
ORIGIN
    1 cccaccttca ccatgtctga cgaggaagtt gaacaggtgg
      aggagcagta cgaagaagaa 61 gaggaagccc aggaggaaga ggaagttcaa gaagacaccg
      cagaggagga cgcggaagag 121 gagaaaccga gacccaaact cactgctcct aagatcccag
      aaggggagaa agtggacttc 181 gatgacatcc agaagaagcg tcagaacaaa gacctaatgg
      agctccaggc cctcatcgac 241 agccactttg aagcccggaa gaaggaggag gaggagctgg
      tcgctctcaa agagagaatc 301 gagaagcgcc gtgcagagag agcggagcag cagaggattc
      gtgcagagaa ggagagggag 361 cgccagaaca gactggcgga ggaaaaggcc agaagggagg
      aggaggatgc caagaggagg 421 gcagaggacg acctgaagaa gaagaaagcg ctgtcctcca
      tgggcgccaa ctacagcagc 481 tacctggcca aggctgacca gaagagaggc aagaagcaga
      cagcccgaga gatgaagaag 541 aagattctgg ctgagagacg caagccgctc aacatcgatc
      accttggtga agacaaactg 601 agggacaagg ccaaggagct ctgggagacc ctgcaccagc
      tggagattga caagttcgag 661 tttgggggaga agctgaaacg ccagaaatat gacatcacca
      cgctcaggag ccgcattgac 721 caggcccaga agcacagcaa gaaggctggg accccagcca
      agggcaaagt cggcgggcgc 781 tggaagtaga gaggccagaa aggccctcga ggcagagacc
      ctccgccctc ttgcacacca 841 gggccgctcg tgggactcca catcctccag cccccacaat
      cctgtcaggg gtctccctga 901 cgtcctgggg gtggagaggc catcccgggg cgtcccccgc
      gtctgtgtcc ttgctgcctt 961 catccctgg ggcctgtgaa taaagctgca gaaccccctt

---

What is claimed is:

1. A method of treating myotonia in the muscle of a subject suffering from myotonia, comprising intramuscular injection of a recombinant adeno-associated virus (rAAV) vector comprising a promoter operably linked to a nucleic acid encoding a MBNL1 protein, wherein expression of the protein results in reducing myotonia in the muscle of the subject.

2. The method of claim 1, wherein treating comprises reducing the mis-splicing of the Clcn1 skeletal muscle chloride channel gene.

3. The method of claim 1, wherein treating comprises reducing the mis-splicing of the Amyloid beta (A4) precursor protein (APP) gene.

4. The method of claim 1, wherein treating comprises reducing the mis-splicing of the NMDA receptor NR1 (GRIN1) gene.

5. The method of claim 1, wherein treating comprises reducing the mis-splicing of the Microtubule-associated protein tau (MAPT) gene.

6. The method of claim 1, wherein treating comprises reducing the mis-splicing of the TNNT2 (cTNT) gene.

7. The method of claim 1, wherein the subject is human.

8. The method of claim 1, wherein the subject has RNA inclusions in neuronal cells.

* * * * *

SEQUENCE LISTING

<160> NUMBER OF SEQ ID NOS: 55

<210> SEQ ID NO 1
<211> LENGTH: 5588
<212> TYPE: DNA
<213> ORGANISM: Mus musculus -continued

```
<400> SEQUENCE: 1
ggcgacatgc cacagtctct cgccgcagcc cgtcgagtcg gggcgctcgc catgctcccg      60
tgacccggac ccggccagtt cccttttccg tggcgggcat cccggagtcg cgatcccaca     120
atgccccggg cagtcggggc cccggcgggc agcctgcacg gccacgtgag aggttggtac     180
taagaagtgc ctttcctgac gtctctgctg cttggaaccg cttctagagc agcctctgct     240
tttgccttgc ttgctgccag ctagactgac gacagcacat ccgccctcca cctctagccc     300
agacacccca tttctacttc taatcaggag aaaagctctg agtatctgcc attgccctag     360
gctgctttag tttagaagaa aagtttgctg aaaaagtaag ataccttctg ccaggaaatc     420
aaggaggaaa aaaaaaaatc attttctcga ttttgctcta aactgctgca tctgtctatg     480
ccaaactaat caataccgat tgcaccacca aactccatcg caaatcagct gtgaggagat     540
tccctgtcag acaactttgc tgaaagcagc ttggaaattc ggtgtcaaag ggtctgccac     600
gttttcatgc ttgcattttg ggctccaaat tggcactggg aagggttac tgagcacacg      660 gctgagtcca ggcctcctct aaacacccat ctacttacag tcctggtatt cctctcaaaa     720
ccaaaacctc tttgaattaa cagtttcatg ctgtgaattt ctagcggagg tctttccctt     780
tatattgaag tcacactttt ccatgtgccg ttaaatcggg gacggggaa gcagccttc       840 ggacattttc acagttatct cacactctga gttttatcag ttcctatttt gtttagtttt     900
tgtcttttgt tttggttgct gattttttt ttctatttt ctttttcttt ttcttttctt       960
tttttctttt tgtttttcc tttttttttt tttggagagg ggttgggttt gttggtttca     1020
ttgaacattt aactacctgt aaaatataaa catggctgtt agtgtcacac caattcggga    1080
cacaaaatgg ctaacactgg aagtatgtag agagtttcaa aggggacttt gctcacgacc    1140
agacacggaa tgtaaatttg cacatccttc gaaaagctgc caagttgaaa atggacgagt    1200
aatcgcctgc tttgattcac tgaaaggtcg ttgctccaga gagaactgca aatatcttca    1260
tccaccccca cacttaaaaa cacagttaga gataaatggg cggaataact tgattcagca    1320
gaagaacatg gccatgctgg cccagcaaat gcagttagcc aatgccatga tgcccggtgc    1380
cccgttgcag cccgtgccaa tgttttcagt tgcaccaagc ttagccacca gtgcatcagc    1440
agcctttaac ccttacctgg ggcctgtttc cccaagcctg gttccagcag agatcttgcc    1500
gactgcacca atgttggtca cggggaatcc tggagttcca gtgccagcag ctgccgcagc    1560
tgctgcacag aagttaatgc ggacagacag actggaggtg tgtcgagagt accagcgtgg    1620
caattgcaac agaggagaaa atgactgtcg gtttgctcat cctgctgaca gcacaatgat    1680
tgataccaat gacaacacag tcactgtctg catggattac atcaagggga gatgctctcg    1740
ggaaaagtgc aaatacttcc atcctcccgc cacctgcaa gccaagatca aggctgccca      1800
ataccaggtc aaccaggctg cagcagcaca ggctgcagct actgcagctg ccatgggaat    1860
tcctcaagct gtacttcccc cattgccaaa gaggcctgct cttgaaaaaa ccaacggtgc    1920
caccgcagtc tttaacactg gtattttcca ataccaacag gctctagcca acatgcagtt    1980
acagcagcat acagcatttc tcccaccagg ctcaatattg tgcatgacac ccgctacaag    2040
tgttgttccc atggtgcacg gtgctacgcc agccactgtg tccgcagcaa caacatctgc    2100
cacaagtgtt cccttcgctg caacagccac agccaaccag ataccataa tatctgccga     2160 acatctgact agccacaagt atgttaccca gatgtagagc tgtcgtcaca aaacaatcat    2220
acaaagagga aaggacagtg tgcttgatta gagtaaggac gacgtcatta gccatattgt    2280
atataccgtc aagcaacaca tacaaaaatc cctcagccac aagacatcca catattgcat    2340
```

```
gttaaccaga agaaacgaca acatgggaac ctgctgcaca ctgttgccta cacactttgt    2400
acattcagtt ggtatttgtg ctgaggtgat attcctatct aaaacaacaa cattgtcttt    2460
cttttgtagc acagagttat gcattaaaat atgcatacgt aattagtttc ctatatattc    2520
atgccatctt gaaaagacag actatggtgt gaccatgatt ctattatgta ttggtacgtc    2580
tgtagaccaa gatataattt tttaaaaata agtttatttc tttcaaggtt tacaagtaac    2640
caaggtgcac cttgtattta aaatcgccgt tagagctgag agcgcgcatg cagagtcatt    2700
tttgtttgag agtaatattt ttactgtaat agattgtacg acatggtgag ggagggaact    2760
gacagatgaa tgtgccaagc aaaaccacaa ctgtgtatat tttaaagcac accatggctt    2820
taagtaccat gttgttaagg attctcatga agtgccatag actgtacatc aaattagagt    2880
attatttctt cagtgttatt gtttctggag ccacattttg ttgcttattt gctagtacta    2940
atcaatcaaa gggcaccatt cttttctttt ttgtttttga aaccaaagct gtctcagaaa    3000
tggccaattt aactttacag taacaataga cagcacaaca caaactcaat acagataacc    3060
tttcacatac tggagatata tatgatagat atataaaatt attttaatgc attgtagtgt    3120
aatatttatg catactctac tatataacat gttattcaaa agggatatgc catttctgag    3180
acacaataac aaaaaatgtt tgaggaaatt attttgcttc tatttatagc ctctgtcaaa    3240
agtcaaaaga ctaaaatgc tttgcagaaa tgggttcacg tttgcttaaa cgcttcatca    3300
cagtcacatt caaaatagtg actctaaaca aagagaacag cactgtcatc agatgcatga    3360
taaaccaaaa tatgaaaatg ggaaatgttt aattaaccta gtaattgggt gggttaagta    3420
catgggtgaa ttttatatgt gattcttttg ttcagattaa ctgcttatag ccttagaaag    3480
ccttttaaaa aatttaaaa atagatgtgc attcagttttt taagaatgga ttcatccaaa    3540
ggaattcccc ttttttgtgg tttggatgtt gcagctagga aaggctatttt ttgctctgtt    3600 cagcagttct aaaatcgctg agtagggggcc aggtcactgg cagttctagt gtggaatggg    3660
agaagtgaga gttctgttat agaactttcc atacttccaa gtttactgca agtttttatg    3720
cttgagagag atgctttcta atataagact gatgtgttga ttttcctgat tgtactgtac    3780
atctattaaa gccttagatt attacattac gggttggaac ccataccaat gtaatttcaa    3840
tcgtgttaag agagtaatgg tgacttcaca tgttattgta gttagttacg ttatagaata    3900
ttacttattt ttcttgttaa aatgtagttt ttcatttcct acatttattg gattttcatt    3960
ttctattaac agttgaatac catttcagtt tttagactat tgttttatta gattttacca    4020
atgaattttt caaaatacaa aaaaattaaa gtagtttttt cttcataaca tactcagttt    4080
taaattacat gtagtgtcat atgaatatcc gtattattgt taactaaatg atttatattt    4140
tactgattta atattacagt gtaagaatgt cagtcattgt tcttgtctag ttttcattaa    4200
aagaacaaag atctttttata tggatatctt ataaatatat aatcattgct aagtaagaag    4260
ttaagttgtt gctatggcaa caatcctggc agacaattga gtaatatttt gatgatttat    4320
tttgtttgta attagttatt atgagaagat ctagatccta gatattagaa taaaatttat    4380
tttctactgt atccatttca aatgttaaag tattgtttaa tattttttgaa atccctgaat    4440 atcaggcctt gttataaata agctgcataa tcaataaata gaacaaggga cttttttgttg    4500 ataatccaaa tactcaaagt ttacgtaatg agaattttag cgtgtgtgca aactcttgag    4560
ggttgatgat gctgcaattt agcatgttgg aaagtctaga gagaaggttg acttttttgca    4620 cttctgtata tagtcaaaag agagaaacct gtataatagc aagatcttat tttgaataaa    4680
aacgtctata attacaagga gttttgttaa ggctaatgaa atgacagact gagcaaaatt    4740
```

-continued

```
gcttgcaaaa gtggcacaga gttagcactc catacccttc aaacacgtcg ctttgctttt      4800
tgtggacagc ttgtagtttg ccaggatttt tcagctggaa agatttgcca tccttccaag      4860
atctcatgac tgacaaaact ccattgggcc aaatctgcct gaagatcatt accaaaaaat      4920
agcaggtact tcagccacta agatgaaatc atggatcaga tatcccttac attgttttca      4980
aaactactgc atgtttaaaa cttcaacaaa aagagagaaa gaactatgct aaggacatat      5040
attattcaga tcgatatcta ccaatttcag tggtttaatg ttcacaaaat gaaatcttga      5100
aaataactat tgactttcac aaaatttta  ccataaacag gcaaaccaaa cagcacacct      5160
gtagttgttc tgtgattgtt ttttaattgc tgtagatcat gttctttccg caggtggaaa      5220
aaaaaaaaaa aaaaaaaaa  gaagttcaaa tttcacagtt ttaattttca actcagaagc      5280 aaagagcaa  aatgtgacaa tggccacttg tttaatgact tggttgccca gctgtcactg      5340
cagctggcta ctgatgttgc acttaccagc aacccaccca ccttcatctg ccgaaaggac      5400
agtgagcttg gttttacgat tatgtaatca caacttactt tctgcttgta gtggcttaaa      5460
attatgtatt ttgtctaggg ctgcaatttg ttttatgctt actttattat tactgcagta      5520
gttgactttg ctgtatggaa aaataaagcg aaattgccct aataaaactt ctctttctta      5580
agtaaaaa                                                               5588

<210> SEQ ID NO 2
<211> LENGTH: 4527
<212> TYPE: DNA
<213> ORGANISM: Mus musculus

<400> SEQUENCE: 2
agcagtggta acaacgcaga gtacgggggg tgggaaggaa gggctgcagc tcacagcaac        60
agagtttaga ctgtctttgc ttcatcatct gaaggtaaaa ttttccagcc acggccggcg       120
gctcgcagag tacaataaac agggacggag aactatttgc atggaccccc cttcctcatg       180
atgcggtgga gaagccacgg ccactcggtc ctgccagatg ttcttggggt tactgtacat       240
ggggaagacg agcagagcta acaagaatt  taaagaggac gaaggaagga aagcgccatc       300
ctgctcaaat acaaagatct aagagggttg ttttcccaca tcctccaaag ctgtgagcat       360
tagaactaat attttcccaa agagtgccat cgtattaaag ccactttatt aaggaggggt       420
gtatctgcaa aacagtcaag agactagaac cctgggagcc agagatgaca gtgagcacgc       480
actgcttgtg gctcacagtc ttccagtggg gcctatcgat cggtgactga cttcctgctt       540
gctgacacat tccccctccc cggtttcctg gattggactg cattaaagaa ttcactgctt       600
accttcaaac ttacatgttg gagttttcac ggcggttgtt ttgagatcat tgagactcgg       660
attgatttcg acatttaacc gaaaggaaca gagcccaaag tagttctcat catggccttg       720
aacgttgccc ccgtgagaga cacaaagtgg ctgacgctgg aggtctgcag acagtaccag       780
agaggaacgt gctcacgctc cgacgaagaa tgcaagtttg ctcacccccc caaaagttgc       840
caggttgaaa atggaagagt aattgcctgc tttgattccc tcaagggccg ctgttcaaga       900
gagaactgca atatcttca  tcctccgaca cacttaaaaa cccagctaga gattaatggg       960
aggaacaatt tgatccagca aaaaactgca gcagcgatgc ttgcccagca gatgcaattt      1020
atgtttccag gaacgccgct ccatcctgtg cccacttttc ctgtaggtcc caccataggg      1080
acaaatgcgg ctattagctt tgctccttac ttagcgcctg tcacccctgg agttgggtta      1140
gtcccaacag aggttctacc cactacaccg gtcattgttc ccggaagtcc accggtcact      1200
gtcccgggct caactgcaac tcagaaactt ctcaggactg ataaactgga ggtatgcagg      1260
```

```
gagttccagc gaggaaactg tgcccgggga gagacagact gccgctttgc acacccggca    1320
gacagcacca tgatcgacac aaacgacaac accgtaaccg tttgtatgga ttacataaag    1380
gggcgttgca tgagggagaa atgcaaatat tttcaccctc ctgcacactt gcaggccaaa    1440
atcaaagctg cgcagcacca agccaaccag gccgcggtgg ccgcccaggc agccgcggcc    1500
gcggccacag tcatggcctt ccctccgggt gctcttcatc ccttaccaaa gagacaagca    1560
cttgaaaaaa gcaacggggc cagcacggtc ttcaaccccca gcgtcttgca ctaccagcag    1620
```

```
gagttccagc gaggaaactg tgcccgggga gagacagact gccgctttgc acacccggca    1320
gacagcacca tgatcgacac aaacgacaac accgtaaccg tttgtatgga ttacataaag    1380
gggcgttgca tgagggagaa atgcaaatat tttcaccctc ctgcacactt gcaggccaaa    1440
atcaaagctg cgcagcacca agccaaccag gccgcggtgg ccgcccaggc agccgcggcc    1500
gcggccacag tcatggcctt ccctccgggt gctcttcatc ccttaccaaa gagacaagca    1560
cttgaaaaaa gcaacggggc cagcacggtc ttcaaccccca gcgtcttgca ctaccagcag    1620
gctctgacca gtgcgcagct gcagcagcac acggcgttca tccccacagt acccatgatg    1680
cacagcgcta cgtccgccac tgtctctgca gcaacaactc ctgcaacaag tgtccccttc    1740
gcagcaacag ccacagccaa tcagataatt ctgaaataat caacagaaat ggaatggaat    1800
gccaagaatc tgcattgaga ataactaaac attgttactg tacatattac cccgtttcct    1860
cctcaataga attgccacaa actgcatgct aaatttagtt cttctggaca gaccacaacc    1920
ctaaggctag ttctgctatg tcatatatga gtattaaata tggtatgctt agtatactcc    1980
agcctaagat agttaaccac ctgagaccag ctgtgatgtt cgaagacata caggatgagg    2040 tttttctttca cagggttctg agcatagttt ctgtcccagg aatattgtct tatctccata    2100
actatagctg atgcagaaag tccagacaat atactcattt cgactcagaa tatttcaaat    2160
ttagcaataa acagttagct ttagttttaa gtaccctattc caagggcagg ttcgattgta    2220
actccaatca caaccatttc atttcctgac tggatcgaag ggtatgattc acttcttgag    2280
gagacggaca gtcgcagcag agagaagtga agtaaaacat acgcctgcct cgcaggtcta    2340
aagtctgagt ggcagctcaa gcacaattgc caggggacac atcagagtgt ggggttcgct    2400
ttgccaggag atgccgcact gaatcatggg attctagaat aacattgcat agattgaaaa    2460
aaaaaaaaaa actttgcacg gtatgagctt catacccaac ccaacaaagt cttgaaggta    2520
ttattttaca agtatatttt taaagttgtt ttataagaga gactttgtag aagtgcctag    2580
attttgccag acttcatcca gcttgacaag aatgaaaggc tcatgccaat agtcgaatct    2640
aagggattgg tctttcaaac tcgccctccg gttgcctgtt accgaataac tcttctaaac    2700
taaaacctag tcaaacaggg aagctgtagg tgaggaggtc tgtataatat ccagtttaa    2760 gtacgtctga gtttagtcac tacagatgca aactgtgact ttaatctaaa ttactatgta    2820
aacgaaaaaa aaaagtagat agtttcactt tttaaaaact ccattactgt ttttgcattt    2880
taagagttgg attaaagggt tgtaagtaac tgcagcatgg aaaaatagtt cttttaattc    2940
tttcacctta aagcatattt tatgtctcaa aagtataaaa aactttaata caagtacaca    3000
catattatat atacacatac atatatatac tatatatgga tgaaacatat tttaatgttg    3060 tttactttt ttaaatactt ggttgatctt caaggtaata gcgatacaat taaattttgt    3120
tcagaaagtt tgttttaaag tttattttaa gcactatcgt accaaatatt tcatatttca    3180
cattttatat gttgcacata gcctacacag tacctacata gttttttaaat tattgtttaa    3240 gaaatgaaac agctgttata aatggatatt atgtgtaatt gtttaaaaca tccattttct    3300
ttgtgaacat tttagtgatt gaagtatttt gacttttgag attgaatgta aaatatttta    3360
aattttggta tcatcgcctg ttctgaaaac tagaggcatc caaccatatc attttttttg    3420
attgaaaaaa gatctgcatt taattcatgt tggtcaaagt ctaattacta tttatcttac    3480
atcatagatc tgataactgt atcgaaaaga gaaatcacat tctgagtgta atcttgcata    3540
gtgcttgtgt cgtgtttgtt tttaatttgt ggaaaggtat tgtatctaac ttgtatcacc    3600
ttgatagttc tcatctttat gtattattga tatttgtaat ttcctcagct ataacaatgt    3660
```

-continued

| | |
|---|---|
| agttacgcta caacttgcct aaaacactca tactttttt tttctttact tactcattta | 3720 |
| aactcattga gaagatagta gactaaaaag gtaaattatg ggaatcactg aaatatttt | 3780 |
| gtagactaat tgttgtaact gtcctttctt cctttcattt catgattttt attttaaaaa | 3840 |
| ttattagcac atagctattt tcagcccttt aataactgat catcaaaaca tcacctgtat | 3900 |
| cccccagcca atatagatga ctgtattttt tactatgata tccattttcc agaattgtga | 3960 |
| ttataatatg cagagtcaaa tatgccattt acaataagga ggaggccagg caaatgcata | 4020 |
| gatgtacaaa tatatgtaca acagatttg cttttattt atttataatg taatttata | 4080 |
| gaataattct gggatttgag aggatctaaa actattttc tgtataaata ttatttgcca | 4140 |
| aaagtttgtt tatattcaga agtctgacta tgatggataa atcttaaatg ctttgtttaa | 4200 |
| ttacaaaaac aaaatcacca atatccaaga caggaagatc tcagttcaac agctccggta | 4260 |
| gttagggaac taactccact tgcacaggac ttcatttcac tcttggtttt caggctataa | 4320 |
| cagcacttca cagaactatt ctttcagcca tacaccactg gtcacatttc tactaaatct | 4380 |
| ttctgtaaca cttcttaaag aattccctca ttcgttatct tacagtgtaa acaggactct | 4440 |
| aatttgtatc aattatatgt tttggttgta atattcagtt cactcaccca atgtacaacc | 4500 |
| aatgaaataa aagaagcatt taaaagg | 4527 |

<210> SEQ ID NO 3
<211> LENGTH: 1967
<212> TYPE: DNA
<213> ORGANISM: Mus musculus

<400> SEQUENCE: 3

| | |
|---|---|
| ctgaaggatc acgtaactca gaaaatctaa aacacattat gtgtccaaat cagttcttct | 60 |
| gagttacgcg gacgcgtggg tttcacgacg caagtgcgtc ctacaggaag aaagtgcccc | 120 |
| cagtcggagc gcgagcagga gcgcgacttt ttggcgctct ttgcgagcga gccgcaagga | 180 |
| ggcggaagac ggtcccgggc cggggcgcgg gaatcggggc agcgagcgcc gcacggggga | 240 |
| gttcctgcgc gtggcgtcct cgcagcgaga cgccgctgga gtcgctcact cggagagatt | 300 |
| ccttgaacca tctgcagtca taatattctc tgaagagggt gcacttgatt gccaatttgc | 360 |
| tctcagtatg acacctgtca atgtagctct aatccgtgat accaagtggc tgactttaga | 420 |
| agtctgtaga gaatttcaga gaggaacttg ctctcgagct gatgcagagt gcaggtttgc | 480 |
| ccatccgcca agagtttgcc atgtggaaaa tggccgagtg gtggcctgtt ttgattcact | 540 |
| aaagggtcgg tgcactcgtg agaactgcaa gtacctccac cctccaccgc acttaaagtc | 600 |
| gcagctagaa gttaatggga gaaacaatct gattcaacag aagactgccg cagccatgtt | 660 |
| cgcccagcac atgcaactca tgctgcagaa cgctcagatg tcatctcttg cgtcttttcc | 720 |
| tatgaatcca tcacttgcag ctaatcctgc catggctttc aatccttaca tgactcatcc | 780 |
| tggcatgggc ctggttcctg ctgagctttt accaaatggt ccggttctga tttctggaaa | 840 |
| ccctcctctt gcactgccag gagttcctgg tccaaagcca attcgtacag atagactgga | 900 |
| ggtttgccgt gaatttcagc gtggaaattg taccgtggg gagagcgagt gccgctatgc | 960 |
| tcaccctacg gatgtttcca tgattgaagt cactgataat tctgtgacaa tctgcatgga | 1020 |
| ttacattaaa ggccgatgct cccgggagaa atgcaagtac tttcatcctc ctcccccactt | 1080 |
| gcaggccaaa ctcagggcag ctcatcacca gatgaaccat tctgctgcca atgcaatggc | 1140 |
| cctgccgcat ggtgcacttc aactgatacc aaagaggtca gccttgaca aggccaatgg | 1200 |
| tgccactcca gtctttaacc ccagtgtttt ccactgccaa caggctctgg ctaacatgca | 1260 |

```
gattcctcag caggctttta tcccaacagt gcccatgatg cacggtgcta caccttccac    1320
tgtgtctaca gcaacaccac ctgccagcaa cgttccctac gttccaacaa ctacaggcaa    1380
ccagttgaaa tattgagcag cagagttaca gagtatcaga atctctcaac aagaaactcc    1440
gtgtggcctt tctatatgta ttctcgtatg tcttcttgta ccaacacgac aataagcatg    1500
gtgcagtcaa tatactaaag cgcatatacc tgttgacaaa ttcaaatttt aaaaatctgt    1560
ggagatgtta aagcaaatag aaaattaacc agtatgtgtt accttatacg gattcattgt    1620
atatgaatta gcatacaata tacaaccata caggtttgtc atgtatatga attatcagat    1680
ccatattaca tgaattttcc atatgatatg aattaccata ttgaatataa ctgtaaaatg    1740
ttgtgactgc tttccagtaa tggtttataa taaatgaact tccacagtgt actgtaggct    1800
tactgtatac tcttggtgga taaattctgt tttggaagtg ttaccttact gttttgttta    1860
caagatagtc tataggattg atgtagaatg taactgatat ttcccacacc attttcctcc    1920
attggtatat tgtattaaat tgggttctgc ttaaaaaaaa aaaaaaa                  1967

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
tgggatggaa ttgtggtgtg ttgttgctca tg                                   32

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
tccatttgtc acgtcctgca ccgacgc                                         27

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
ctacgatggc tggctgcaat atgcctcact gtaag                                35

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gggttgaatc tcgttaggga cactgggtgt ctgtaa                               36

<210> SEQ ID NO 8
<211> LENGTH: 35
<212> TYPE: DNA
```

<213> ORGANISM: Artificial Sequence
<220> FEATURE:
<223> OTHER INFORMATION: Description of Artificial Sequence: Synthetic Primer

<400> SEQUENCE: 8
ctacgatggc tggctgcaat atgcctcact gtaag                35

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic Primer

<400> SEQUENCE: 9
gggttgaatc tcgttaggga cactgggtgt ctgtaa               36

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 10
tggcagaccc tttgacaccg                                 20

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic Primer

<400> SEQUENCE: 11
tagtgtcaca ccaattcggg acacaaa                         27

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic Primer

<400> SEQUENCE: 12
cccttgatgt aatccatgca gacagtga                        28

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 13
tgcacggtgc tacgccagcc                                 20

<210> SEQ ID NO 14
<211> LENGTH: 28
<212> TYPE: DNA
<213> ORGANISM: Artificial Sequence
<220> FEATURE:

```
<223> OTHER INFORMATION: Description of Artificial Sequence: Synthetic
      Primer

<400> SEQUENCE: 14
gtgacgacag ctctacatct gggtaaca                                              28

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
cctgctgcac actgttgcct acac                                                  24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
tgtcagttcc ctccctcacc atgt                                                  24

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
ggaatacctc acactcaagg cc                                                    22

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
cacggaacac aaaggcactg aatgt                                                 25

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
gccgaggagg tggtggagga gta                                                   23

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer
```

```
<400> SEQUENCE: 20
gtctcagcct caccctcagg ctca                                              24

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
tctgacgagg aaactgaaca ag                                                22

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
tgtcaatgag ggcttggag                                                    19

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
ttcaccatgt ctgacgagga ag                                                22

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
cttctgggat cttaggagca gtg                                               23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
ccttgtacca actggagact gac                                               23

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
```

```
tgatggtctc tgctgcagtg                                            20
```

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27

```
gacctggaag ctggcaagaa c                                          21
```

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28

```
tcccttcgtc attgatgtag gc                                         22
```

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29

```
ccatgaatga caccaacacc ac                                         22
```

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30

```
ctgagggtga cgatgaagct g                                          21
```

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31

```
tcttcacggg catcttcact g                                          21
```

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32

```
cgccgctgtt caatgtagat g                                          21
```

```
<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
tgcctctatg tggacatctc cc                                              22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
cgactctttc ttgacgtagg cg                                              22

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      SiRNA construct

<400> SEQUENCE: 35
aacagacaga cuugagguau g                                               21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      SiRNA construct

<400> SEQUENCE: 36
aacacggaau guaaauuugc a                                               21

<210> SEQ ID NO 37
<211> LENGTH: 3641
<212> TYPE: DNA
<213> ORGANISM: Homo sapiens

<400> SEQUENCE: 37
gctgactcgc ctggctctga gccccgccgc cgcgctcggg ctccgtcagt ttcctcggca     60
gcggtaggcg agagcacgcg gaggagcgtg cgcgggggcc ccgggagacg gcggcgtgg    120 cggcgcgggc agagcaagga cgcggcggat cccactcgca cagcagcgca ctcggtgccc    180
cgcgcagggt cgcgatgctg cccggttttgg cactgctcct gctggccgcc tggacggctc    240
gggcgctgga ggtacccact gatggtaatg ctggcctgct ggctgaaccc cagattgcca    300
tgttctgtgg cagactgaac atgcacatga atgtccagaa tgggaagtgg gattcagatc    360
catcagggac caaaacctgc attgatacca aggaaggcat cctgcagtat tgccaagaag    420
tctaccctga actgcagatc accaatgtgg tagaagccaa ccaaccagtg accatccaga    480
actggtgcaa gcggggccgc aagcagtgca agacccatcc ccactttgtg attccctacc    540
gctgcttagt tggtgagttt gtaagtgatg cccttctcgt tcctgacaag tgcaaattct    600
```

```
tacaccagga gaggatggat gtttgcgaaa ctcatcttca ctggcacacc gtcgccaaag      660
agacatgcag tgagaagagt accaacttgc atgactacgg catgttgctg ccctgcggaa      720
ttgacaagtt ccgaggggta gagtttgtgt gttgcccact ggctgaagaa agtgacaatg      780
tggattctgc tgatgcggag gaggatgact cggatgtctg gtgggcggga gcagacacag      840
actatgcaga tgggagtgaa gacaaagtag tagaagtagc agaggaggaa gaagtggctg      900
aggtggaaga agaagaagcc gatgatgacg aggacgatga ggatggtgat gaggtagagg      960
aagaggctga ggaaccctac gaagaagcca cagagagaac caccagcatt gccaccacca     1020
ccaccaccac cacagagtct gtggaagagg tggttcgaga ggtgtgctct gaacaagccg     1080
agacggggcc gtgccgagca atgatctccc gctggtactt tgatgtgact gaagggaagt     1140
gtgccccatt cttttacggc ggatgtgcg gcaaccggaa caactttgac acagaagagt      1200
actgcatggc cgtgtgtggc agcgccatgt cccaaagttt actcaagact acccaggaac     1260
ctcttgcccg agatcctgtt aaacttccta caacagcagc cagtacccct gatgccgttg     1320
acaagtatct cgagacacct ggggatgaga atgaacatgc ccatttccag aaagccaaag     1380
agaggcttga ggccaagcac cgagagagaa tgtcccaggt catgagagaa tgggaagagg     1440
cagaacgtca agcaaagaac ttgcctaaag ctgataagaa ggcagttatc cagcatttcc     1500
aggagaaagt ggaatctttg gaacaggaag cagccaacga gagacagcag ctggtggaga     1560
cacacatggc cagagtggaa gccatgctca atgaccgccg ccgcctggcc ctggagaact     1620
acatcaccgc tctgcaggct gttcctcctc ggcctcgtca cgtgttcaat atgctaaaga     1680
agtatgtccg cgcagaacag aaggacagac agcacaccct aaagcatttc gagcatgtgc     1740
gcatggtgga tccaagaaaa gccgctcaga tccggtccca ggttatgaca cacctccgtg     1800
tgatttatga gcgcatgaat cagtctctct ccctgctcta caacgtgcct gcagtggccg     1860
aggagattca ggatgaagtt gatgagctgc ttcagaaaga gcaaaactat tcagatgacg     1920
tcttggccaa catgattagt gaaccaagga tcagttacgg aaacgatgct ctcatgccat     1980
ctttgaccga aacgaaaacc accgtggagc tccttcccgt gaatggagag ttcagcctgg     2040
acgatctcca gccgtggcat tcttttgggg ctgactctgt gccagccaac acagaaaacg     2100
aagttgagcc tgttgatgcc cgccctgctg ccgaccgagg actgaccact cgaccaggtt     2160
ctgggttgac aaatatcaag acggaggaga tctctgaagt gaagatggat gcagaattcc     2220
gacatgactc aggatatgaa gttcatcatc aaaaattggt gttctttgca gaagatgtgg     2280
gttcaaacaa aggtgcaatc attggactca tggtgggcgg tgttgtcata gcgacagtga     2340
tcgtcatcac cttggtgatg ctgaagaaga acagtacac atccattcat catggtgtgg      2400
tggaggttga cgccgctgtc accccagagg agcgccacct gtccaagatg cagcagaacg     2460
gctacgaaaa tccaacctac aagttctttg agcagatgca gaactagacc cccgccacag     2520
cagcctctga agttggacag caaaaccatt gcttcactac ccatcggtgt ccatttatag     2580
aataatgtgg gaagaaacaa acccgtttta tgatttactc attatcgcct tttgacagct     2640
gtgctgtaac acaagtagat gcctgaactt gaattaatcc acacatcagt aatgtattct     2700
atctctcttt acattttggt ctctatacta cattattaat gggttttgtg tactgtaaag     2760
aatttagctg tatcaaacta gtgcatgaat agattctctc ctgattattt atcacatagc     2820
cccttagcca gttgtatatt attcttgtgg tttgtgaccc aattaagtcc tactttacat     2880
atgctttaag aatcgatggg ggatgcttca tgtgaacgtg ggagttcagc tgcttctctt     2940
gcctaagtat tcctttcctg atcactatgc attttaaagt taaacatttt taagtatttc     3000
```

| | |
|---|---|
| agatgcttta gagagatttt ttttccatga ctgcatttta ctgtacagat tgctgcttct | 3060 |
| gctatatttg tgatataggg attaagagga tacacacgtt tgtttcttcg tgcctgtttt | 3120 |
| atgtgcacac attaggcatt gagacttcaa gcttttcttt ttttgtccac gtatctttgg | 3180 |
| gtctttgata agaaaagaa tccctgttca ttgtaagcac ttttacgggg cgggtgggga | 3240 |
| ggggtgctct gctggtcttc aattaccaag aattctccaa acaattttc tgcaggatga | 3300 |
| ttgtacagaa tcattgctta tgacatgatc gctttctaca ctgtattaca taaataaatt | 3360 |
| aaataaaata accccgggca agacttttct ttgaaggatg actacagaca ttaaataatc | 3420 |
| gaagtaattt tgggtgggga gaagaggcag attcaatttt ctttaaccag tctgaagttt | 3480 |
| catttatgat acaaaagaag atgaaaatgg aagtggcaat ataagggat gaggaaggca | 3540 |
| tgcctggaca aaccctctt ttaagatgtg tcttcaattt gtataaaatg gtgttttcat | 3600 |
| gtaaataaat acattcttgg aggagcaaaa aaaaaaaaaa a | 3641 |

<210> SEQ ID NO 38
<211> LENGTH: 3150
<212> TYPE: DNA
<213> ORGANISM: Homo sapiens

<400> SEQUENCE: 38

| | |
|---|---|
| aagcttatcg atccgtcgac ctcgaggggg ggcccgcgtt cgccgcgcag agccaggccc | 60 |
| gccgggcgag cccatgagca ccatgcgcct gctgacgctc gccctgctgt ctcctgctc | 120 |
| cgtcgcccgt gccgcgtgcg accccaagat cgtcaacatt ggcgcggtgc tgagcacgcg | 180 |
| gaagcacgag cagatgttcc gcgaggccgt gaaccaggcc aacaagcggc acggctcctg | 240 |
| gaagattcag ctcaatgcca cctccgtcac gcacaagccc aacgccatcc agatggctct | 300 |
| gtcggtgtgc gaggacctca tctccagcca ggtctacgcc atcctagtta gccatccacc | 360 |
| taccccaac gaccacttca ctcccacccc tgtctcctac acagccggct tctaccgcat | 420 |
| acccgtgctg ggctgacca cccgcatgtc catctactcg gacaagagca tccacctgag | 480 |
| cttcctgcgc accgtgccgc cctactccca ccagtccagc gtgtggtttg agatgatgcg | 540 |
| tgtgtacagc tggaaccaca tcatcctgct ggtcagcgac gaccacgagg gccgggccgc | 600 |
| tcagaaacgc ctggagacgc tgctggagga gcgtgagtcc aagagtaaaa aaaggaacta | 660 |
| tgaaaacctc gaccaactgt cctatgacaa caagcgcgga cccaaggcag agaaggtgct | 720 |
| gcagtttgac ccagggacca agaacgtgac ggccctgctg atggaggcga aagagctgga | 780 |
| ggcccgggtc atcatccttt ctgccagcga ggacgatgct gccactgtat accgagcagc | 840 |
| cgcgatgctg aacatgacgg gctccgggta cgtgtggctg gtcggcgagc gcagatctc | 900 |
| gggaacgcc ctgcgttacg ccccggacgg catcctcggg ctgcagctca tcaacggcaa | 960 |
| gaacgagtcg gcccacatca gcgacgccgt aggcgtggtg gcccaggccg tgcacgagct | 1020 |
| cctcgagaag gagaacatca ccgacccgcc gcgggggctgc gtgggcaaca ccaacatctg | 1080 |
| gaagaccggg ccgctcttca agagagtgct gatgtcttcc aagtatgcgg atggggtgac | 1140 |
| tggtcgcgtg gagttcaatg aggatgggga ccggaagttc gccaactaca gcatcatgaa | 1200 |
| cctgcagaac cgcaagctgg tgcaagtggg catctacaat ggcacccacg tcatccctaa | 1260 |
| tgacaggaag atcatctggc caggcggaga cacagagaag cctcgagggt accagatgtc | 1320 |
| caccagactg aagattgtga cgatccacca ggagcccttc gtgtacgtca gcccacgct | 1380 |
| gagtgatggg acatgcaagg aggagttcac agtcaacggc gacccagtca agaaggtgat | 1440 |
| ctgcaccggg cccaacgaca cgtcgccggg cagcccccgc cacacggtgc ctcagtgttg | 1500 |

```
ctacggcttt tgcatcgacc tgctcatcaa gctggcacgg accatgaact tcacctacga   1560
ggtgcacctg gtggcagatg gcaagttcgg cacacaggag cgggtgaaca acagcaacaa   1620
gaaggagtgg aatgggatga tgggcgagct gctcagcggg caggcagaca tgatcgtggc   1680
gccgctaacc ataaacaacg agcgcgcgca gtacatcgag ttttccaagc ccttcaagta   1740
ccagggcctg actatgctgg tcaagaagga gattccccgg agcacgctgg actcgttcat   1800
gcagccgttc cagagcacac tgtggctgct ggtgggctg tcggtgcacg tggtggccgt    1860
gatgctgtac ctgctggacc gcttcagccc cttcggccgg ttcaaggtga acagcgagga   1920
ggaggaggag gacgcactga ccctgtcctc ggccatgtgg ttctcctggg gcgtcctgct   1980
caactccggc atcggggaag cgcccccag aagcttctca gcgcgcatcc tgggcatggt    2040
gtgggccggc tttgccatga tcatcgtggc ctcctacacc gccaacctgg ccgcttttcct  2100
ggtgctggac cggccggagg agcgcatcac gggcatcaac gaccctcggc tgaggaaccc   2160
ttctgacaag tttatctact ccacggtgaa gcagagctcc gtggatatct acttccggcg   2220
ccaggtggag ctgagcacca tgtaccggca tatggagaag cacaactacg agagtgcggc   2280
ggaagccatc caggccgtga gagacaacaa gctgcatgcc ttcatctggg actcggcggt   2340
gctggagttc gaggcctcgc agaagtgcga cctggtgacg actggagagc tgttttttccg  2400
ctcgggcttc ggcataggca tgcgcaaaga cagcccctgg aagcagaacg tctccctgtc   2460
catcctcaag tcccacgaga atggcttcat ggaagacctg gacaagacgt gggttcggta   2520
tcaggaatgt gactcgcgca gcaacgcccc tgcgaccctt acttttgaga acatggccgg   2580
ggtcttcatg ctggtagctg ggggcatcgt ggccgggatc ttcctgattt tcatcgagat   2640
tgcctacaag cggcacaagg atgctcgccg gaagcagatg cagctggcct ttgccgccgt   2700
taacgtgtgg cggaagaacc tgcagcagta ccatcccact gatatcacgg gcccgctcaa   2760
cctctcagat ccctcggtca gcaccgtggt gtgaggcccc cggaggcgcc cacctgccca   2820
gttagcccgg ccaaggacac tgatgggtcc tgctgctcgg gaaggcctga gggaagccca   2880
cccgccccag agactgccca ccctgggcct ccgtccgtc cgcccgccca ccccgctgcc     2940
tggcgccacc ctgctggacc aaggtgcgga ccggagcggc tgaggacggg gcagagctga   3000
gtcggctggg cagggcgcag gcgcgtgcac ggcagaggca gggcctgggg tctctgagca   3060
gtggggagcg ggggctaact ggcccaggcg gagggccttg gagcagagac ggcagcccca   3120
tccttcccgg cagcaccagc gtgagggcca                                    3150
```

<210> SEQ ID NO 39
<211> LENGTH: 2796
<212> TYPE: DNA
<213> ORGANISM: Homo sapiens

<400> SEQUENCE: 39

```
cctcccctgg ggaggctcgc gttcccgctg ctcgcgcctg ccgcccgccg gcctcaggaa     60
cgcgccctct cgccgcgcgc gccctcgcag tcaccgccac ccaccagctc cggcaccaac   120
agcagcgccg ctgccaccgc ccaccttctg ccgccgccac cacagccacc ttctcctcct   180
ccgctgtcct ctcccgtcct cgcctctgtc gactatcagg tgaactttga accaggatgg   240
ctgagccccg ccaggagttc gaagtgatgg aagatcacgc tgggacgtac gggttggggg   300
acaggaaaga tcaggggggc tacaccatgc accaagacca agagggtgac acggacgctg   360
gcctgaaaga atctccctg cagaccccca ctgaggacga atctgaggaa ccgggctctg    420
aaacctctga tgctaagagc actccaacag cggaagatgt gacagcaccc ttagtggatg   480
```

```
agggagctcc cggcaagcag gctgccgcgc agccccacac ggagatccca gaaggaacca      540
cagctgaaga agcaggcatt ggagacaccc ccagcctgga gacgaagct gctggtcacg       600 tgacccaagc tcgcatggtc agtaaaagca aagacgggac tggaagcgat gacaaaaaag     660 ccaaggggc tgatggtaaa acgaagatcg ccacaccgcg gggagcagcc cctccaggcc      720
agaagggcca ggccaacgcc accaggattc agcaaaaac cccgcccgct ccaaagacac     780
cacccagctc tggtgaacct ccaaaatcag gggatcgcag cggctacagc agccccggct     840
ccccaggcac tcccggcagc cgctcccgca ccccgtccct tccaacccca cccacccggg    900
agcccaagaa ggtggcagtg gtccgtactc cacccaagtc gccgtcttcc gccaagagcc   960
gcctgcagac agccccgtg cccatgccag acctgaagaa tgtcaagtcc aagatcggct    1020
ccactgagaa cctgaagcac cagccgggag gcggaaggt gcagataatt aataagaagc   1080
tggatcttag caacgtccag tccaagtgtg gctcaaagga taatatcaaa cacgtcccgg  1140
gaggcggcag tgtgcaaata gtctacaaac cagttgacct gagcaaggtg acctccaagt  1200
gtggctcatt aggcaacatc catcataaac caggaggtgg ccaggtggaa gtaaaatctg   1260
agaagcttga cttcaaggac agagtccagt cgaagattgg gtccctggac aatatcaccc   1320
acgtccctgg cggaggaaat aaaaagattg aaacccacaa gctgaccttc cgcgagaacg  1380
ccaaagccaa gacagaccac ggggcggaga tcgtgtacaa gtcgccagtg gtgtctgggg 1440
acacgtctcc acggcatctc agcaatgtct cctccaccgg cagcatcgac atggtagact   1500
cgccccagct cgccacgcta gctgacgagg tgtctgcctc cctggccaag cagggtttgt   1560
gatcaggccc ctggggcggt caataattgt ggagaggaga gaatgagaga gtgtggaaaa   1620
aaaaagaata atgaccccggc ccccgccctc tgccccagc tgctcctcgc agttcggtta   1680
attggttaat cacttaacct gcttttgtca ctcggctttg gctcgggact tcaaaatcag    1740
tgatgggagt aagagcaaat ttcatctttc caaattgatg ggtgggctag taataaaata   1800
tttaaaaaaa aacattcaaa aacatggcca catccaacat ttcctcaggc aattcctttt    1860
gattcttttt tcttccccct ccatgtagaa gagggagaag gagaggctct gaaagctgct   1920
tctgggggat ttcaagggac tgggggtgcc aaccacctct ggccctgttg tgggggttgt    1980
cacagaggca gtggcagcaa caaaggattt gaaaactttg gtgtgttcgt ggagccacag  2040
gcagacgatg tcaaccttgt gtgagtgtga cggggggttgg ggtggggcgg gaggccacgg  2100
gggaggccga ggcaggggct gggcagaggg gaggaggaag cacaagaagt gggagtggga   2160
gaggaagcca cgtgctggag agtagacatc cccctccttg ccgctgggag agccaaggcc   2220
tatgccacct gcagcgtctg agcggccgcc tgtccttggt ggccggggt ggggcctgc    2280 tgtgggtcag tgtgccaccc tctgcagggc agcctgtggg agaagggaca gcgggttaaa   2340
aagagaaggc aagcctggca ggagggttgg cacttcgatg atgacctcct tagaaagact  2400
gaccttgatg tcttgagagc gctggcctct tcctccctcc ctgcagggta gggcgcctga    2460
gcctaggcgg ttccctctgc tccacagaaa ccctgtttta ttgagttctg aaggttggaa   2520
ctgctgccat gattttggcc actttgcaga cctgggactt tagggctaac cagttctctt    2580
tgtaaggact tgtgcctctt gggagacgtc cacccgtttc caagcctggg ccactggcat   2640
ctctggagtg tgtgggggtc tgggaggcag gtcccgagcc ccctgtcctt cccacggcca  2700
ctgcagtcac cccgtctgcg ccgctgtgct gttgtctgcc gtgagagccc aatcactgcc   2760
tatacccctc atcacacgtc acaatgtccc gaattc                              2796
```

-continued

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
tgaaggaata cctcacactc aaggcc                                          26

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
cacggaacac aaaggcactg aatgt                                           25

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      Cys3His zinc-finger motif
<220> FEATURE:
<221> NAME/KEY: MOD_RES
<222> LOCATION: (2)..(8)
<223> OTHER INFORMATION: Variable residue
<220> FEATURE:
<221> NAME/KEY: MOD_RES
<222> LOCATION: (10)..(15)
<223> OTHER INFORMATION: Variable residue
<220> FEATURE:
<221> NAME/KEY: MOD_RES
<222> LOCATION: (17)..(19)
<223> OTHER INFORMATION: Variable residue

<400> SEQUENCE: 42

Cys Xaa Xaa Xaa Xaa Xaa Xaa Xaa Cys Xaa Xaa Xaa Xaa Xaa Xaa Cys
 1               5                  10                  15

Xaa Xaa Xaa His
            20

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      Cys3His zinc-finger motif
<220> FEATURE:
<221> NAME/KEY: MOD_RES
<222> LOCATION: (2)..(8)
<223> OTHER INFORMATION: Variable residue
<220> FEATURE:
<221> NAME/KEY: MOD_RES
<222> LOCATION: (10)..(13)
<223> OTHER INFORMATION: Variable residue
<220> FEATURE:
<221> NAME/KEY: MOD_RES
<222> LOCATION: (15)..(17)
<223> OTHER INFORMATION: Variable residue

<400> SEQUENCE: 43

Cys Xaa Xaa Xaa Xaa Xaa Xaa Xaa Cys Xaa Xaa Xaa Xaa Cys Xaa Xaa
 1               5                  10                  15

Xaa His

```
<210> SEQ ID NO 44
<211> LENGTH: 58
<212> TYPE: RNA
<213> ORGANISM: Unknown Organism
<220> FEATURE:
<223> OTHER INFORMATION: Description of Unknown Organism: Preferred
      oligonucleotide of the invention

<400> SEQUENCE: 44
cucccagacu aaccugucuc gcuuucccc uccgcugcgg ccacucccug aaccucag        58

<210> SEQ ID NO 45
<211> LENGTH: 58
<212> TYPE: DNA
<213> ORGANISM: Unknown Organism
<220> FEATURE:
<223> OTHER INFORMATION: Description of Combined DNA/RNA Molecule:
      Preferred oligonucleotide of the invention
<220> FEATURE:
<223> OTHER INFORMATION: Description of Unknown Organism: Preferred
      oligonucleotide of the invention

<400> SEQUENCE: 45
cucccagacu aaccauaaua auauuucccc uccgcugcgg ccactcccug aaccucag        58

<210> SEQ ID NO 46
<211> LENGTH: 58
<212> TYPE: RNA
<213> ORGANISM: Unknown Organism
<220> FEATURE:
<223> OTHER INFORMATION: Description of Unknown Organism: Preferred
      oligonucleotide of the invention

<400> SEQUENCE: 46
cucccagacu aaccugucuc gcuauaauaa uacccugcgg ccacucccug aaccucag        58

<210> SEQ ID NO 47
<211> LENGTH: 58
<212> TYPE: RNA
<213> ORGANISM: Unknown Organism
<220> FEATURE:
<223> OTHER INFORMATION: Description of Unknown Organism: Preferred
      oligonucleotide of the invention

<400> SEQUENCE: 47
cucccagacu aaccugucuc gcuuucccc ucauaauaau acacucccug aaccucag        58

<210> SEQ ID NO 48
<211> LENGTH: 58
<212> TYPE: RNA
<213> ORGANISM: Unknown Organism
<220> FEATURE:
<223> OTHER INFORMATION: Description of Unknown Organism: Preferred
      oligonucleotide of the invention

<400> SEQUENCE: 48
cucccagacu aaccugucuc gcuuucccc uccgcugcgg cauaauaaua aaccucag         58

<210> SEQ ID NO 49
<211> LENGTH: 50
<212> TYPE: RNA
<213> ORGANISM: Unknown Organism
<220> FEATURE:
<223> OTHER INFORMATION: Description of Unknown Organism: Preferred
      oligonucleotide of the invention

<400> SEQUENCE: 49
```

```
cucccagacu aaccugucuc gcuuuccccc uccgcugcgg ccacucccug        50

<210> SEQ ID NO 50
<211> LENGTH: 58
<212> TYPE: RNA
<213> ORGANISM: Unknown Organism
<220> FEATURE:
<223> OTHER INFORMATION: Description of Unknown Organism: Preferred
      oligonucleotide of the invention

<400> SEQUENCE: 50
cucccagacu aaccuuucuc ccuuuccccc uccccuucgg ccacucccug aaccucag        58

<210> SEQ ID NO 51
<211> LENGTH: 37
<212> TYPE: RNA
<213> ORGANISM: Unknown Organism
<220> FEATURE:
<223> OTHER INFORMATION: Description of Unknown Organism: Preferred
      oligonucleotide of the invention

<400> SEQUENCE: 51
cgcuuuccuu ucauucuuuc acuucucugc ugcuuuu        37

<210> SEQ ID NO 52
<211> LENGTH: 12
<212> TYPE: RNA
<213> ORGANISM: Homo sapiens

<400> SEQUENCE: 52
ugucucgcuu uu        12

<210> SEQ ID NO 53
<211> LENGTH: 10
<212> TYPE: RNA
<213> ORGANISM: Gallus gallus

<400> SEQUENCE: 53
ugcugcuuuu        10

<210> SEQ ID NO 54
<211> LENGTH: 1114
<212> TYPE: DNA
<213> ORGANISM: Homo sapiens

<400> SEQUENCE: 54
ccccgctgag actgagcaga cgcctccagg atctgtcggc agctgctgtt ctgagggaga        60
gcagagacca tgtctgacat agaagaggtg gtggaagagt acgaggagga ggagcaggaa       120
gagcaggagg aggcagcgga agaggatgct gaagcagagg ctgagaccga ggagaccagg       180
gcagaagaag atgaagaaga agaggaagca aaggaggctg aagatggccc aatggaggag       240
tccaaaccaa agcccaggtc gttcatgccc aacttggtgc ctcccaagat ccccgatgga       300
gagagagtgg actttgatga catccaccgg aagcgcatgg agaaggacct gaatgagttg       360
caggcgctga tcgaggctca cttttgagaac aggaagaaag aggaggagga gctcgttttct       420 ctcaaagaca ggatcgagag acgtcgggca gagcgggccg agcagcagcg catccggaat       480
gagcgggaga aggagcggca gaaccgcctg gctgaagaga gggctcgacg agaggaggag       540
gagaacagga ggaaggctga ggatgaggcc cggaagaaga aggctttgtc caacatgatg       600
cattttgggg gttacatcca gaaggcccag acagagcgga aaagtgggaa gaggcagact       660
gagcgggaaa agaagaagaa gattctggct gagaggagga aggtgctggc cattgaccac       720
```

```
ctgaatgaag atcagctgag ggagaaggcc aaggagctgt ggcagagcat ctataacttg    780
gaggcagaga agttcgacct gcaggagaag ttcaagcagc agaaatatga gatcaatgtt    840
ctccgaaaca ggatcaacga taaccagaaa gtctccaaga cccgcgggaa ggctaaagtc    900
accgggcgct ggaaatagag cctggcctcc ttcaccaaag atctgctcct cgctcgcacc    960
tgcctccggc ctgcactccc ccagttcccg ggcctcctg ggcacccag gcagctcctg    1020 tttggaaatg gggagctggc ctaggtggga gccaccactc ctgcctgccc ccacacccac    1080
tccacaccag taataaaaag ccaccacaca ctga                               1114

<210> SEQ ID NO 55
<211> LENGTH: 1000
<212> TYPE: DNA
<213> ORGANISM: Homo sapiens

<400> SEQUENCE: 55
cccaccttca ccatgtctga cgaggaagtt gaacaggtgg aggagcagta cgaagaagaa     60
gaggaagccc aggaggaaga ggaagttcaa gaagacaccg cagaggagga cgcggaagag    120
gagaaaccga gacccaaact cactgctcct aagatcccag aaggggagaa agtggacttc    180
gatgacatcc agaagaagcg tcagaacaaa gacctaatgg agctccaggc cctcatcgac    240
agccactttg aagcccggaa gaaggaggag gaggagctgg tcgctctcaa agagagaatc    300
gagaagcgcc gtgcagagag agcggagcag cagaggattc gtgcagagaa ggagagggag    360
cgccagaaca gactggcgga ggaaaaggcc agaagggagg aggaggatgc caagaggagg    420
gcagaggacg acctgaagaa gaagaaagcg ctgtcctcca tgggcgccaa ctacagcagc    480
tacctggcca aggctgacca gaagagaggc aagaagcaga cagcccgaga gatgaagaag    540
aagattctgg ctgagagacg caagccgctc aacatcgatc accttggtga agacaaactg    600
agggacaagg ccaaggagct ctgggagacc ctgcaccagc tggagattga caagttcgag    660
tttggggaga agctgaaacg ccagaaatat gacatcacca cgctcaggag ccgcattgac    720
caggcccaga agcacagcaa gaaggctggg acccccagcca agggcaaagt cggcgggcgc    780
tggaagtaga gaggccagaa aggccctcga ggcagagacc ctccgccctc ttgcacacca    840
gggccgctcg tgggactcca catcctccag cccccacaat cctgtcaggg gtctccctga    900
cgtcctgggg gtggagaggc catcccgggg cgtccccgc gtctgtgtcc ttgctgcctt    960
catcccctgg ggcctgtgaa taaagctgca gaacccccctt                       1000
```